(12) United States Patent
Farritor et al.

(10) Patent No.: US 11,872,090 B2
(45) Date of Patent: *Jan. 16, 2024

(54) ROBOTIC SURGICAL DEVICES, SYSTEMS, AND RELATED METHODS

(71) Applicant: Virtual Incision Corporation, Lincoln, NE (US)

(72) Inventors: Shane Farritor, Lincoln, NE (US); Jeffrey Shasho, Brooklyn, NY (US); Nishant Kumar, Bergenfield, NJ (US); Mateusz Szczesiak, Forest Hills, NY (US); Jason Herman, East Northport, NY (US); Chris Santoro, Brooklyn, NY (US)

(73) Assignee: Virtual Incision Corporation, Lincoln, NE (US)

( * ) Notice: Subject to any disclaimer, the term of this patent is extended or adjusted under 35 U.S.C. 154(b) by 360 days.

This patent is subject to a terminal disclaimer.

(21) Appl. No.: 17/075,122

(22) Filed: Oct. 20, 2020

(65) Prior Publication Data

US 2021/0045836 A1    Feb. 18, 2021

Related U.S. Application Data

(63) Continuation of application No. 15/227,813, filed on Aug. 3, 2016, now Pat. No. 10,806,538.

(Continued)

(51) Int. Cl.
*A61B 90/00* (2016.01)
*A61B 1/00* (2006.01)
(Continued)

(52) U.S. Cl.
CPC .......... *A61B 90/361* (2016.02); *A61B 1/0051* (2013.01); *A61B 1/00128* (2013.01);
(Continued)

(58) Field of Classification Search
CPC ............ A61B 1/00128; A61B 1/00135; A61B 1/00137; A61B 1/00154
See application file for complete search history.

(56) References Cited

U.S. PATENT DOCUMENTS 2,858,947 A    11/1958    Chapman, Jr.
3,817,403 A    6/1974    Glachet et al.
(Continued)

FOREIGN PATENT DOCUMENTS

CA    2918531 A1    1/2015
CN    102499759 A    6/2012
(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
(Continued)

*Primary Examiner* — Matthew J Kasztejna
(74) *Attorney, Agent, or Firm* — Fredrikson & Byron, P.A.

(57) ABSTRACT

The various inventions relate to robotic surgical devices, consoles for operating such surgical devices, operating theaters in which the various devices can be used, insertion systems for inserting and using the surgical devices, and related methods.

20 Claims, 48 Drawing Sheets

Related U.S. Application Data

(60) Provisional application No. 62/200,563, filed on Aug. 3, 2015.

(51) Int. Cl.
*A61B 1/005* (2006.01)
*A61B 34/30* (2016.01)
*A61B 34/00* (2016.01)
*A61B 34/35* (2016.01)
*A61B 90/30* (2016.01)
*A61B 34/20* (2016.01)

(52) U.S. Cl.
CPC ...... *A61B 1/00135* (2013.01); *A61B 1/00137* (2013.01); *A61B 1/00154* (2013.01); *A61B 34/30* (2016.02); *A61B 34/35* (2016.02); *A61B 34/76* (2016.02); *A61B 2034/2048* (2016.02); *A61B 2034/2059* (2016.02); *A61B 2034/252* (2016.02); *A61B 2034/301* (2016.02); *A61B 2034/302* (2016.02); *A61B 2034/303* (2016.02); *A61B 2034/305* (2016.02); *A61B 2090/306* (2016.02)

(56) References Cited

U.S. PATENT DOCUMENTS

| | | |
|---|---|---|
| 3,870,264 A | 3/1975 | Robinson |
| 3,922,930 A | 12/1975 | Fletcher et al. |
| 3,971,266 A | 7/1976 | Inakura et al. |
| 3,989,952 A | 11/1976 | Timberlake et al. |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyaki |
| 4,576,545 A | 3/1986 | Maeda |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch |
| 4,854,808 A | 8/1989 | Bisiach |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,305,653 A | 4/1994 | Ohtani et al. |
| 5,307,447 A | 4/1994 | Asano et al. |
| 5,353,807 A | 10/1994 | DeMarco |
| 5,363,935 A | 11/1994 | Schempf et al. |
| 5,372,147 A | 12/1994 | Lathrop, Jr. et al. |
| 5,382,885 A | 1/1995 | Salcudean et al. |
| 5,441,494 A | 1/1995 | Oritz |
| 5,388,528 A | 2/1995 | Pelrine et al. |
| 5,397,323 A | 3/1995 | Taylor et al. |
| 5,436,542 A | 7/1995 | Petelin et al. |
| 5,456,673 A | 10/1995 | Ziegler et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,377 A * | 4/1999 | Smith ............... A61B 17/3462 604/167.03 |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |

(56) References Cited

U.S. PATENT DOCUMENTS

| | | |
|---|---|---|
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 | 9/2002 | Cassidy |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |

(56) References Cited

U.S. PATENT DOCUMENTS

| | | |
|---|---|---|
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 * | 1/2007 | Franer ............... A61B 17/3498 604/167.03 |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 * | 10/2008 | Hart ................... A61B 17/3462 604/167.03 |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 * | 8/2010 | Hueil ................ A61B 17/3462 606/185 |
| 7,785,333 B2 | 8/2010 | Miyamoto et al. |
| 7,789,825 B2 | 9/2010 | Nobis et al. |
| 7,789,861 B2 * | 9/2010 | Franer ............... A61B 17/3462 604/167.01 |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 8,021,358 B2 | 9/2011 | Doyle et al. |
| 8,179,073 B2 | 5/2012 | Farritor et al. |
| 8,231,610 B2 | 7/2012 | Jo et al. |
| 8,343,171 B2 | 1/2013 | Farritor et al. |
| 8,353,897 B2 | 1/2013 | Doyle et al. |
| 8,377,045 B2 | 2/2013 | Schena |
| 8,430,851 B2 | 4/2013 | Mcginley et al. |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 | 9/2014 | Farritor et al. |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 | 12/2015 | Wang et al. |
| 9,516,996 B2 | 12/2016 | Diolaiti et al. |
| 9,579,088 B2 | 2/2017 | Farritor et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,398,516 B2 | 9/2019 | Jackson et al. |
| 10,470,828 B2 | 11/2019 | Markvicka et al. |
| 10,507,066 B2 | 12/2019 | Dimaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 | 8/2020 | Farritor et al. |
| 10,751,883 B2 | 8/2020 | Nahum |
| 10,806,538 B2 | 10/2020 | Farritor et al. |
| 10,966,700 B2 | 4/2021 | Farritor et al. |
| 11,032,125 B2 | 6/2021 | Farritor et al. |
| 11,298,195 B2 | 4/2022 | Ye et al. |
| 11,382,702 B2 | 7/2022 | Tognaccini et al. |
| 11,529,201 B2 | 12/2022 | Mondry et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |

(56) References Cited

U.S. PATENT DOCUMENTS

| | | |
|---|---|---|
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Koshino |
| 2005/0054902 A1 | 3/2005 | Konno |
| 2005/0064378 A1 | 3/2005 | Toly |
| 2005/0065400 A1 | 3/2005 | Banik et al. |
| 2005/0070850 A1 | 3/2005 | Albrecht |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088277 A1 | 4/2007 | Mcginley et al. |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1 | 3/2008 | Cooper et al. |
| 2008/0071290 A1 | 3/2008 | Larkin et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0192524 A1 | 7/2009 | Itkowitz et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0026347 A1 | 2/2010 | Iizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |

(56) References Cited

U.S. PATENT DOCUMENTS

| | | |
|---|---|---|
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |
| 2010/0292691 A1 | 11/2010 | Brogna |
| 2010/0301095 A1 | 12/2010 | Shelton, IV et al. |
| 2010/0318059 A1 | 12/2010 | Farritor et al. |
| 2010/0331856 A1 | 12/2010 | Carlson et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0075693 A1 | 3/2011 | Kuramochi et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0107866 A1 | 5/2011 | Oka et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238079 A1 | 9/2011 | Hannaford et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |
| 2012/0016175 A1 | 1/2012 | Roberts et al. |
| 2012/0029727 A1 | 2/2012 | Sholev |
| 2012/0035582 A1 | 2/2012 | Nelson et al. |
| 2012/0059392 A1 | 3/2012 | Diolaiti |
| 2012/0078053 A1 | 3/2012 | Phee et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0221147 A1 | 8/2012 | Goldberg et al. |
| 2012/0253515 A1 | 10/2012 | Coste-Maniere et al. |
| 2013/0001970 A1 | 1/2013 | Suyama et al. |
| 2013/0041360 A1 | 2/2013 | Farritor et al. |
| 2013/0055560 A1 | 3/2013 | Nakasugi et al. |
| 2013/0125696 A1 | 5/2013 | Long |
| 2013/0131695 A1 | 5/2013 | Scarfogliero et al. |
| 2013/0178867 A1 | 7/2013 | Farritor et al. |
| 2013/0282023 A1 | 10/2013 | Burbank et al. |
| 2013/0304084 A1 | 11/2013 | Beira et al. |
| 2013/0325030 A1 | 12/2013 | Hourtash et al. |
| 2013/0345717 A1 | 12/2013 | Markvicka et al. |
| 2013/0345718 A1 | 12/2013 | Crawford et al. |
| 2014/0039515 A1 | 2/2014 | Mondry et al. |
| 2014/0046340 A1 | 2/2014 | Wilson et al. |
| 2014/0055489 A1 | 2/2014 | Itkowitz et al. |
| 2014/0058205 A1 | 2/2014 | Frederick et al. |
| 2014/0100587 A1 | 4/2014 | Farritor et al. |
| 2014/0137687 A1 | 5/2014 | Nogami et al. |
| 2014/0221749 A1 | 8/2014 | Grant |
| 2014/0232824 A1 | 8/2014 | Dimaio et al. |
| 2014/0276944 A1 | 9/2014 | Farritor et al. |
| 2014/0303434 A1 | 10/2014 | Farritor et al. |
| 2014/0371762 A1 | 12/2014 | Farritor et al. |
| 2015/0051446 A1 | 2/2015 | Farritor et al. |
| 2015/0057537 A1 | 2/2015 | Dillon et al. |
| 2015/0157191 A1 | 6/2015 | Phee et al. |
| 2015/0223896 A1 | 8/2015 | Farritor et al. |
| 2015/0297299 A1 | 10/2015 | Yeung et al. |
| 2016/0066999 A1 | 3/2016 | Forgione et al. |
| 2016/0135898 A1 | 5/2016 | Frederick et al. |
| 2016/0291571 A1 | 10/2016 | Cristiano |
| 2016/0303745 A1 | 10/2016 | Rockrohr |
| 2017/0014197 A1 | 1/2017 | Mccrea et al. |
| 2017/0035526 A1 | 2/2017 | Farritor et al. |
| 2017/0078583 A1 | 3/2017 | Haggerty |
| 2017/0252096 A1 | 9/2017 | Felder et al. |
| 2017/0354470 A1 | 12/2017 | Farritor et al. |
| 2018/0132956 A1 | 5/2018 | Cameron |
| 2018/0153578 A1 | 6/2018 | Cooper et al. |
| 2018/0338777 A1 | 11/2018 | Bonadio et al. |
| 2019/0059983 A1 | 2/2019 | Germain et al. |
| 2019/0090965 A1 | 3/2019 | Farritor et al. |
| 2019/0209262 A1 | 7/2019 | Mustufa et al. |
| 2019/0327394 A1 | 10/2019 | Ramirez et al. |
| 2020/0214775 A1 | 7/2020 | Farritor et al. |
| 2020/0330175 A1 | 10/2020 | Cameron |
| 2020/0368915 A1 | 11/2020 | Itkowitz et al. |

FOREIGN PATENT DOCUMENTS

| | | |
|---|---|---|
| CN | 102821918 | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 105025826 A | 11/2015 |
| DE | 102010040405 | 3/2012 |
| EP | 0105656 A2 | 4/1984 |
| EP | 0279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 10/2015 |
| EP | 2937047 A1 | 10/2015 |
| JP | S59059371 A | 4/1984 |
| JP | S61165061 A | 7/1986 |
| JP | S62068293 A | 3/1987 |
| JP | H04-144533 A | 5/1992 |
| JP | 05-115425 | 5/1993 |
| JP | H05-115425 A | 5/1993 |
| JP | 2006508049 | 9/1994 |
| JP | H06-507809 A | 9/1994 |
| JP | H06-508049 A | 9/1994 |
| JP | 07-016235 | 1/1995 |
| JP | 07-136173 | 5/1995 |
| JP | H07-136173 A | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004283940 A | 10/2004 |
| JP | 2004322310 | 11/2004 |
| JP | 2004329292 | 11/2004 |
| JP | 2006507809 | 3/2006 |
| JP | 2009106606 | 5/2009 |
| JP | 2009297809 A | 12/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| JP | 2012504017 A | 2/2012 |
| JP | 2012176489 A | 9/2012 |
| JP | 5418704 B1 | 2/2014 |
| JP | 2015526171 A | 9/2015 |
| JP | 5959371 B2 | 8/2016 |
| JP | 2016213937 A | 12/2016 |
| JP | 2017113837 A | 6/2017 |
| JP | 5268293 B2 | 1/2018 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |

(56) References Cited

FOREIGN PATENT DOCUMENTS

| | | |
|---|---|---|
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009014917 A2 | 1/2009 |
| WO | 2009023851 | 2/2009 |
| WO | 2009144729 | 12/2009 |
| WO | 2009158164 A1 | 12/2009 |
| WO | 2010039394 A1 | 4/2010 |
| WO | 2010042611 A1 | 4/2010 |
| WO | 2010046823 A1 | 4/2010 |
| WO | 2010050771 | 5/2010 |
| WO | 2010083480 A2 | 7/2010 |
| WO | 2011075693 | 6/2011 |
| WO | 2011118646 | 9/2011 |
| WO | 2011135503 | 11/2011 |
| WO | 2011163520 A2 | 12/2011 |
| WO | 2013009887 | 1/2013 |
| WO | 2013052137 A2 | 4/2013 |
| WO | 2013106569 A2 | 7/2013 |
| WO | 2014011238 | 1/2014 |
| WO | 2014025399 A1 | 2/2014 |
| WO | 2014144220 A1 | 9/2014 |
| WO | 2014146090 A1 | 9/2014 |
| WO | 2015009949 A2 | 1/2015 |
| WO | 2015031777 A1 | 3/2015 |
| WO | 2015088655 A1 | 6/2015 |
| WO | 2016077478 A1 | 5/2016 |
| WO | 2017024081 A1 | 2/2017 |
| WO | 2017064303 A1 | 4/2017 |
| WO | 2017201310 A1 | 11/2017 |
| WO | 2018045036 A1 | 3/2018 |

OTHER PUBLICATIONS

Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.

Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rooties: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al.," Prospective Comparison of Open vs. Laparoscopic Colon Surgery for Carcinoma: Five-Year Results," Dis Colon Rectum, 1996; 39: S35-S46.
Flynn et al., "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-13.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al.," Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31: 1372-1382.
Cavusoglu et al.," Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Abbou et al., "Laparoscopic Radical Prostatectomy with a Remote Controlled Robot," The Journal of Urology, Jun. 2001; 165: 1964-1966.

(56) References Cited

OTHER PUBLICATIONS

Albers et al., Design and development process of a humanoid robot upper body through experimentation, 2004, IEEE, p. 77-92 (Year: 2004).
Crystal Eyes, http://www.reald.com, 2007 (Stereo 3D visualization for CAVEs, theaters and immersive environments), 1 pg.
Definition of Individually. Dictionary.com, retrieved on Aug. 9, 2016; Retrieved from the Internet: <http://www.dictionary.com/browse/individually>, 1 page.
Glukhovsky et al., "The development and application of wireless capsule endoscopy," Int. J. Med. Robot. Comput. Assist. Surgery, 2004; I(1): 114-123.
Gong et al., "Wireless endoscopy," Gastrointestinal Endoscopy 2000; 51 (6): 725-729.
Gopura et al., Mechanical designs of active upper-limb exoskeleton robots: State-of-the-art and design difficulties, 2009, IEEE, p. 178-187 (Year: 2009).
Gopura et al., A brief review on upper extremity robotic exoskeleton systems, 2011, IEEE, p. 346-351 (Year: 2011).
Guo et al., "Micro Active Guide Wire Catheter System—Characteristic Evaluation, Electrical Model* and Operability Evaluation of Micro Active Catheter," Proceedings of the 1996 IEEE International Conference on Robotics and Automation, Apr. 1996; 2226-2231.
Guo et al., "Fish-like Underwater Microrobot with 3 DOF," Proceedings of the 2002 IEEE International Conference on Robotics & Automation, May 2002; 738-743.
Hanly et al., "Robotic Abdominal Surgery," The American Journal of Surgery, 2004; 188 (Suppl.to Oct. 1994); 19S-26S.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14:1019-1023.
Hissink, "Olympus Medical develops capsule camera technology," Dec. 2004, accessed Aug. 29, 2007, http://www.letsgodigital.org, 3 pp.
Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000; 65-69.
Jagannath et al., "Peroral transgastric endoscopic ligation of fallopian tubes with long-term survival in a porcine model," Gastrointestinal Endoscopy, 2005; 61 (3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001: 94-104.
Kantsevoy et al., "Transgastric endoscopic splenectomy," Surgical Endoscopy, 2006; 20: 522-525.
"Kantsevoy et al., ""Endoscopic gastrojejunostomy with survival in a porcine model,"" Gastrointestinal Endoscopy, 2005; 62(2): 287-292."
Kazemier et al. (1998), "Vascular Injuries During Laparoscopy," J. Am. Coli. Surg. 186(5): 604-5.
Keller et al., Design of the pediatric arm rehabilitation robot ChARMin, 2014, IEEE, p. 530-535 (Year: 2014).
"Kim, ""Early Experience with Telemanipulative Robot-Assisted Laparoscopic CholecystectomyUsing da Vinci,"" Surgical Laparoscopy, Endoscopy & Percutaneous Techniques, 2002; 12(1): 33-40."
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136: 180-184.
Leggett et al. (2002), "Aortic injury during laparoscopic Fundoplication," Surg. Endoscopy 16(2): 362.

Li et al. (2000), "Microvascular Anastomoses Performed in Rats Using a Microsurgical Telemanipulator," Comp. Aid. Surg., 5: 326-332.
Liem et al., "Comparison of Conventional Anterior Surgery and Laparoscopic Surgery for Inguinal-hernia Repair," New England Journal of Medicine, 1997; 336 (22): 1541-1547.
Lou Cubrich, "A Four-DOF Laparo-Endoscopic Single Site Platform for Rapidly-Developing Next Generation Surgical Robotics", Journal of Medical Robotics Research, vol. 1, No. 4, 2016, 165006-1-165006-15.
Macfarlane et al., "Force-Feedback Grasper Helps Restore the Sense of Touch in Minimally Invasive Surgery," Journal of Gastrointestinal Surgery, 1999; 3:278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al. "Wireless Drive and Control of a Swimming Microrobot," Proceedings of the 2002 IEEE International Conference on Robotics & Automation, May 2002: 1131-1136.
Menciassi et al., "Robotic Solutions and Mechanisms for a Semi-Autonomous Endoscope," Proceedings of the 2002 IEEE/RSJ Intl. Conference on Intelligent Robotsand Systems, Oct. 2002; 1379-1384.
Melvin et al., "Computer-Enhanced vs. Standard Laparoscopic Antireflux Surgery," J Gastrointest Surg 2002; 6: 11-16.
Menciassi et al., "Locomotion of a Letfed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Shape memory alloy clamping devices of a capsule for monitoring tasks in the gastrointestinal tract," J. Micromech. Microeng, 2005; 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.
Midday Jeff et al., "Material Handling System for Robotic natural Orifice Surgery,", Proceedings of the 2011 Design of medical Devices Conference, Apr. 12-14, 2011, Minneapolis, MN 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp., 2004.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "Miniature Robots Can Assist in Laparoscopic Cholecystectomy," Journal of Surgical Endoscopy, 19-4: 473-476, 2005.
Oleynikov et al., "In Vivo Robotic Laparoscopy," Surgical Innovation, Jun. 2005, 12(2): 177-181.
O'Neill, "Surgeon takes new route to gallbladder," The Oregonian, Jun. 2007; 2 pp.
Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.
Palm, William. "Rapid Prototyping Primer" May 1998 (revised Jul. 30, 2002) (http://www.me.psu.edu/lamancusa/rapidpro/primer/chapter2.htm), 12 pages.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960 filed Feb. 2000.
U.S. Appl. No. 60/956,032, filed Aug. 15, 2007.
U.S. Appl. No. 60/983,445, filed Oct. 29, 2007.

(56) References Cited

OTHER PUBLICATIONS

U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Worn et al., "Espirit Project No. 33915: Miniaturised Robot for Micro Manipulation (MINIMAN)," Nov. 1998, http://www.ipr.ira.ujka.de/-microbot/miniman.
Way et al., editors, "Fundamentals of Laparoscopic Surgery," Churchill Livingstone Inc., 1995; 14 pp.
Wolfe et al. (1991), Endoscopic Cholecystectomy: An analysis of Complications, Arch. Surg. 1991; 126: 1192-1196.
Xu et al. "System Design of an Insertable Robotic Effector Platform for Single Access (SPA) Surgery", The 2009 IEEE/RSJ International Conference on Intelligent Robots and Systems, Oct. 11-15, 2009, St. Louis MO USA pp. 5546-5552.
Yu, BSN, RN, "M2ATM Capsule Endoscopy a Breakthrough Diagnostic Tool for Small Intestine Imagining," vol. 25, No. 1, 2001, Gastroenterology Nursing, pp. 24-27.
Yu et al., "Microrobotic Cell Injection," Proceedings of the 2001 IEEE International Conference on Robotics and Automation, May 2001: 620-625.
Park et al., "Experimental studies of transgastric gallbladder surgery: cholecystectomy and cholecystogastric anastomosis (videos)," Gastrointestinal Endoscopy, 2005; 61 (4): 601-606.
Park et al., "Trocar-less Instrumentation for Laparoscopy: Magnetic Positioning of Intra-abdominal Camera and Retractor," Ann Surg, Mar. 2007; 245(3): 379-384.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, pp. 239-240, 2004.
Patronik et al., "Preliminary evaluation of a mobile robotic device for navigation and intervention on the beating heart," Computer Aided Surgery, 10(4): 225-232, Jul. 2005.
Peirs et al. "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Development of Microrobotic Devices for Locomotion in the Human GastrointestinalTract," International Conference on Computational Intelligence, Robotics and Autonomous Systems (Cl RAS 2001), Nov. 28-30, 2001, Singapore, 6 pages.
Phee et al., "Analysis and Development of Locomotion Devices for the Gastrointestinal Tract," IEEE Transactions on Biomedical Engineering, vol. 49, No. 6, Jun. 2002: 613-616.
"Platt et al., "In Vivo Robotic Cameras can Enhance Imaging Capability During Laparoscopic Surgery," from the Proceedings of the Society of American Gastrointestinal Endoscopic Surgeons-(SAGES) Scientific Conference, Ft. Lauderdale, FL, Apr. 13-16, 2005; 1 pg."
Qian Huan et al., "Multi-joint Single-wound Minimally Invasive Abdominal Surgery Robot Design," Mechanical Design and Manufacturing, May 8, 2014, pp. 134-137.
Rentschler et al., "In vivo Mobile Surgical Robotic Task Assistance," 1 pg.
"Rentschler et al., ""Theoretical and Experimental Analysis of In Vivo Wheeled Mobility,"" ASME Design Engineering Technical Conferences: 28th Biennial Mechanisms and Robotics Conference,Salt Lake Citv, Utah, Sep. 28-Oct. 2, 2004; pp. 1-9."
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Toward In Vivo Mobility," Studies in Health Technology and Infonnatics—Medicine Meets Virtual Reality, ISO Press, Long Beach, CA, 2005a, III: 397-403.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler, et al. "Miniature in vivo robots for remote and harsh environments," IEEE Transaction on Information Technology in Biomedicine, Jan. 2006; 12(1): pp. 66-75.
Rentschler et al., "Mechanical Design of Robotic In Vivo Wheeled Mobility," ASME Journal of Mechanical Design, 2006a; pp. 1-11, Accepted.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Natural Orifice Surgery with an Endoluminal Mobile Robot," The Society of American Gastrointestinal Endoscopic Surgeons, Dallas, TX, Apr. 2006d.
Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.
Rentschler et al., "Mobile In Vivo Biopsy Robot," IEEE International Conference on Robotics and Automation, Orlando, Florida, May 2006; 4155-4160.
Rentschler et al., "In vivo Robotics during the NEEMO 9 Mission," Medicine Meets Virtual Reality, Feb. 2007; 1 pg.
Rentschler et al., "An In Vivo Mobile Robot for Surgical Vision and Task Assistance," Journal of Medical Devices, Mar. 2007; vol. 1: 23-29.
Riviere et al., "Toward Active Tremor Canceling in Handheld Microsurgical Instruments," IEEE Transactions on Robotics and Automation, Oct. 2003, 19(5): 793-800.
"Rosen et al., ""Force Controlled and Teleoperated Endoscopic, Grasper for Minimally Invasive Surgery-Experimental Performance Evaluation,"" IEEE Transactions of Biomedical Engineering,Oct. 1999; 46(10): 1212-1221."
Rosen et al., "Task Decomposition of Laparoscopic Surgery for Objective Evaluation of SurgicalResidents' Learning Curve Using Hidden Markov Model," Computer Aided Surgery, vol. 7, pp. 49-61, 2002.
"Rosen et al., ""The Blue DRAGON—A System of Measuring the Kinematics and the Dynamics of Minimally Invasive Surgical Tools In-Vivo,"" Proc. of the 2002 IEEE International Conference onRobotics and Automation, Washington, DC, pp. 1876-1881, May 2002."
Rosen et al., Objective Evaluation of Laparoscopic Skills Based on Haptic Information and Tool/Tissue Interactions, Computer Aided Surgery, vol. 7, Issue 1, pp. 49-61, Jul. 2002.
Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448. Jan. 2005.
Ruurda et al., "Feasibility of Robot-Assisted Laparoscopic Surgery," Surgical Laparoscopy, Endoscopy & Percutaneous Techniques, 2002; 12(1):41-45.
Ruurda et al, "Robot-Assisted surgical systems: a new era in laparoscopic surgery," Ann R. Coll Surg Engl. 2002; 84: 223-226.
Salky, "What is the Penetration of Endoscopic Techniques into Surgical Practice?" Digestive Surgery 2000; 17:422-426.
Satava, "Surgical Robotics: The Early Chronicles," Surgical Laparoscopy, Endoscopy & Percutaneous Techniques, 2002; 12(1):6-16.
Schippers et al. (1996), "Requirements and Possibilities of Computer-Assisted Endoscopic Surgery," In: Computer Integrated Surgery: Technology and Clinical Applications, pp. 561-565.
"Schurr et al., ""Robotics and Telemanipulation Technologies for Endoscopic Surgery,"" Surgical Endoscopy, 2000; 14:375-381."
Schwartz, "In the Lab: Robots that Slink and Squirm," The New York Times, Mar. 27, 2007, 4 pp.
Sharp LL-151-3D, http://www.sharp3d.com, 2006, 2 pp.

(56) References Cited

OTHER PUBLICATIONS

Slatkin et al., "The Development of a Robotic Endoscope," Proceedings of the 1995 IEEE International Conference on Robotics and Automation, pp. 162-171, 1995.

Smart Pill "Fastastic Voyage: Smart Pill to Expand Testing," "http://www.smartpilldiagnostics.com, Apr. 13, 2005, 1 pg."

Sodeyama et al., A shoulder structure of muscle-driven humanoid with shoulder blades, 2005, IEEE, p. 1-6 (Year: 2005).

Southern Surgeons Club (1991), "A prospective analysis of 1518 laparoscopic cholecystectomies," N. Eng. 1 Med. 324(16): 1073-1078.

Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.

Stiff et al., "Long-term Pain: Less Common After Laparoscopic than Open Cholecystectomy," British Journal of Surgery, 1994; 81: 1368-1370.

Strong et al., "Efficacy of Novel Robotic Camera vs. a Standard Laproscopic Camera," Surgical Innovation vol. 12, No. 4, Dec. 2005, Westminster Publications, Inc., pp. 315-318.

Suzumori et al., "Development of Flexible Microactuator and its Applications to Robotics Mechanisms," Proceedings of the IEEE International Conference on Robotics and Automation, 1991: 1622-1627.

Taylor et al., "A Telerobotic Assistant for Laparoscopic Surgery," IEEE Eng Med Biol, 1995; 279-87.

Tendick et al. (1993), "Sensing and Manipulation Problems in Endoscopic Surgery: Experiment, Analysis, and Observation," Presence 2(1): 66-81.

Tendick et al., "Applications of Micromechatronics in Minimally Invasive Surgery," IEEE/ASME Transactions on Mechatronics, 1998; 3(1): 34-42.

\* cited by examiner

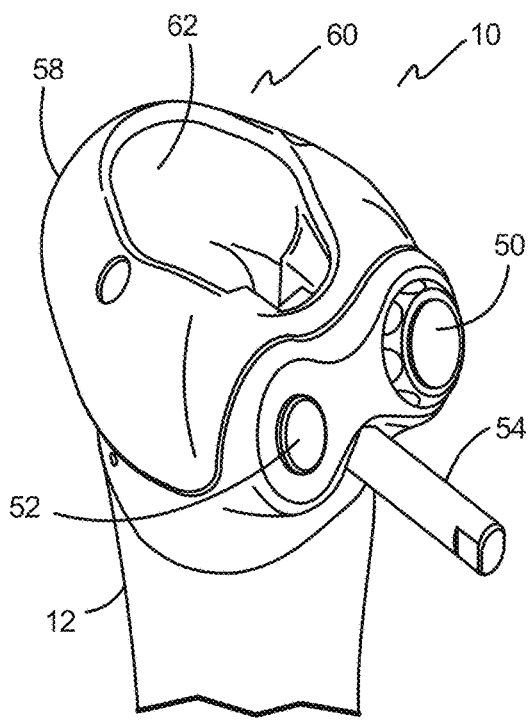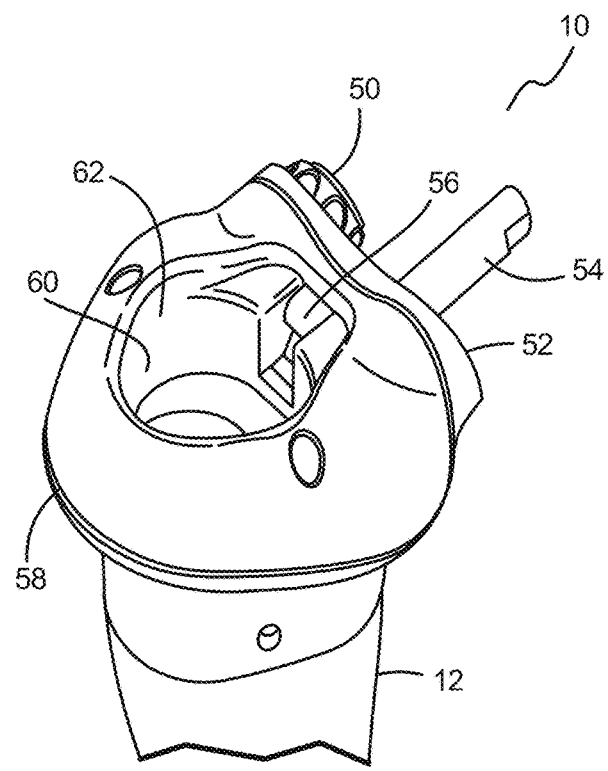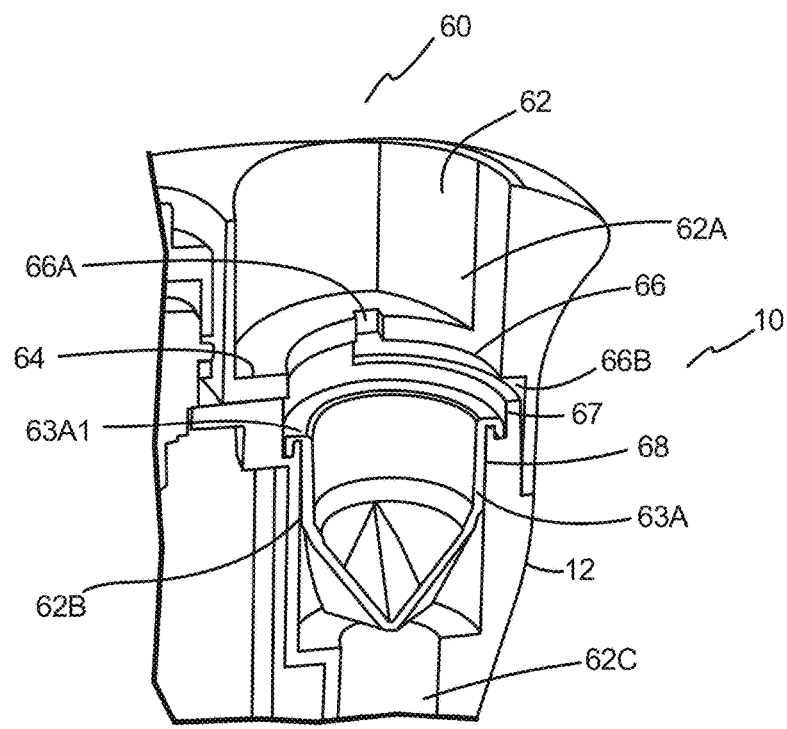

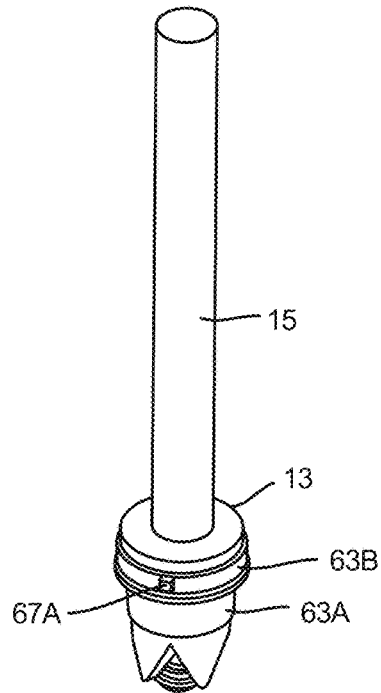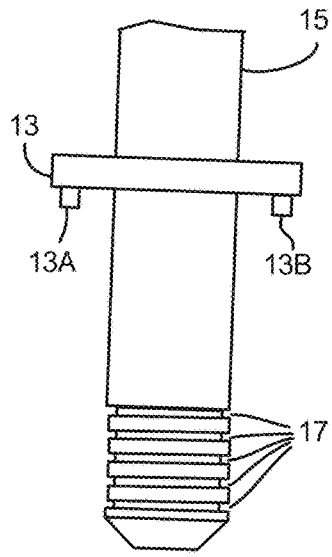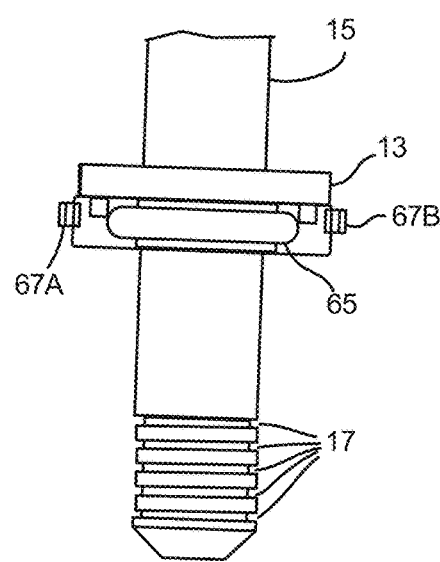
FIG. 3A    FIG. 3B    FIG. 3C
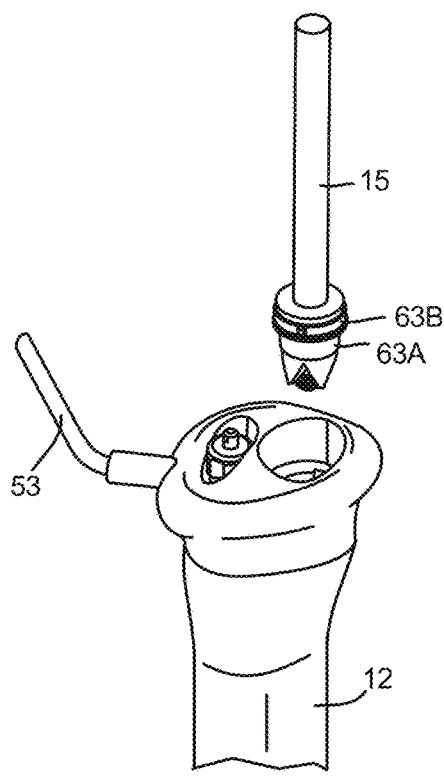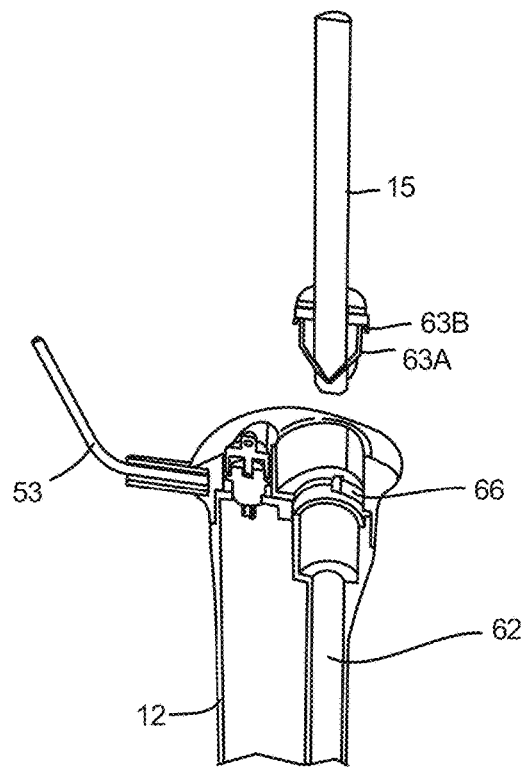
FIG. 3D    FIG. 3E

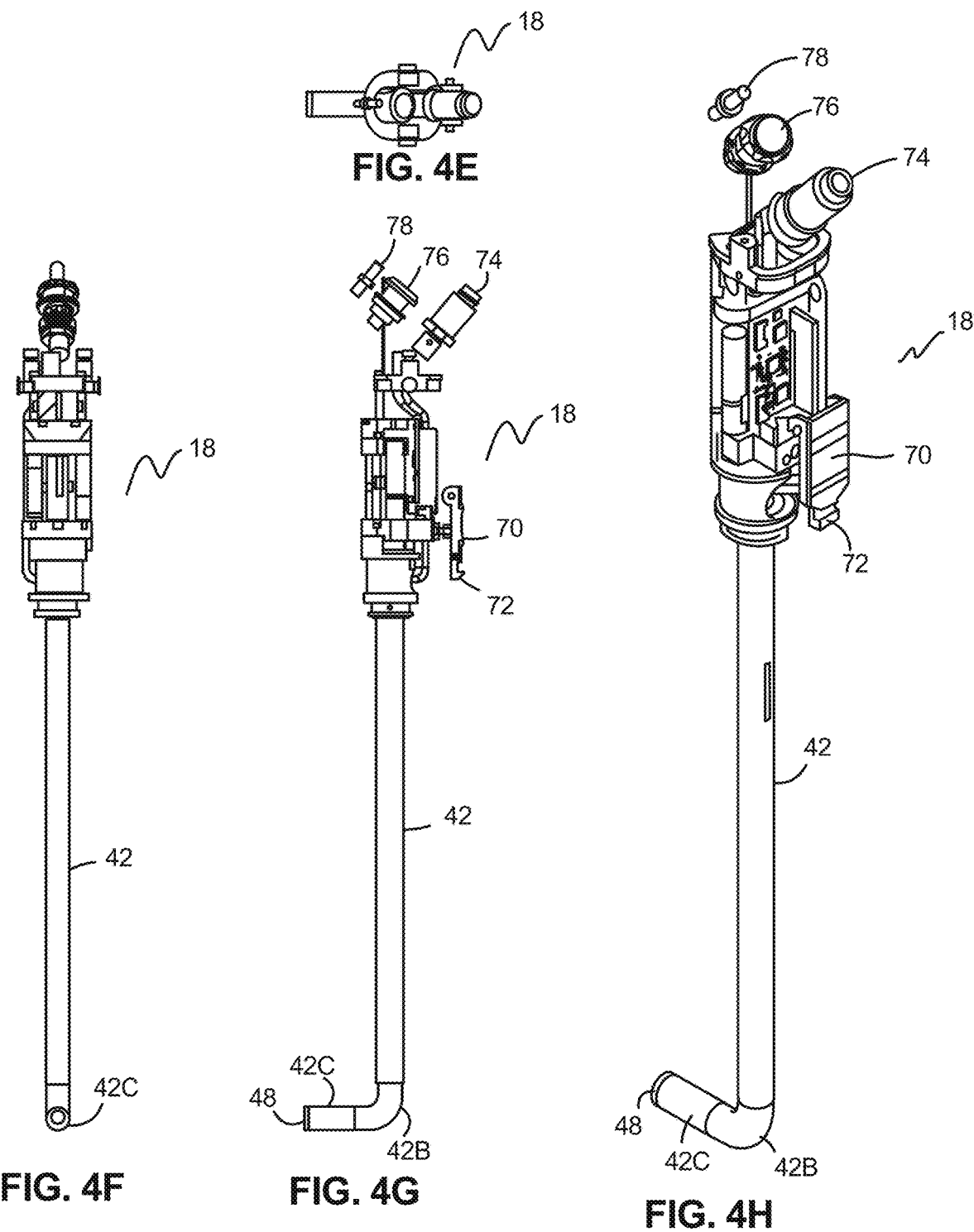

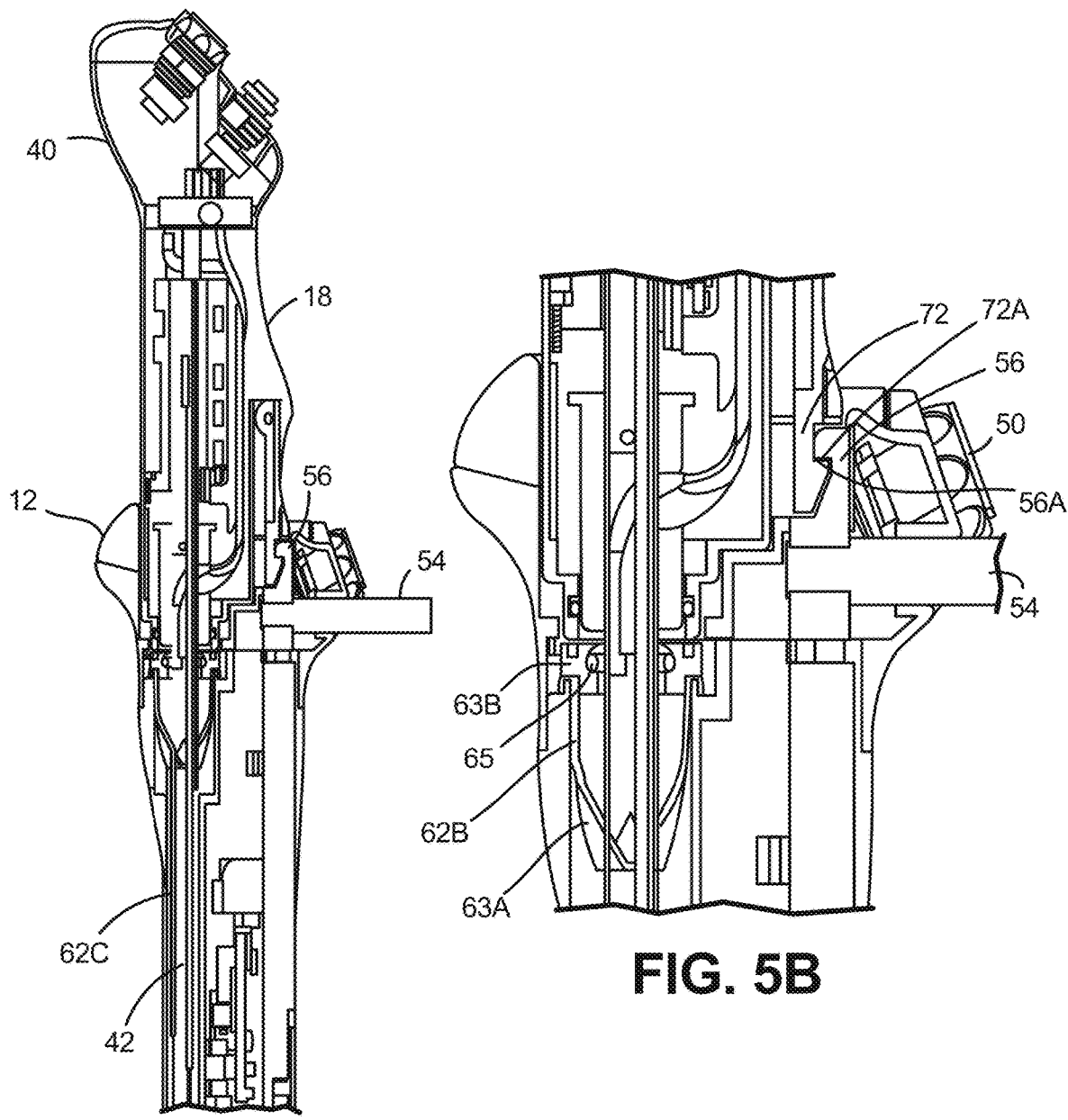

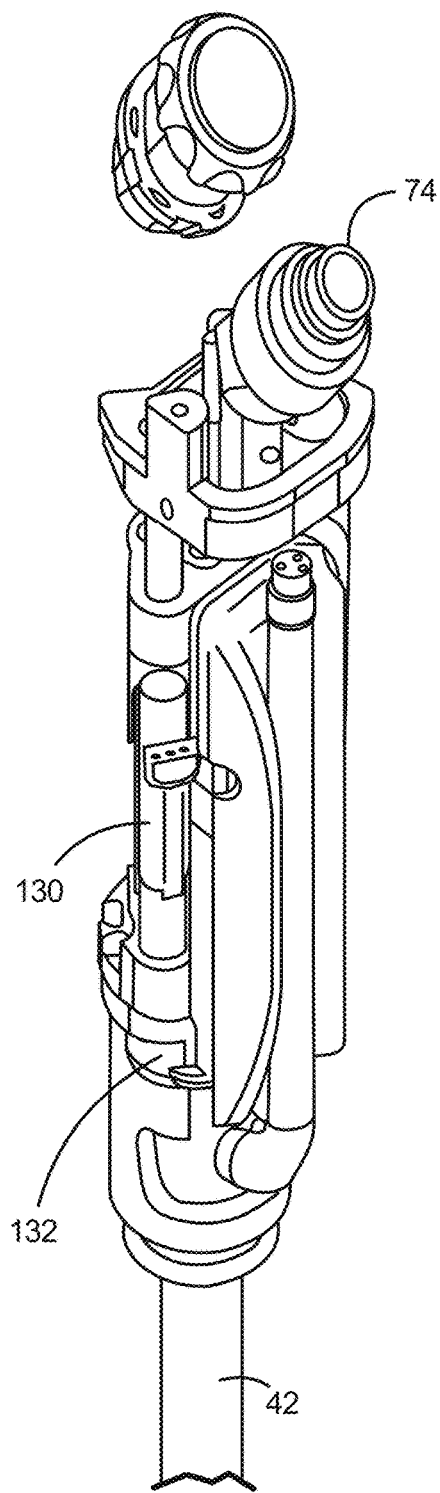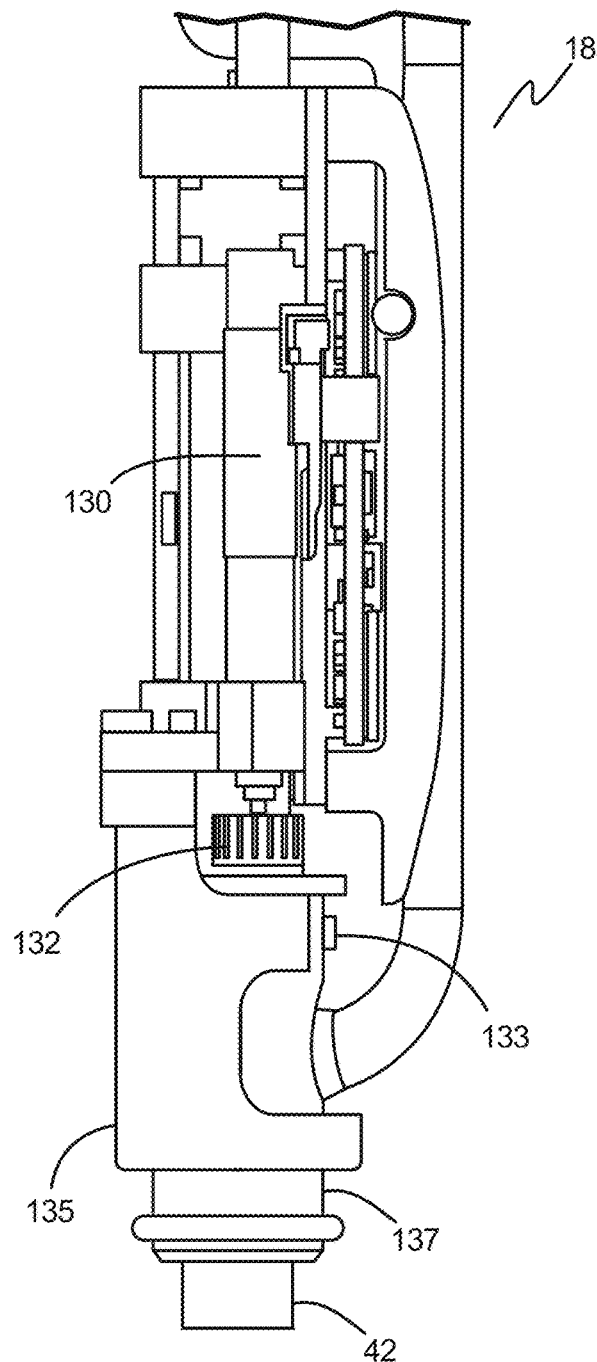
FIG. 6B
FIG. 6C

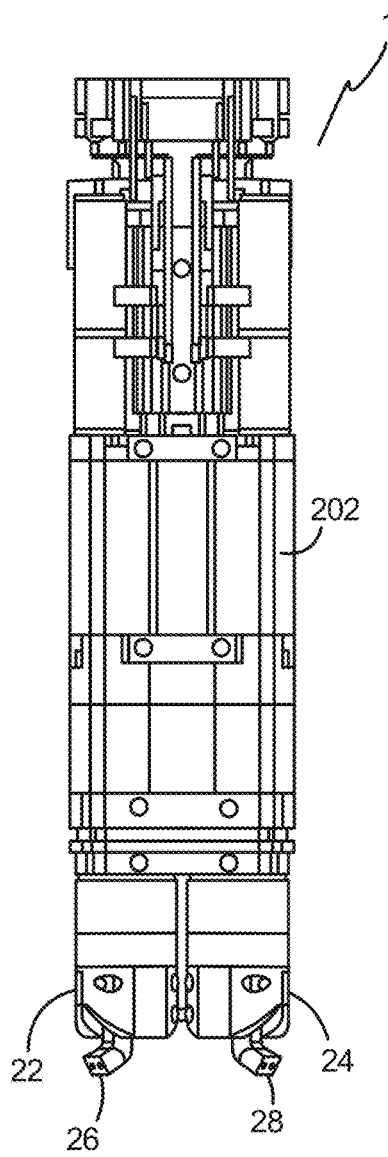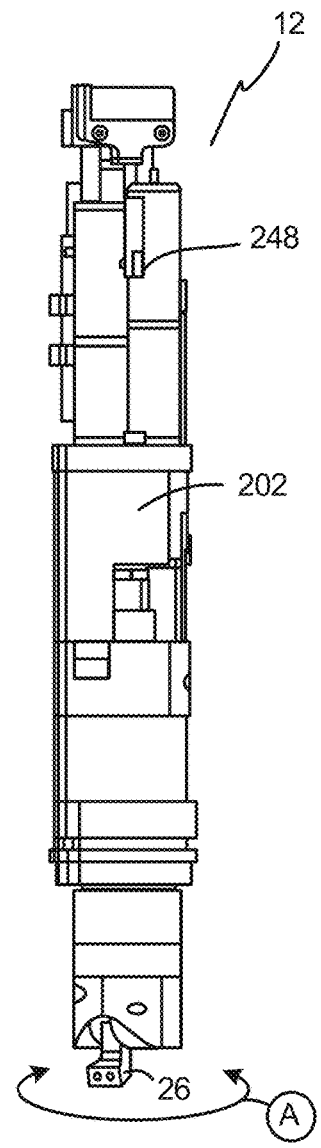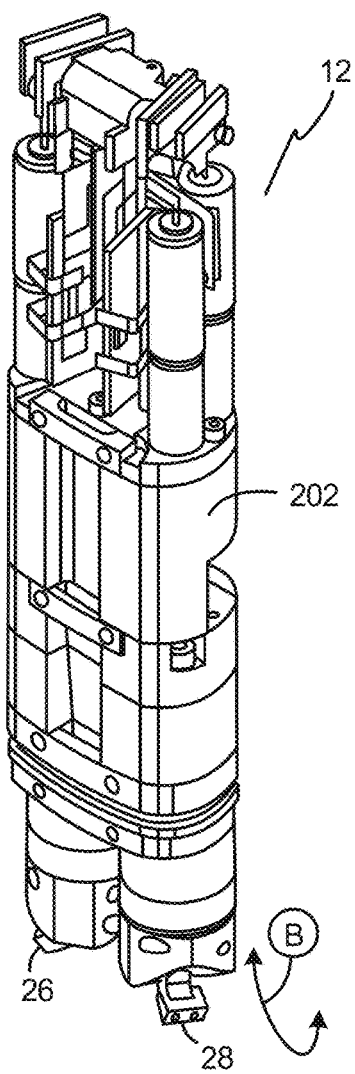
FIG. 8A  FIG. 8B  FIG. 8C
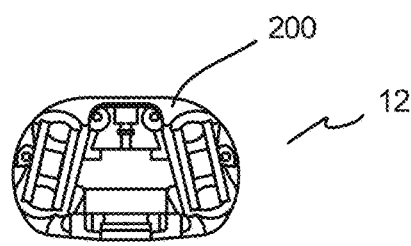
FIG. 8D

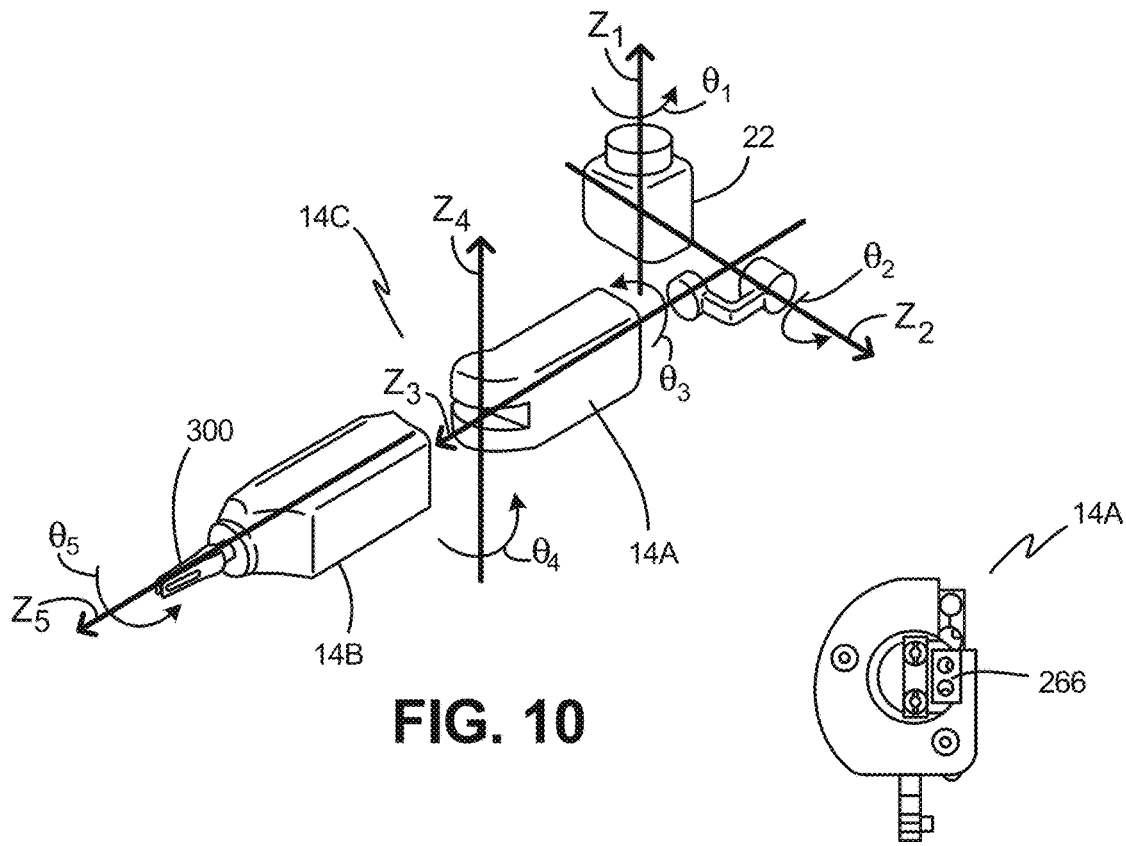
FIG. 10
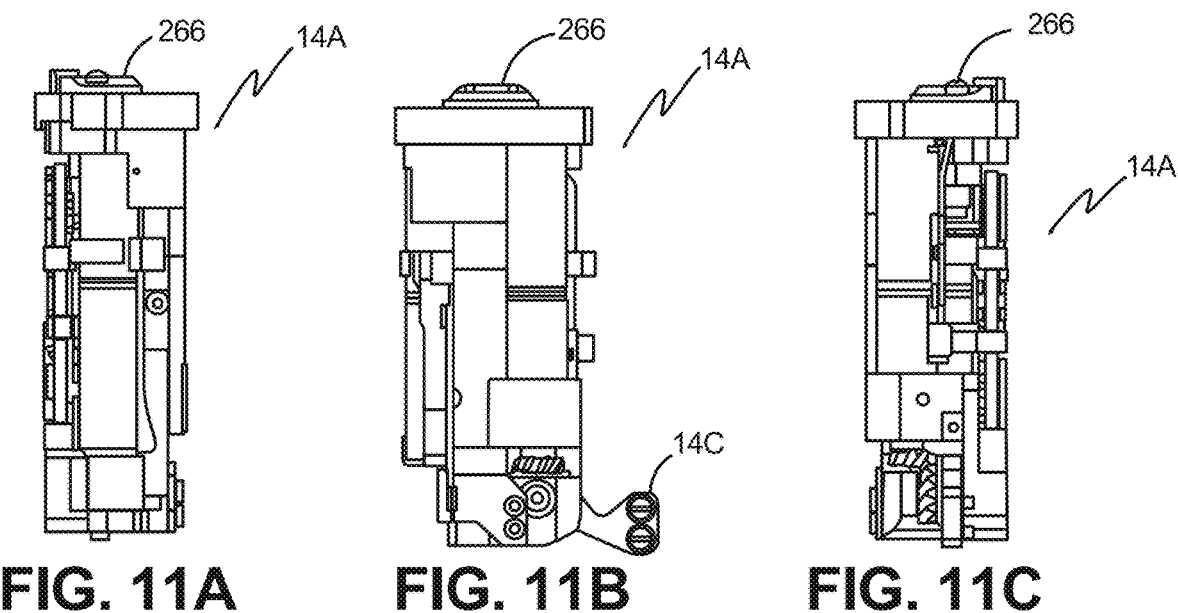
FIG. 11A  FIG. 11B  FIG. 11C

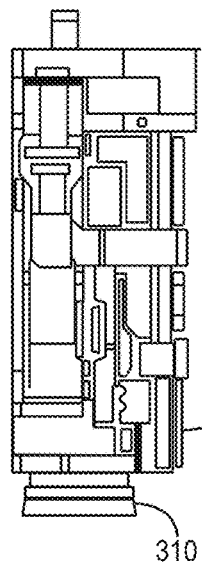 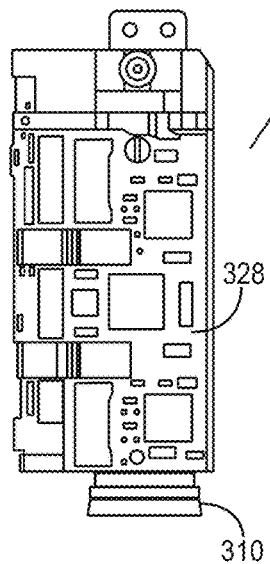 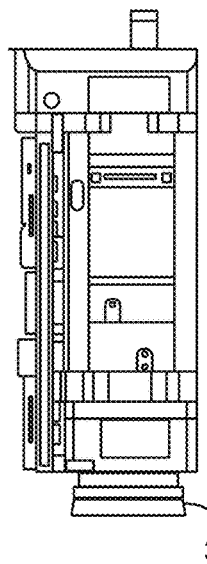
FIG. 13C  FIG. 13D  FIG. 13E
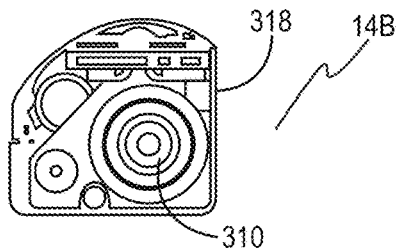
FIG. 13F
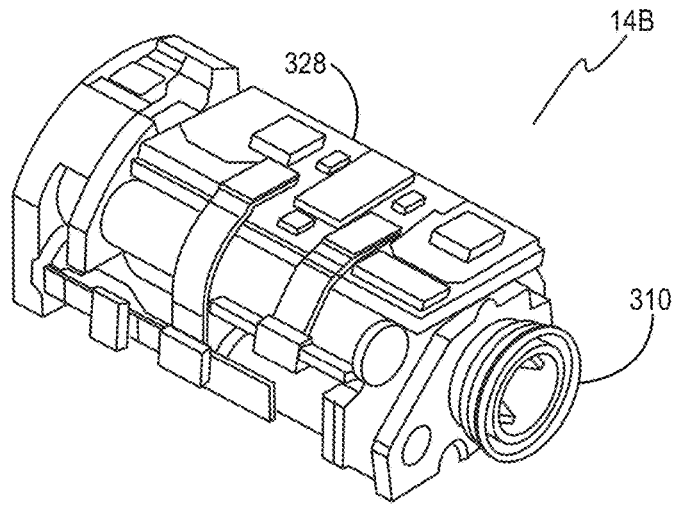
FIG. 13G

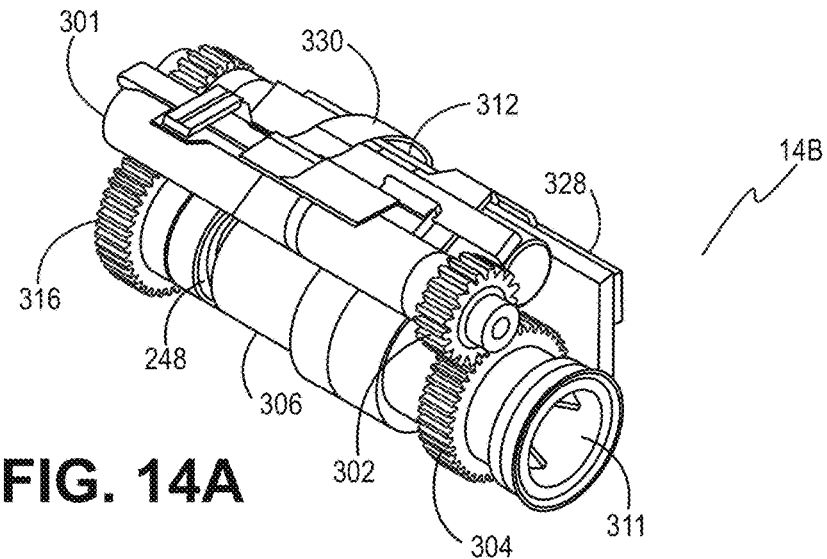
FIG. 14A
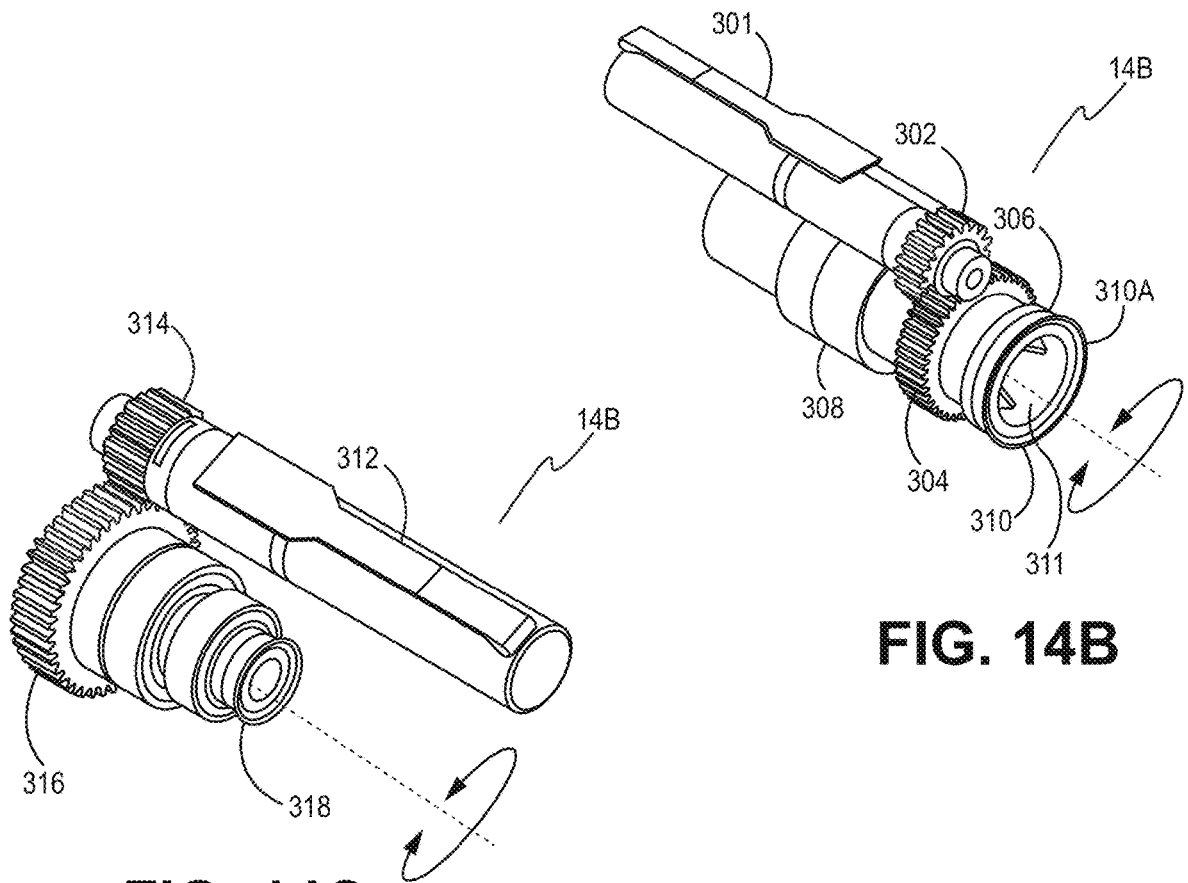
FIG. 14B
FIG. 14C

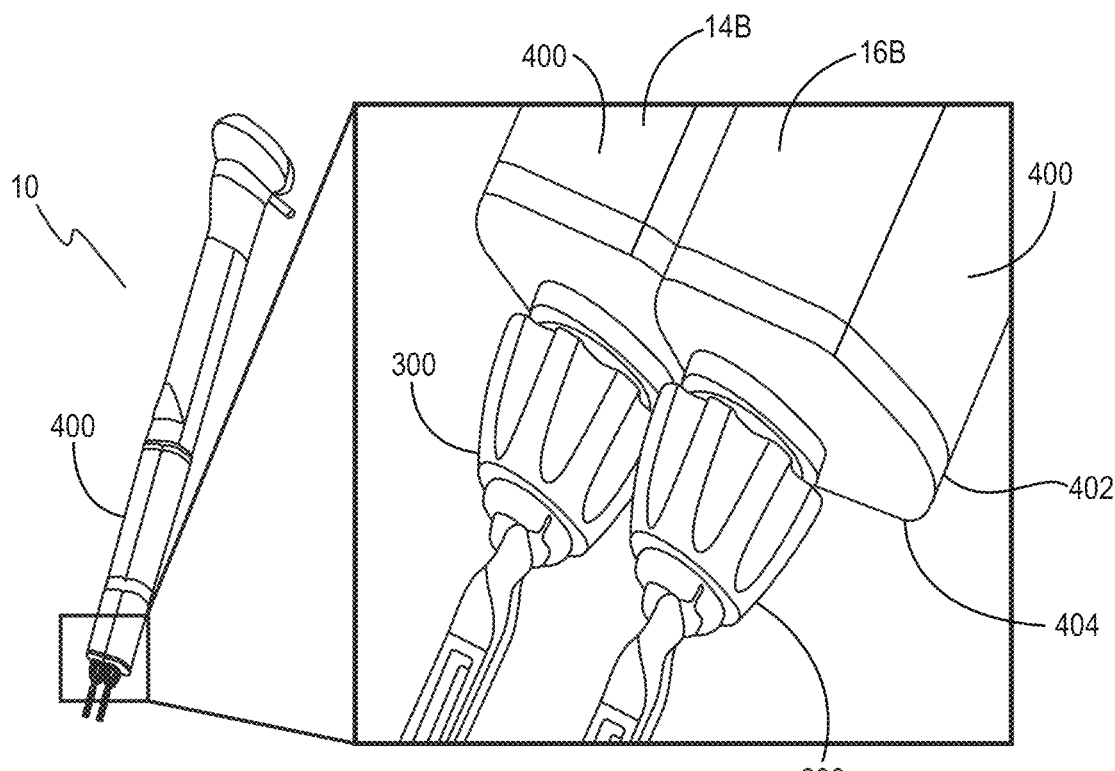
FIG. 18A
FIG. 18B
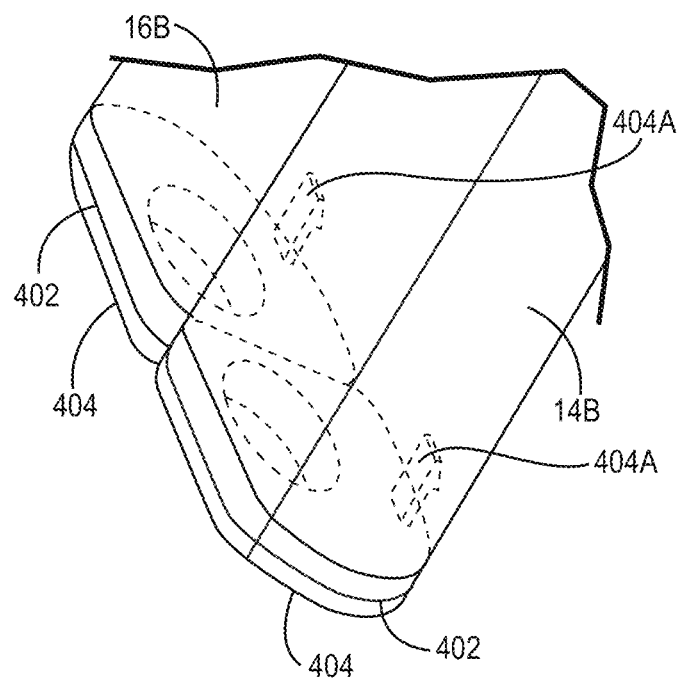
FIG. 18C

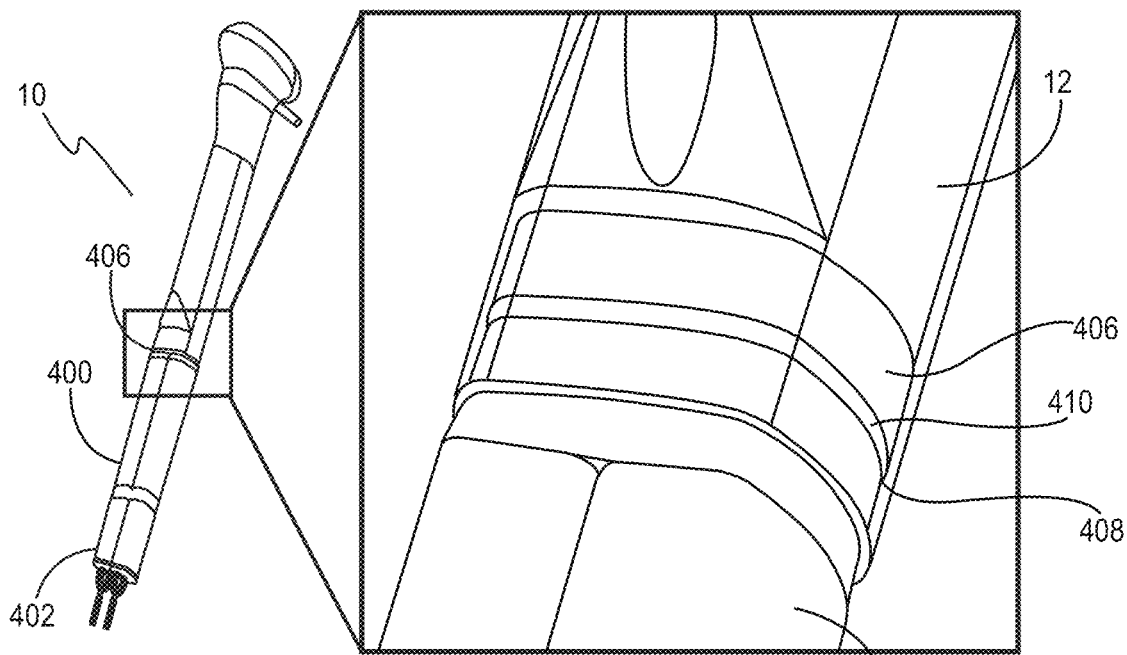
FIG. 19A  FIG. 19B
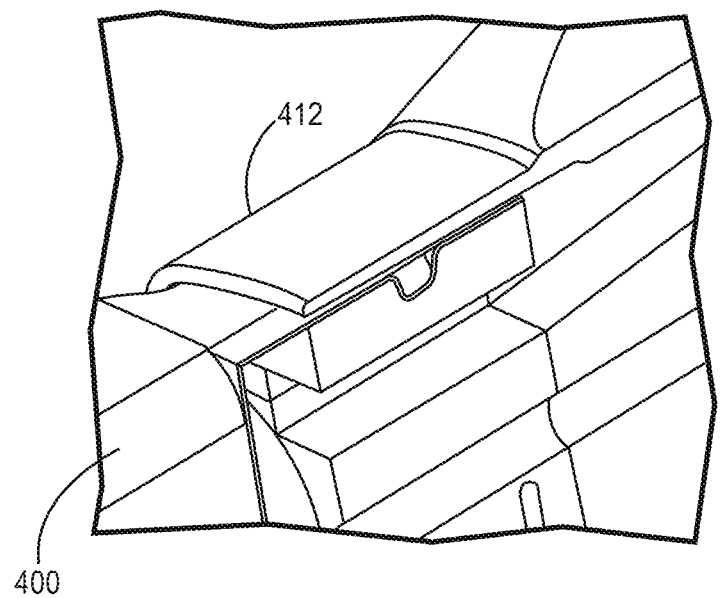
FIG. 19C

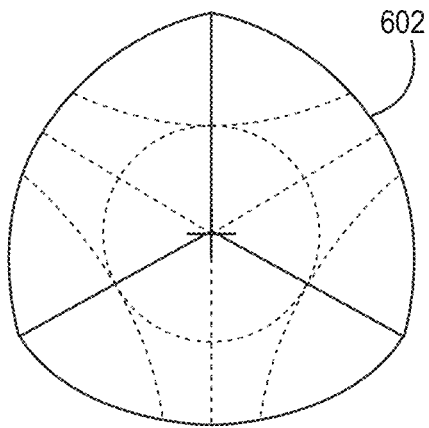
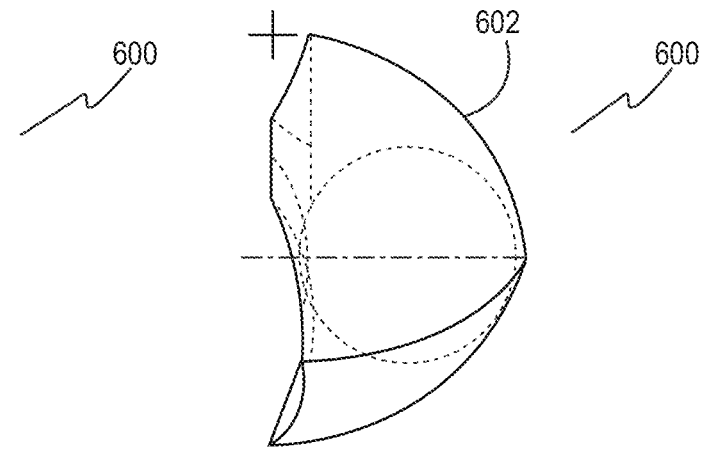
FIG. 29A
FIG. 29B
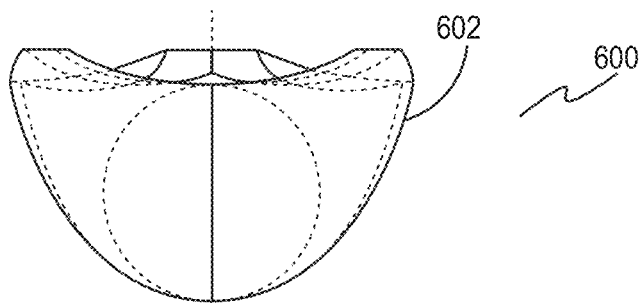
FIG. 29C
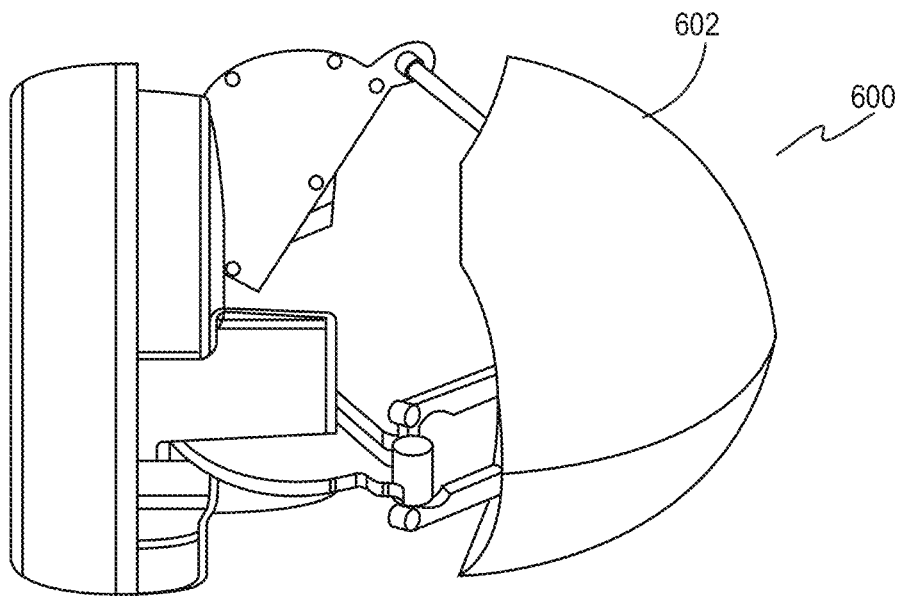
FIG. 29D

ROBOTIC SURGICAL DEVICES, SYSTEMS, AND RELATED METHODS

CROSS-REFERENCE TO RELATED APPLICATION(S)

This application claims priority as a continuation of U.S. patent application Ser. No. 15/227,813, filed Aug. 3, 2016 and entitled "Robotic Surgical Devices, Systems, and Related Methods," which claims the benefit under 35 U.S.C. § 119(e) to U.S. Provisional Application 62/200,563, filed Aug. 3, 2015 and entitled "Robotic Surgical Devices, Systems, and Related Methods," both of which are hereby incorporated herein by reference in their entireties.

FIELD OF THE INVENTION

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Other embodiments relate to various systems that have a robotic surgical device and a controller, wherein the device has one or more sensors and the controller has one or more motors such that the sensors transmit information that is used at the controller to actuate the motors to provide haptic feedback to a user.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various robotic surgical systems, including certain systems having camera lumens configured to receive various camera systems. Further embodiments relate to surgical insertion devices configured to be used to insert various surgical devices into a cavity of a patient while maintaining insufflations of the cavity.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one Example, a robotic surgical system, including a robotic surgical device including a device body including a distal end; a proximal end, and a camera lumen defined within the device body, the camera lumen including (1) a proximal lumen opening in the proximal end of the device body; (2) a socket portion defined distally of the proximal lumen opening, the socket portion including a first diameter and a first coupling component; (3) an extended portion defined distally of the socket portion, the extended portion having a second, smaller diameter; and (4) a distal lumen opening in the distal end of the device body, the distal lumen opening defined at a distal end of the extended portion; first and second shoulder joints operably coupled to the distal end of the device body; a first robotic arm operably coupled to the first shoulder joint; and a second robotic arm operably coupled to the second shoulder joint; and a camera component, including a handle including a distal end configured to be positionable within the socket portion; a second coupling component configured to releasably couple with the first coupling component, thereby releasably locking the handle into the socket portion; an elongate tube operably coupled to the handle, where the elongate tube is configured and sized to be positionable through the extended portion, the elongate tube including a rigid section; an optical section; and a flexible section operably coupling the optical section to the rigid section, where the elongate tube has a length such that at least the optical section is configured to extend distally from the distal lumen opening when the camera component is positioned through the camera lumen. Other embodiments of this aspect include corresponding computer systems, apparatus, and computer programs recorded on one or more computer storage devices, each configured to perform the actions of the methods.

Implementations may include one or more of the following features. The robotic surgical system where the camera lumen further includes a seal portion defined distally of the socket portion and proximally of the extended portion. The robotic surgical system where the seal section is configured to receive a ring seal and a one-way seal. The robotic surgical system where the seal section is further configured to receive a retention component, where the ring seal is retained within the ring-seal retention component. The robotic surgical system where the ring-seal retention component includes at least one protrusion extending from an outer wall of the ring-seal retention component. The robotic surgical system where the socket portion further includes a channel defined in an inner wall of the socket portion, where the channel is configured to receive the at least one protrusion. The robotic surgical system where the handle includes a controller configured to operate the camera component. The robotic surgical system where the distal lumen opening is positioned between the first and second shoulder joints. The robotic surgical system where the optical section is configured to be tiltable at the flexible section in relation to the rigid section, where the optical section has a straight configuration and a tilted configuration. The robotic surgical system where the elongate tube is configured to be rotatable in relation to the handle. The robotic surgical system where the socket portion further includes an inner wall including a channel configured to receive an insertion device. The robotic surgical system where the camera lumen includes a proximal lumen opening in the proximal end of the device body; a socket portion defined distally of the proximal lumen opening, the socket portion including a first diameter and a first coupling component; an extended portion defined distally of the socket portion, the extended portion having a second, smaller diameter; and a distal lumen opening in the distal end of the device body, the distal lumen opening defined at a distal end of the extended portion. The robotic surgical system where the first robotic arm further includes a first arm upper arm; a first arm elbow joint; and a first arm lower arm, where the first arm upper arm is configured to be capable of roll, pitch and yaw relative to the first shoulder joint and the first arm lower arm is configured to be capable of yaw relative to the first arm upper arm by way of the first arm elbow joint. The surgical robotic system where the first robotic arm further includes at least one first arm actuator disposed within the first robotic arm. The robotic surgical system where the second robotic arm further includes a second arm upper arm; a second arm elbow joint; and a second arm lower arm, where the second arm upper arm is configured to be capable of roll, pitch and yaw relative to the second shoulder joint and the second arm lower arm is configured to be capable of yaw relative to the second arm upper arm by way of the second arm elbow joint. The surgical robotic system where the second robotic arm further includes at least one second arm actuator disposed within the second robotic arm. The surgical robotic system including a handle including a distal end configured to be positionable within the socket portion; and a second coupling component configured to releasably couple with the first coupling component, thereby releasably locking the handle into the socket portion. The surgical robotic system further including at least one PCB disposed within at least one of the first or second robotic arms and in operational communication with at least one of the first robotic arm and second robotic arm, where the PCB is configured to perform yaw and pitch functions. Implementations of the described techniques may include hardware, a method or process, or computer software on a computer-accessible medium.

In one Example, a robotic surgical system, including a robotic surgical device including a device body including a distal end; a proximal end, and a camera lumen defined within the device body; first and second shoulder joints operably coupled to the distal end of the device body; a first robotic arm operably coupled to the first shoulder joint; and a second robotic arm operably coupled to the second shoulder joint; and a camera component, including a handle including a distal end configured to be positionable within the socket portion; a second coupling component configured to releasably couple with the first coupling component, thereby releasably locking the handle into the socket portion; an elongate tube operably coupled to the handle, where the elongate tube is configured and sized to be positionable through the extended portion, the elongate tube including a rigid section; an optical section; and a flexible section operably coupling the optical section to the rigid section, where the elongate tube has a length such that at least the optical section is configured to extend distally from the distal lumen opening when the camera component is positioned through the camera lumen. Other embodiments of this aspect include corresponding computer systems, apparatus, and computer programs recorded on one or more computer storage devices, each configured to perform the actions of the methods.

Implementations may include one or more of the following features. The robotic surgical system where the camera lumen includes a proximal lumen opening in the proximal end of the device body; a socket portion defined distally of the proximal lumen opening, the socket portion including a first diameter and a first coupling component; an extended portion defined distally of the socket portion, the extended portion having a second, smaller diameter; and a distal lumen opening in the distal end of the device body, the distal lumen opening defined at a distal end of the extended portion. The robotic surgical system where the first robotic arm further includes a first arm upper arm; a first arm elbow joint; and a first arm lower arm, where the first arm upper arm is configured to be capable of roll, pitch and yaw relative to the first shoulder joint and the first arm lower arm is configured to be capable of yaw relative to the first arm upper arm by way of the first arm elbow joint. The surgical robotic system where the first robotic arm further includes at least one first arm actuator disposed within the first robotic arm. The robotic surgical system where the second robotic arm further includes a second arm upper arm; a second arm elbow joint; and a second arm lower arm, where the second arm upper arm is configured to be capable of roll, pitch and yaw relative to the second shoulder joint and the second arm lower arm is configured to be capable of yaw relative to the second arm upper arm by way of the second arm elbow joint. The surgical robotic system where the second robotic arm further includes at least one second arm actuator disposed within the second robotic arm. The surgical robotic system including a handle including a distal end configured to be positionable within the socket portion; and a second coupling component configured to releasably couple with the first coupling component, thereby releasably locking the handle into the socket portion. The surgical robotic system further including at least one PCB disposed within at least one of the first or second robotic arms and in operational communication with at least one of the first robotic arm and second robotic arm, where the PCB is configured to perform yaw and pitch functions. Implementations of the described techniques may include hardware, a method or process, or computer software on a computer-accessible medium.

In one Example, a robotic surgical system, including a robotic surgical device including a device body including a distal end; a proximal end, and a camera lumen defined within the device body, the camera lumen including (1) a proximal lumen opening in the proximal end of the device body; (2) a socket portion defined distally of the proximal lumen opening, the socket portion including a first diameter and a first coupling component; (3) an extended portion defined distally of the socket portion, the extended portion having a second, smaller diameter; and (4) a distal lumen opening in the distal end of the device body, the distal lumen opening defined at a distal end of the extended portion; first and second shoulder joints operably coupled to the distal end of the device body; a first robotic arm operably coupled to the first shoulder joint; and a second robotic arm operably coupled to the second shoulder joint; and a camera component, including an elongate tube operably coupled to the handle, where the elongate tube is configured and sized to be positionable through the extended portion, the elongate tube including a rigid section; an optical section; and a flexible section operably coupling the optical section to the rigid section, where the elongate tube has a length such that at least the optical section is configured to extend distally from the distal lumen opening when the camera component is positioned through the camera lumen. Other embodiments of this aspect include corresponding computer systems, apparatus, and computer programs recorded on one or more computer storage devices, each configured to perform the actions of the methods.

Implementations may include one or more of the following features. The surgical robotic system including a handle including a distal end configured to be positionable within the socket portion; and a second coupling component configured to releasably couple with the first coupling component, thereby releasably locking the handle into the socket portion. The surgical robotic system further including at least one PCB disposed within at least one of the first or second robotic arms and in operational communication with at least one of the first robotic arm and second robotic arm, where the PCB is configured to perform yaw and pitch functions. Implementations of the described techniques may include hardware, a method or process, or computer software on a computer-accessible medium.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2A is a perspective view of the proximal end of a robotic surgical device according to one embodiment.

FIG. 2B is a rotated perspective view of the device of FIG. 2A.

FIG. 2C is a cutaway view of the proximal end of the device of FIG. 2A.

FIG. 3A is a perspective front view of a seal insertion component according to one embodiment.

FIG. 3B is a close-up view of the distal end of the insertion component of FIG. 3A without seals.

FIG. 3C is a close-up view of the distal end of the insertion component of FIG. 3A showing the O-ring carrier.

FIG. 3D is a perspective view of the insertion component of FIG. 3A above a robotic device body.

FIG. 3E is a perspective cutaway view of the embodiment of FIG. 3D.

FIG. 4E is an end view of a camera component showing the internal components, according to one embodiment.

FIG. 4F is a front view of the embodiment of FIG. 4E, in an "up" configuration.

FIG. 4G is a side view of the embodiment of FIG. 4A, in an "up" configuration.

FIG. 4H is a three-quarters rotated view of the embodiment of FIG. 4G.

FIG. 5A is a cutaway side view of the proximal end of a camera component inserted into a robotic surgical device according to one embodiment.

FIG. 5B is a further close-up cutaway side view of the embodiment of FIG. 5A.

FIG. 6B is a perspective internal view of the internal components of a camera component according to one embodiment.

FIG. 6C is a side internal view of the internal components of a camera component according to the embodiment of FIG. 6B.

FIG. 8A is an internal front view of the device body without a housing, according to one embodiment.

FIG. 8B is a side view of the embodiment of FIG. 8A.

FIG. 8C is a perspective view of the embodiment of FIG. 8A.

FIG. 8D is an end view of the embodiment of FIG. 8A.

FIG. 10 is a perspective view of a robotic arm having six degrees of freedom according to one embodiment.

FIG. 11A is a side view of an upper robotic arm without its housing according to one embodiment.

FIG. 11B is a rotated side view of the embodiment of FIG. 11A.

FIG. 11C is yet another rotated side view of the embodiment of FIG. 11A.

FIG. 11D is an end view of the embodiment of FIG. 11A.

FIG. 13C is a side view of a lower robotic arm without its housing according to one embodiment.

FIG. 13D is a rotated side view of the embodiment of FIG. 13C.

FIG. 13E is yet another rotated side view of the embodiment of FIG. 13C.

FIG. 13F is an end view of the embodiment of FIG. 13C.

FIG. 13G is a perspective view of the embodiment of FIG. 13C.

FIG. 14A is another internal view of the components of a lower robotic arm according to one embodiment.

FIG. 14B is a perspective view of certain roll components of the embodiment of FIG. 14A.

FIG. 14C is a perspective view of certain end effector interaction coupling components of the embodiment of FIG. 14A.

FIG. 18A is a perspective view of one implementation of the device within a sleeve, according to one embodiment.

FIG. 18B is an up-close view of the implementation of FIG. 18A.

FIG. 18C is a rotated up-close view of the implementation of FIG. 18A, without the end effectors shown.

FIG. 19A is a perspective view of one implementation of the device within a sleeve, according to another embodiment.

FIG. 19B is an up-close view of the implementation of FIG. 19A.

FIG. 19C is a rotated, cross-sectional up-close view of the implementation of FIG. 19A.

FIG. 29A is an end view of the hand controller limits in the haptic feedback system, according to on implementation.

FIG. 29B is a side view of the limits of FIG. 29A.

FIG. 29C is a top view of the limits of FIG. 29A.

FIG. 29D is a side view of the limits of FIG. 29A, showing the system disposed within those limits.

FIG. 30B is a cutaway view of the hand controller of FIG. 30A.

DETAILED DESCRIPTION

Figure 1A:
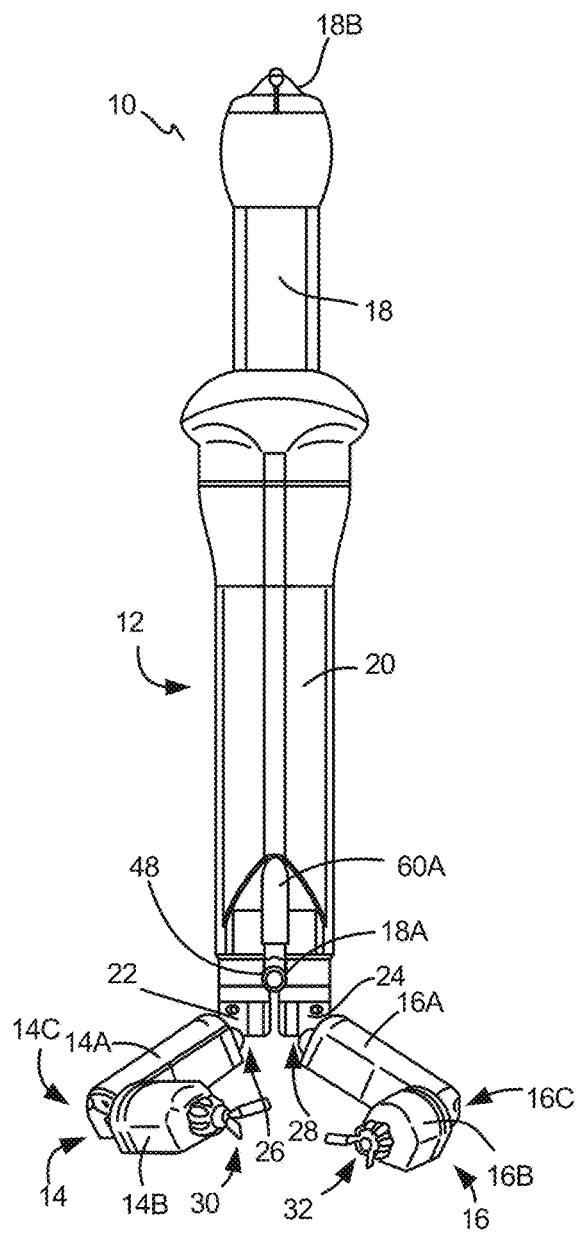
FIG. 1A is a front view of a robotic surgical device according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. patent application Ser. No. 14/617,232 (filed on Feb. 9, 2015 and entitled "Robotic Surgical Devices and Related Methods"), U.S. patent application Ser. No. 11/966,741 (filed on Dec. 28, 2007 and entitled "Methods, Systems, and Devices for Surgical Visualization and Device Manipulation"), U.S. Patent Application 61/030,588 (filed on Feb. 22, 2008), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. patent application Ser. No. 14/454,035 (filed Aug. 7, 2014 and entitled "Methods and Systems of Actuation in Robotic Devices"), U.S. patent application Ser. No. 12/192,663 (filed Aug. 15, 2008 and entitled Medical Inflation, Attachment, and Delivery Devices and Related Methods"), U.S. patent application Ser. No. 15/018,530 (filed Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. patent application Ser. No. 14/936,234 (filed on Nov. 9, 2015 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. patent application Ser. No. 14/745,487 (filed on Jun. 22, 2015 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. patent application Ser. No. 14/800,423 (filed on Jul. 15, 2015 and entitled "Robotic Surgical Devices, Systems, and Related Methods"), U.S. patent application Ser. No. 13/573,849 (filed Oct. 9, 2012 and entitled "Robotic Surgical Devices, Systems, and Related Methods"), U.S. patent application Ser. No. 13/738,706 (filed Jan. 10, 2013 and entitled "Methods, Systems, and Devices for Surgical Access and Insertion"), U.S. patent application Ser. No. 13/833,605 (filed Mar. 15, 2013 and entitled "Robotic Surgical Devices, Systems, and Related Methods"), U.S. patent application Ser. No. 14/661,465 (filed Mar. 18, 2015 and entitled "Methods, Systems, and Devices for Surgical Access and Insertion"), Ser. No. 13/839,422 (filed Mar. 15, 2013 and entitled "Single Site Robotic Devices and Related Systems and Methods"), U.S. Pat. No. 9,010,214 (issued on Apr. 21, 2015 and entitled "Local Control Robotic Surgical Devices and Related Methods"), U.S. patent application Ser. No. 14/656,109 (filed on Mar. 12, 2015 and entitled "Local Control Robotic Surgical Devices and Related Methods"), U.S. patent application Ser. No. 14/208,515 (filed Mar. 13, 2014 and entitled "Methods, Systems, and Devices Relating to Robotic Surgical Devices, End Effectors, and Controllers"), U.S. patent application Ser. No. 14/210,934 (filed Mar. 14, 2014 and entitled "Methods, Systems, and Devices Relating to Force Control Surgical Systems), U.S. patent application Ser. No. 14/212,686 (filed Mar. 14, 2014 and entitled "Robotic Surgical Devices, Systems, and Related Methods"), U.S. patent application Ser. No. 14/334,383 (filed Jul. 17, 2014 and entitled "Robotic Surgical Devices, Systems, and Related Methods"), U.S. patent application Ser. No. 14/853,477 (filed Sep. 14, 2015 and entitled "Quick-Release End Effectors and Related Systems and Methods"), U.S. patent application Ser. No. 14/938,667 (filed Nov. 11, 2015 and entitled "Robotic Device with Compact Joint Design and Related Systems and Methods"), and U.S. Patent Application 62/338,375 (filed May 18, 2016 and entitled "Robotic Surgical Devices, Systems, and Related Methods"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

Certain embodiments disclosed or contemplated herein can be used for colon resection, a surgical procedure performed to treat patients with lower gastrointestinal diseases such as diverticulitis, Crohn's disease, inflammatory bowel disease and colon cancer. Approximately two-thirds of known colon resection procedures are performed via a completely open surgical procedure involving an 8- to 12-inch incision and up to six weeks of recovery time. Because of the complicated nature of the procedure, existing robot-assisted surgical devices are rarely used for colon resection surgeries, and manual laparoscopic approaches are only used in one-third of cases. In contrast, the various implementations disclosed herein can be used in a minimally invasive approach to a variety of procedures that are typically performed 'open' by known technologies, with the potential to improve clinical outcomes and health care costs. Further, the various implementations disclosed herein can be used for any laparoscopic surgical procedure in place of the known mainframe-like laparoscopic surgical robots that reach into the body from outside the patient. That is, the less-invasive robotic systems, methods, and devices disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various embodiments herein could enable a minimally invasive approach to procedures performed in open surgery today.

As shown in FIGS. 1A-1G, certain exemplary embodiments relate to a device 10 having a body 12 with two arms 14, 16 operably coupled thereto and a camera component 18 positionable therein. That is, device 10 has a first (or "right") arm 14 and a second (or "left) arm 16, both of which are operably coupled to the body 12 as discussed in additional detail below. The body 12 as shown has a casing (also referred to as a "cover" or "enclosure") 20. The body 12 is also referred to as a "device body" 20 and has two rotatable cylindrical components (also referred to as "housings" and "turrets"): a first (or "right") housing 22 and a second (or "left") housing 24. Each arm 14, 16 also has an upper arm (also referred to herein as an "inner arm," "inner arm assembly," "inner link," "inner link assembly," "upper arm assembly," "first link," or "first link assembly") 14A, 16A, and a forearm (also referred to herein as an "outer arm," "outer arm assembly," "outer link," "outer link assembly," "forearm assembly," "second link," or "second link assembly") 14B, 16B. The right upper arm 14A is operably coupled to the right housing 22 of the body 12 at the right shoulder joint 26 and the left upper arm 16A is operably coupled to the left housing 24 of the body 12 at the left shoulder joint 28. Further, for each arm 14, 16, the forearm 14B, 16B is rotatably coupled to the upper arm 14A, 16A at the elbow joint 14C, 16C.

In the exemplary implementation as shown, each of the arms 14, 16 also has an end effector 30, 32 operably coupled to the distal end of the forearm 14B, 16B. An end effector can also be referred to herein as an "operational component," and various embodiments will be discussed herein below in further detail.

In one implementation, each of the arms 14, 16 has six degrees of freedom. That is, as explained in further detail below, each arm 14, 16 has three degrees of freedom at the shoulder joint 26, 28, one degree of freedom at the elbow joint 14C, 16C, and two degrees of freedom at the end effector 30, 32 (which can be, in certain embodiments, rotated—end effector roll—and opened/closed). As such, the six degrees of freedom of each arm 14, 16 are analogous to the degrees of freedom of a human arm, which also has three degrees of freedom at the shoulder and one at the elbow. One advantage of an arm having four degrees of freedom (with an end effector having two degrees of freedom) is that the end effector can have multiple orientations at the same Cartesian point. This added dexterity allows the surgeon or other user more freedom and a more intuitive sense of control while operating the device.

Figure 1B:
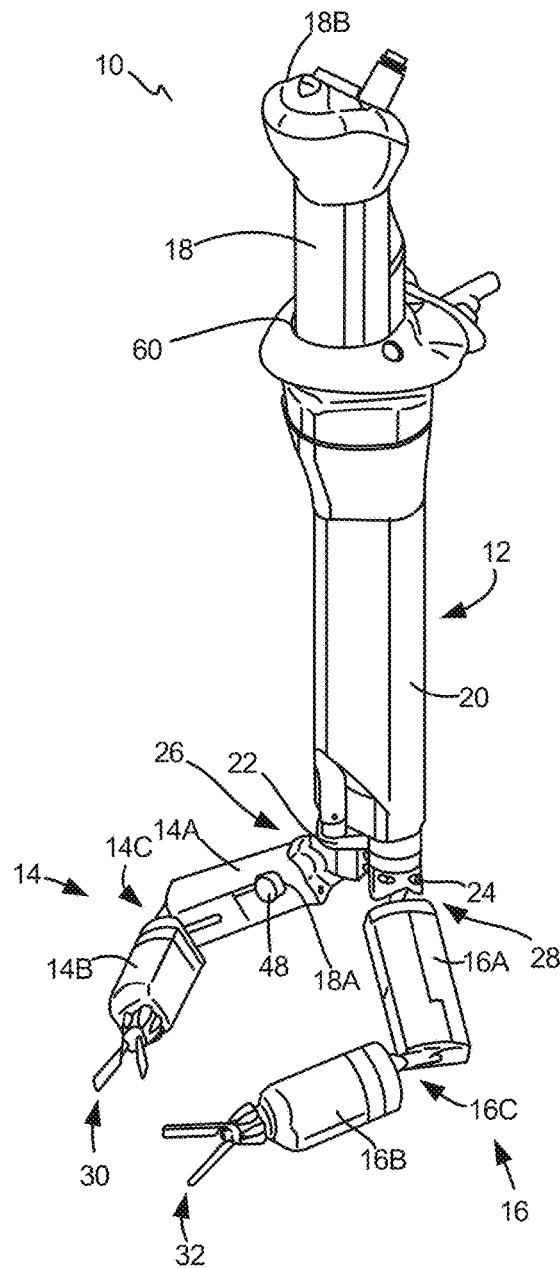
FIG. 1B is perspective front view of the device of FIG. 1A.
Figure 1C:
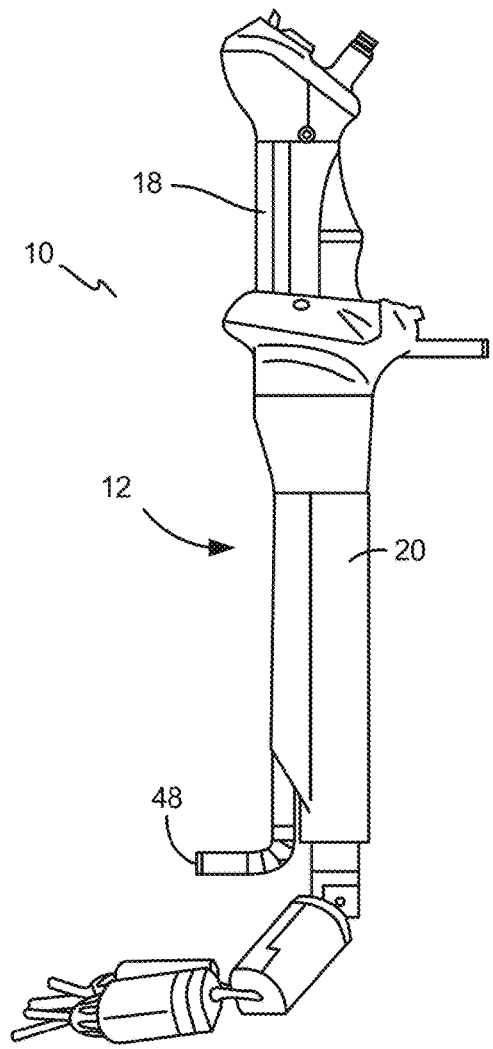
FIG. 1O is a side view of the device of FIG. 1A.
FIG. 1D is an end view of the device of FIG. 1A.
FIG. 1E is a further front view of the device of FIG. 1A, without the camera component.
FIG. 1F is a further side view of the device of FIG. 1A, without the camera component.
FIG. 1G is a front view of the camera component, according to the embodiment of FIG. 1A.
Figure 1D:
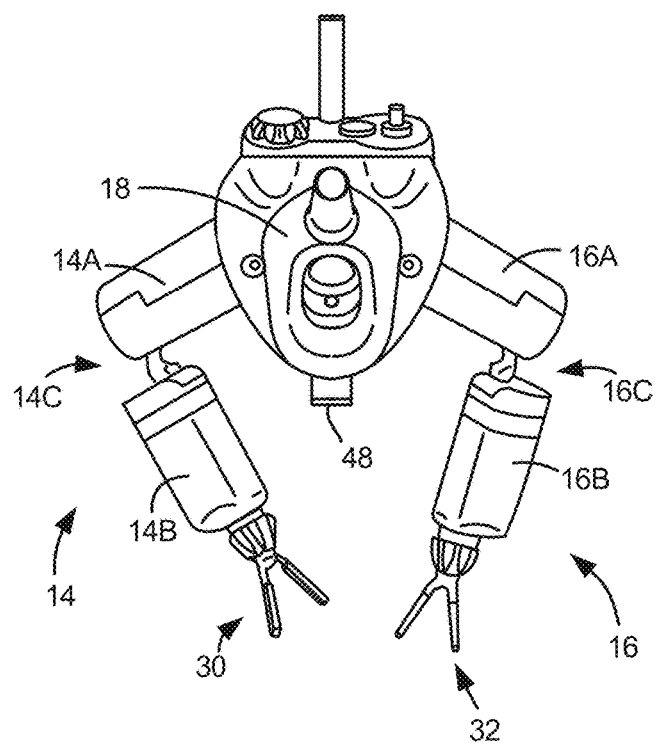
Figure 1E:
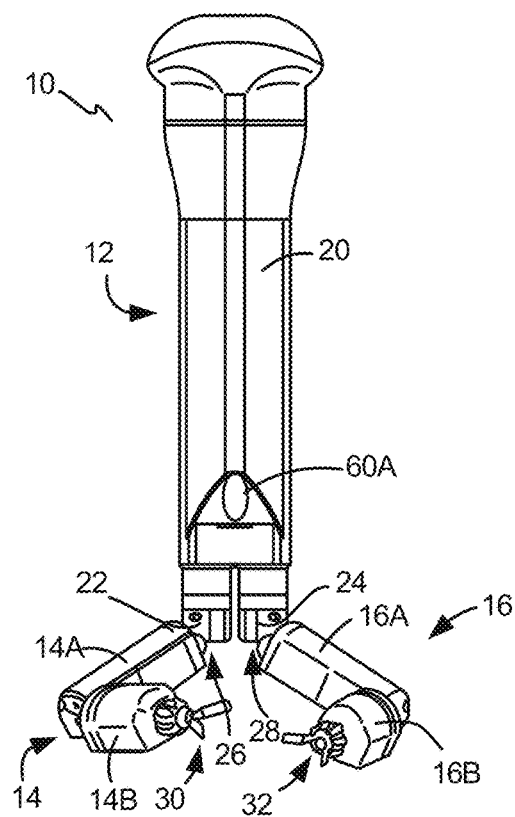
Figure 1F:
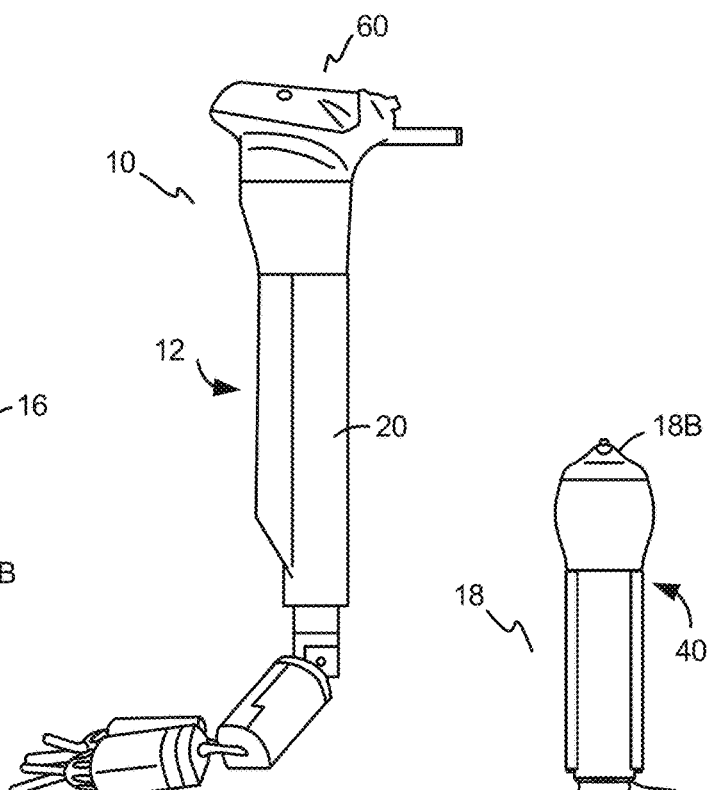
Figure 1G:
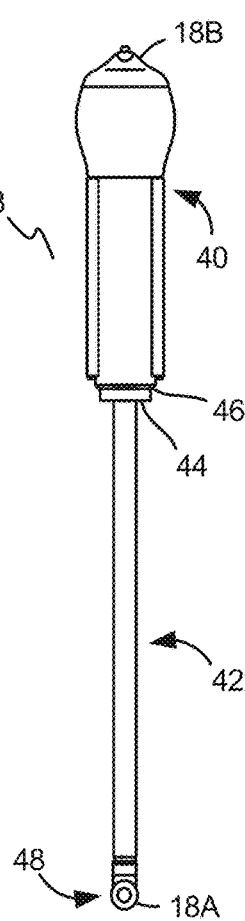

The camera component 18, as shown in FIG. 1G in accordance with one embodiment, is easily insertable into and removable from the body 12. As shown, the camera component 18 has a handle 40, a camera body or tube 42, a distal tube end 18A having a camera lens 48, and two shoulders 44, 46 defined at the distal end of the handle 40. That is, the first shoulder 44 has a first diameter and the second shoulder 46 has a second diameter that is larger than the first diameter.

According to one embodiment, FIGS. 2A, 2B, and 2C depict the proximal end of the device body 12 having sealed electrical connections or connectors 50, 52, a support rod 54, a latch 56 and a head 58 with an opening 60 defined in the body 12. As discussed in relation to FIGS. 25A-C herein, in these implementations, the support rod is configured to be attached to the support arm to dispose the device for use.

In various implementations, the electrical connectors 50, 52 can provide robot power and bus communications required for robot functionality, including power and communications connectors, bipolar cautery connectors and monopolar cautery connectors, such as LEMO® push-pull circular connectors. In certain implementations, three connectors can be provided. In the implementation of FIGS.

2A-C, the first electrical connector 50 is configured to send and receive robot power and bus communications and the second electrical connector 52 is configured for combined cautary mono- and bi-polar connectivity. Alternatively, the three connectors may be combined into a single integrate custom connector, In yet a further alternative, and as shown in FIGS. 3D-F, a single cable 53 integrated directly into the robot can be provided. It is understood that a sealed, strain relieved cable egress location would then exist in this location instead of the connectors 50, 52.

According to these implementations, the opening 60 is in fluid communication with a lumen 62 that is defined through the length of the body 12. The lumen 62 is configured to receive the camera component 18 and has a receiving portion (also referred to herein as a "socket portion" or "socket") 62A, a seal portion 62B, and an extended portion 62C.

In certain implementations, the socket portion 62A is configured to be "tight fitting," that is, it is configured to mate with the camera component 18 handle 40 to react or resist all loads or prevent all rotational and translational motion. In various implementations, the latch 56 is disposed within the socket portion 62A so as to be capable of coupling to the clasping portion 72 of the camera component 18.

In various implementations, a seal or seals 63A, 63B are provided in the seal portion 62B, so as to maintain a fluidic seal around the camera 18 as it is disposed in the lumen 62. The seal portion 62B is distal in relation to the receiving portion 62A and is configured to house a seal or seals 63A, 63B against the wall 68 of the lumen 62, as is described in relation to FIGS. 2C-3F.

In the implementation depicted in FIGS. 2C and 3A-F, the device utilizes a first seal 63A that is a one-way duckbill seal, though it is understood that various other one-way seals can be used in alternate embodiments. In these implementations, a second seal 63B—which can be an O-ring carrier seal—is also disposed proximally to the first seal 63A. As shown in FIGS. 3A and 3C-F, in various implementations, the O-ring carrier seal 63B comprises an O-ring 65 configured to urge the first seal 63A distally. It is understood that in various implementations, the O-ring can provide a seal against the camera component 18, while the O-ring carrier seal 63A can provide a seal against the lumen 62A against the escape of gasses or fluids as described herein.

As described below, in these implementations, when the seals are installed, the O-ring carrier seal 63B compresses on the lip 63A1 of the first seal 63A, thereby creating a seal against the inner wall of the housing (shown at 67). The use of first and second seals 63A, 63B in certain implementations provides certain advantages described herein. In situations when the camera component 18 is not present, the pressure from the abdominal cavity will cause the one-way duck bill seal 63A to close and prevent the loss of that pressure. In situations where the camera present, the camera and tube 42 will cause duck bill seal 63A to be open and allow passage into the lumen 62, while the O-ring 65 and O-ring carrier seal 63A will seal against the rigid camera tube 42 and lumen 62, respectively, to maintain cavity pressure. It is understood that further implementations are of course possible.

As shown in FIGS. 3A-F, in various implementations, an elongate insertion component 15 is provided, which allows the insertion and removal of the seal or seals 63A, 63B for replacement and/or cleaning. As is shown in FIGS. 3A-C, the insertion component 15 can have a seal coupling ring 13 with mounting projections 13A, 13B configured to mate to a seal such as the O-ring carrier seal 63B and maintain the rotational position of the seal while it is being disposed in the lumen 62. In various implementations, ridges 17 can also be provided to secure the seal in place. Returning to FIG. 2C, the distal end of the receiving portion 62A is defined by a shoulder 64 that is configured to receive the insertion component 15. At least one channel 66 is defined in a portion of the shoulder 64 and the lumen 62 as shown and is configured to receive a corresponding protrusion or protrusions 67A, 67B disposed on the O-ring carrier seal 63B such that the protrusion or protrusions 67A, 67B can be positioned in and slid along the channel 66, thereby allowing for the seals 63A, 63B to be place and locked into position in the lumen 62. The insertion component 15 can subsequently be removed, such that the seals 63A, 63B are contained within the lumen 62 for use.

More specifically, the channel 66 is defined in the lumen 62 with a longitudinal length 66A and a radial length 66B. In certain implementations, the channel 66 is tapered along the longitudinal length 66A. As such, a protrusion 67A is positioned in the longitudinal length 66A and the insertion component 15 is advanced distally until the protrusion 67A reaches the end of the longitudinal length 66A. At this point, the insertion component 15 can be rotated around its longitudinal axis such that the protrusion 67A is advanced along the radial length 66B. As shown in FIG. 3B, the mounting projections 13A, 13B can prevent the rotation of the O-ring seal 63B relative to the insertion component 15 during this rotation. Further the rigid O-ring 65 provides sufficient distal force against the first seal 63A such that it is fixed into place as a result of this rotation and locking. The resulting coupling of the seals 63A, 63B within the lumen is a mechanical coupling that is sufficiently strong for a user to pass the camera component 18 through the seals 63A, 63B for use without dislodging the seals 63A, 63B.

FIGS. 4A-H depict an exemplary implementation of the camera component 18. The camera component 18 in this specific implementation is configured to be removably incorporated into a robotic device body 12, as is shown in FIGS. 1A-B. More specifically, the camera component 18 is configured to be removably positioned through the lumen 62 defined in the device body 12 such that the camera component 18 is inserted through the proximal opening 60, receiving portion into the receiving portion 62A, through the seal portion 62B and seal or seals 63A, 63B, and into the extended portion 62C such that a distal portion of the camera component 18A and camera lens 48 protrudes from the distal opening 60A (as best shown in FIG. 1A).

Figure 4A:
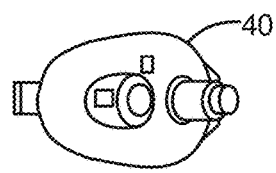
FIG. 4A is an end view of a camera component according to one embodiment.
Figure 4B:
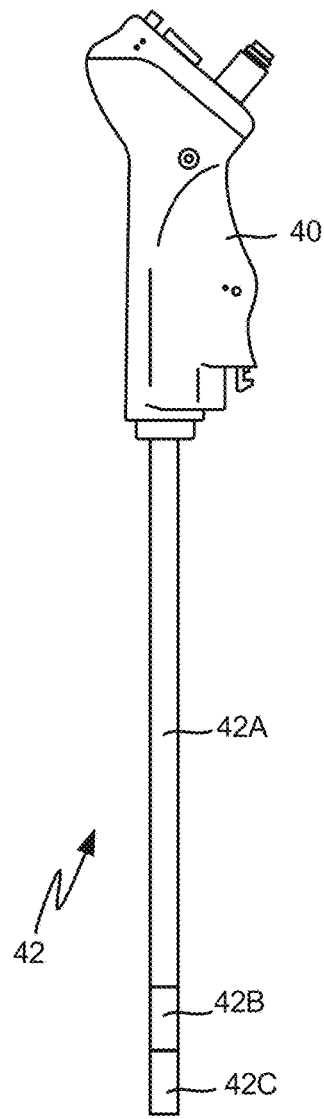
FIG. 4B is a side view of the embodiment of FIG. 4A, in a "down" configuration.
Figure 4C:
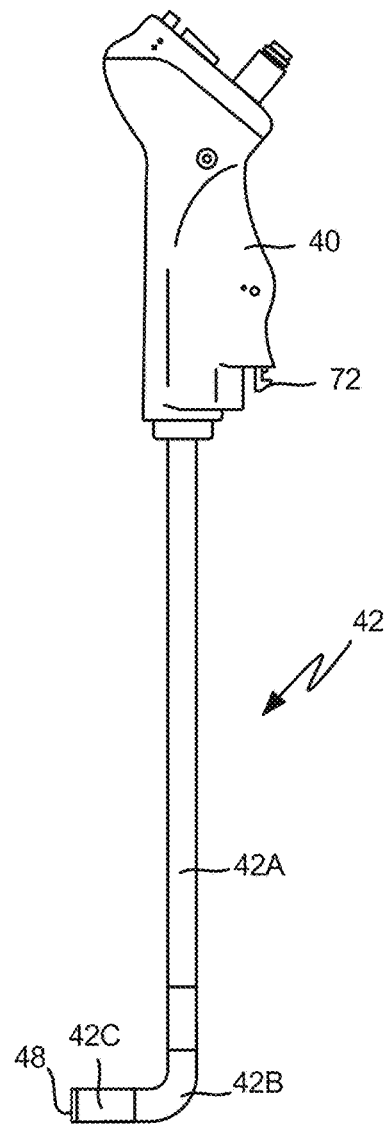
FIG. 4C is a side view of the embodiment of FIG. 4A, in an "up" configuration.
Figure 4D:
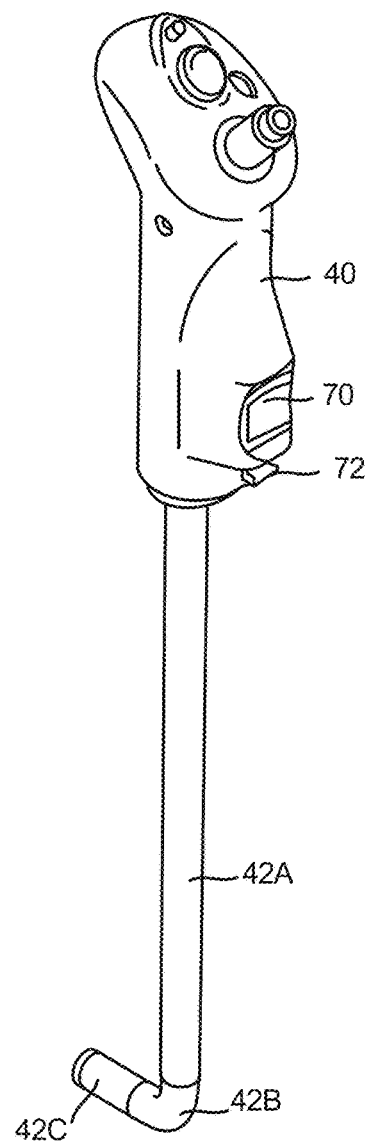
FIG. 4D is a three-quarters rotated view of the embodiment of FIG. 4C.

As shown in FIGS. 4A-H, this camera component 18 embodiment has a controller (also referred to as a "handle") 40 and an elongate component (also referred to herein as a "tube") 42 operably coupled at its proximal end to the handle 40. As best shown in FIG. 4C, the tube 42 has a rigid section 42A, a flexible section 42B, and an optical section 42C. As such, in these implementations the camera component has two degrees of freedom: pan (left and right rotation) and tilt, meaning looking "up and down" in the surgical workspace. Further discussion of these degrees of freedom can be found in relation to FIG. 10.

In one embodiment, the handle 40 is configured to contain local electronics for video transmission, along with actuators and associated mechanisms (as are best shown in relation to FIG. 4H) for actuating pan and tilt functionality of the tube 42. It is understood that the local electronics, actuators, and associated mechanisms can be known, standard components. In a further implementation, the handle 40 can also contain a light engine. Alternatively, the light engine can be a separate component, and a light cable can operably couple the light engine to the handle.

According to one implementation, the rigid section 42A of the tube 42 is substantially rigid and contains appropriate wires and optical fibers as necessary to operably couple to the optical component in the optical section 42C to the handle 40. The substantial rigidity of the rigid section 42A allows for easy manipulation of the tube 42, including easy insertion into the lumen 62.

The flexible section 42B, in accordance with one embodiment, is configured to allow for movement of the optical section 42C between a straight configuration in FIG. 4B and a tilted configuration as shown in FIG. 4C, or any position in between. The optical section 42C is substantially rigid, much like the rigid section 42A, and contains the optical element, along with appropriate local electronics.

Accordingly, various implementations of the camera component 18 of this implementation have two mechanical degrees of freedom: pan (look left/right) and tilt (look up/down). In use, the camera component 18 has pan and tilt functionality powered and controlled by the actuators and electronics in the handle 40. In various implementations, the handle 40 further comprises a button 70 and camera clasp 72 configured to mate with the latch 56, as is shown in further detail in FIGS. 5A-D.

The tilt functionality relates to tilting the optical section 42C such that the camera 48 is oriented into the desired workspace, as is discussed further in relation to FIGS. 24A-D. This tilting can be accomplished via a cable that is operably coupled to the flexible section 42B or the optical section 42C such that actuation of the cable causes the optical section 42C to tilt by bending the flexible section 42B as shown for example in FIG. 4C and FIGS. 7A-B. Alternatively this tilt function can be achieved by any other known mechanism or method for bending the tube 42 at the flexible section 42B.

As shown in the implementations of FIGS. 5A-7B, the camera component 18 houses several internal electrical and mechanical components capable of operation and movement of the camera 48, tube 42 and other operative components. In various implementations, the camera component 18 has a presence sensing system configured to detect the insertion of the component 18 into the lumen 62. Further, to prevent damage, in certain embodiments, the camera component 18 is configured to provide a "mechanical lockout," such that the camera component 18 cannot be removed unless the tube 42 is in the "straight" (tilt=0°) configuration.

As discussed above, FIGS. 5A-B depict an implementation of the device 10 where the camera component 18 has been inserted into the lumen 62 of the body 12. In these implementations, following the placement of the seals 63A, 63B in the seal portion 62B (as described in relation to FIGS. 3A-F), the camera component 18 can be inserted into the lumen 62 and the latch 56 engaged.

Figure 5C:
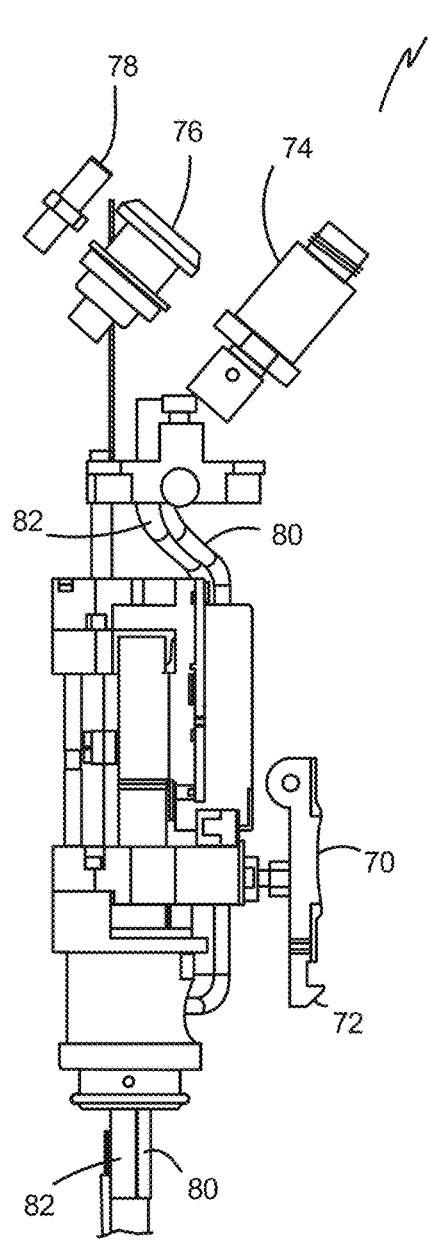
FIG. 5C is a side view of the internal components of a camera component according to one embodiment.

As shown in FIG. 5C, in certain implementations, the camera component 18 comprises a light guide post 74, an actuation connector 76 and/or a coax connector 78. In various implementations, the light guide post 74 facilitates the transference of light from an external light generator to the fiber optics in the camera. An actuation connector 76 can provide power and communications functions such as robotic and camera power and communications functions discussed below in relation to FIGS. 26-29D. In various implementations, the coax connector 78 can provide additional functionality, such as transmission of video signal, as is described herein in relation to FIGS. 7C and 26A. In various implementations, the fiber optic cable 80 is in operational and luminary communication with the light guide post and extends distally into the lumen (not shown). Further, a communications line 82 extends with the fiber optic cable 80 in these implementations, as is discussed further in relation to FIGS. 5E-F.

Figure 5D:
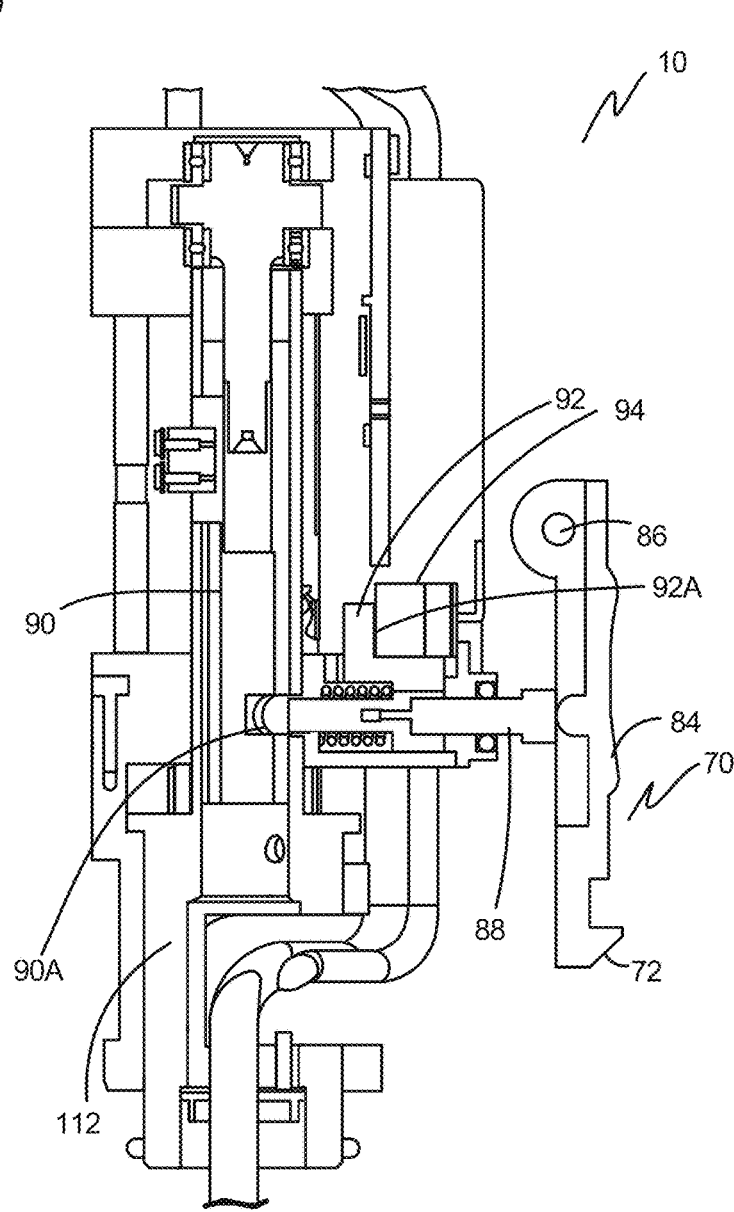
FIG. 5D is a further internal side view of the embodiment of FIG. 5C.
Figure 5E:
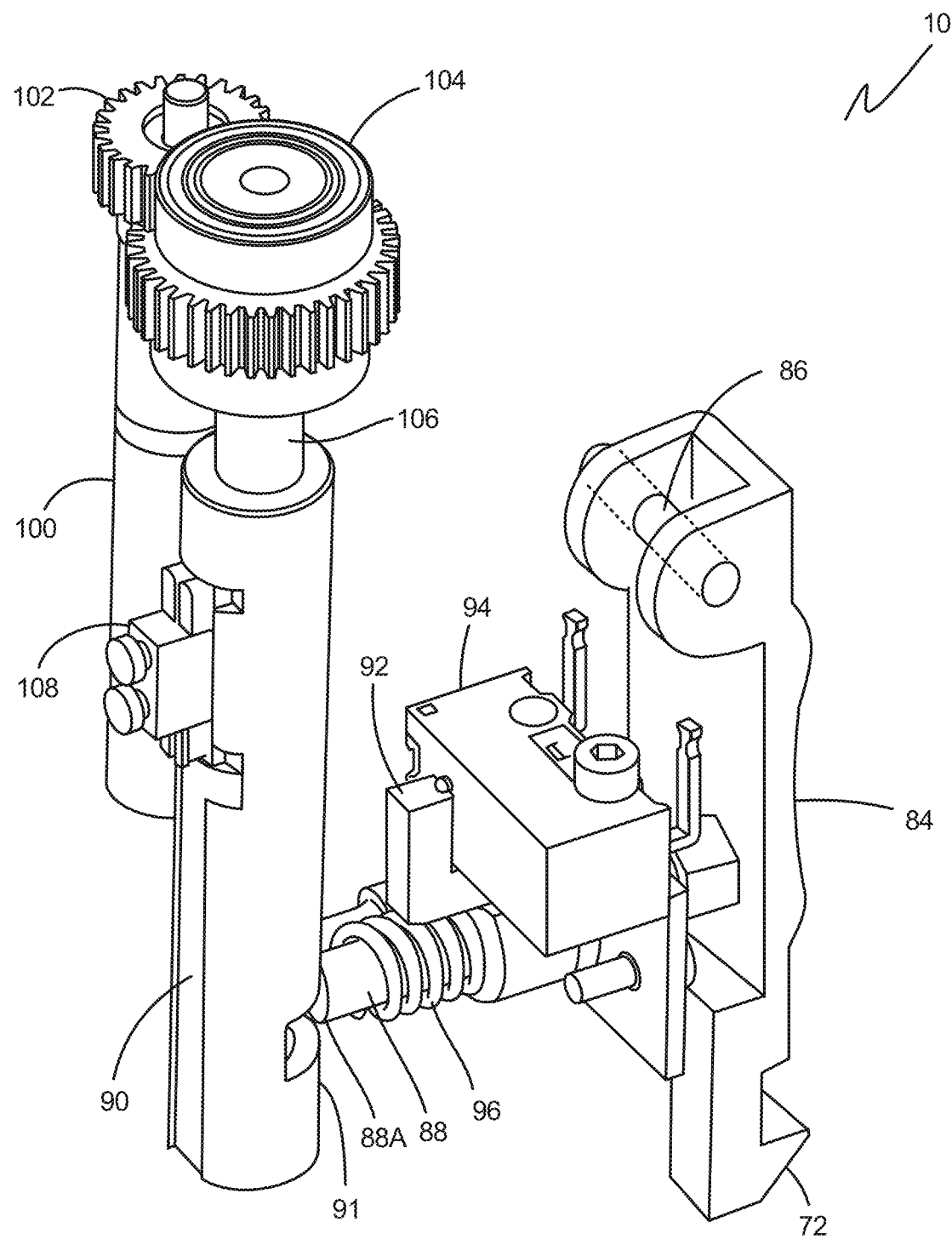
FIG. 5E is a perspective view of the embodiment of FIG. 5C.

The implementation of FIGS. 5C-E depicts one implementation of the camera component 18 having a mechanical lockout. In certain of these implementations, depressing the handle button 70 can activate the re-orientation of the tube 42 into the straight orientation, so as to allow for removal of the camera component when tilt=0°. In this implementation, the camera clasp 72 is disposed on a clasping member 84 which also comprises the button 70, such that depressing the button 70 results in the pivoting of the clasping member around a clasp pivot 86 that is rotationally coupled to the camera housing (not shown), such that a plunger 88 disposed adjacent to the clasping member so as to be capable of being urged inward in response to the actuation of the button 70.

In various implementations, the plunger 88 end 88A is aligned with a slot 90A in the lead screw nut 90, which is linearly translated in response to camera tilt, as is described in further detail below. In these implementations, slot 90A and plunger 88 alignment only occurs when the camera tube 42 is in the "straight" orientation. In these implementations, the plunger is also fixedly attached to a trigger arm 92, such that when the arm is displaced—even slightly—the arm triggers a limit switch 94, initiating a "go-straight" subroutine, thereby straightening the camera. It is understood that the length of plunger 88 in these implementations is such that it is unable to enter the slot 90A when the camera is tilted (as described below in relation to FIGS. 5E-6D, so that that clasp 72 will not disengage from the robot when slot 90A is not aligned.

It is understood that in certain implementations, the "go-straight" subroutine is triggered in response to the actuation of the button 70, regardless of whether the plunger end 88A enters the slot 90A. In these implementations, and as best shown in FIG. 5E, the space between the non-slotted portions (shown generally at 91) of the lead screw nut 90 and the plunger end 88A is less than the distance of the overlap between the clasp 72A and latch edges 56A (shown in FIG. 5B), thereby preventing unclasping. In these implementations, the distance between the trigger arm 92 and limit switch 94 is also less than the distance between the space between the non-slotted portions (shown generally at 91) of the lead screw nut 90 and the plunger end 88A, such that the limit switch 94 will be actuated in response to the actuation of the button 70 whether or not the plunger end 88A enters the slot 90A. In certain implmentations, an actuator spring 96 is operationally coupled to the plunger 88 to urge the plunger outward, thereby keeping the clasp 72 and button 70 tensioned when not in use.

Figure 5F:
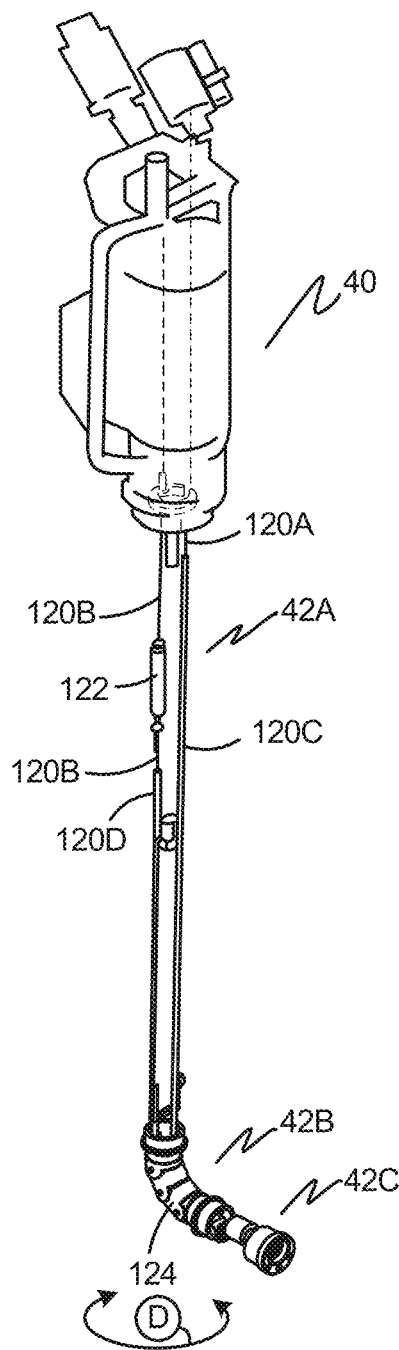
FIG. 5F is a perspective internal view of a camera component inserted into a robotic surgical device according to one embodiment.
Figure 5G:
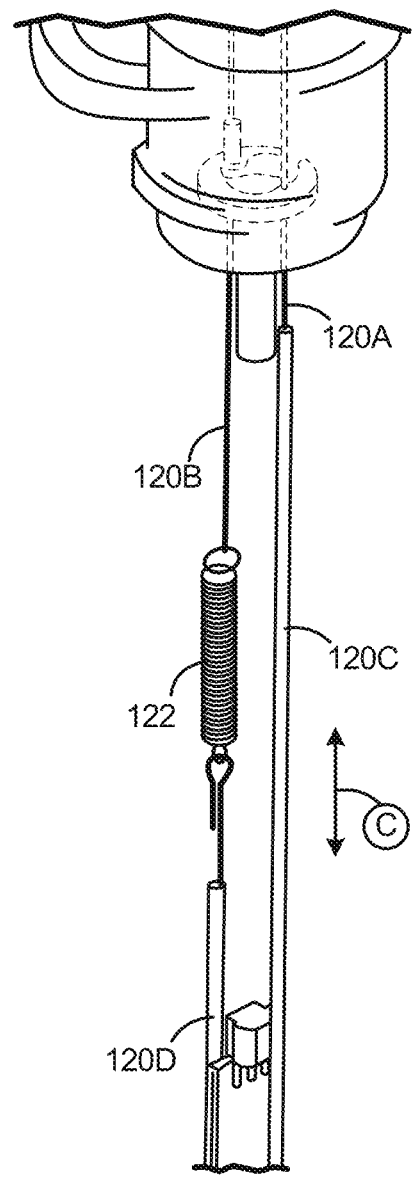
FIG. 5G is a further perspective internal view of the embodiment of FIG. 5F.

As best shown in the implementation of FIG. 5E-G, camera tilt is driven by a tilt actuator 100 disposed within the handle 40. The tilt actuator 100 in these implementations can be a 6 mm Maxon BLDC motor, or other such actuator. In these implementations, the tilt actuator 100 is capable of causing translational movement in the lead screw nut 90. In these implementations, the tilt actuator 100 drives a planetary gearhead and spur gear 102, which is coupled to a drive gear 104. In these implementations, the drive gear 104 is in rotational communication with the lead screw 106. In these implementations, rotation of the lead screw 106 within the lead screw nut 90 causes translational motion of the lead screw nut 90 and optionally a cable coupler assembly 108 fixedly attached to the lead screw nut 90 exterior. It is understood that in these implementations the lead screw nut 90 is rotationally coupled, but linearly decoupled, from the pan shaft 112, such that rotation of lead screw 106 causes linear translation of lead screw nut 90. In various implementations, an actuation cable (best shown at 120A, 120B in FIGS. 5F-G) is fixedly coupled to coupler assembly 108 such that translation of the lead screw nut 90 and cable coupler assembly 108 causes tilt actuation to occur.

As shown in FIGS. 5F-G, In various implementations, tilt functionality can be accomplished via the following configuration. In this embodiment, the flexible section 42B includes an elbow joint 124 and a pair of tilt cables 120A, 120B, wherein each of the tilt cables 120A, 120B is operably coupled at its distal end to the optical section 42C. In various implementations, and as shown, the cables 120A, 120B comprise a teflon sheathing 120C, 120D. In these implementations, the sheathings can remain static, while the cables 120A, 120B disposed within are able to slide relative to the sheathing as described generally herein.

The first tilt cable 120A is depicted in FIG. 5F-G is an active tilt cable 120A that is coupled on one side of the optical section 42C in relation to the joint 124 as shown such that urging the cable 120A proximally causes the optical section 42C to tilt upward on that side, as is designated by reference arrow C. The second tilt cable 120B is a passive tilt cable 120B that is coupled on the other side of the optical section 42C in relation to the joint 124 and the first title cable 120A. The second tilt cable 120B is not actuated by a user. Instead, the second tilt cable 120B is maintained at a predetermined level of tension by a passive spring 122 such that the cable 120B is continuously urged in the proximal direction, thereby urging the optical section 42C into a straight configuration such as that shown in FIG. 4B.

As such, in this implementation of FIGS. 5F-G, the default position of the optical section 42C will be the straight configuration. That is, the tensioned passive tilt cable 120B causes the optical section 42C to be in the straight configuration when no forces are being applied to the active tilt cable 120A by the cable coupler assembly 108. A user can cause proximal movement of the cable coupler assembly 108 through the lead screw nut, as described above, causing the active title cable 120A to be urged proximally to tilt the optical section 42C. In response to other activities, such as depressing the button 70, the cable 120A can be caused to allow the section 42C to return to the straight configuration by way of the spring 122 and return cable 120B. The straight configuration of FIG. 4B makes it easy to position the camera component 18 into the lumen 62 and further to remove the camera component 18 from the lumen 62 as well. In use, a user can urge the active cable 120A proximally to tilt the optical section 42C as desired/needed. In alternative embodiments, the system can have an actuation button (or other type of user interface) (not shown) that can be configured to actuate the system to move to the straight configuration, thereby facilitating easy insertion and/or removal.

Figure 6A:
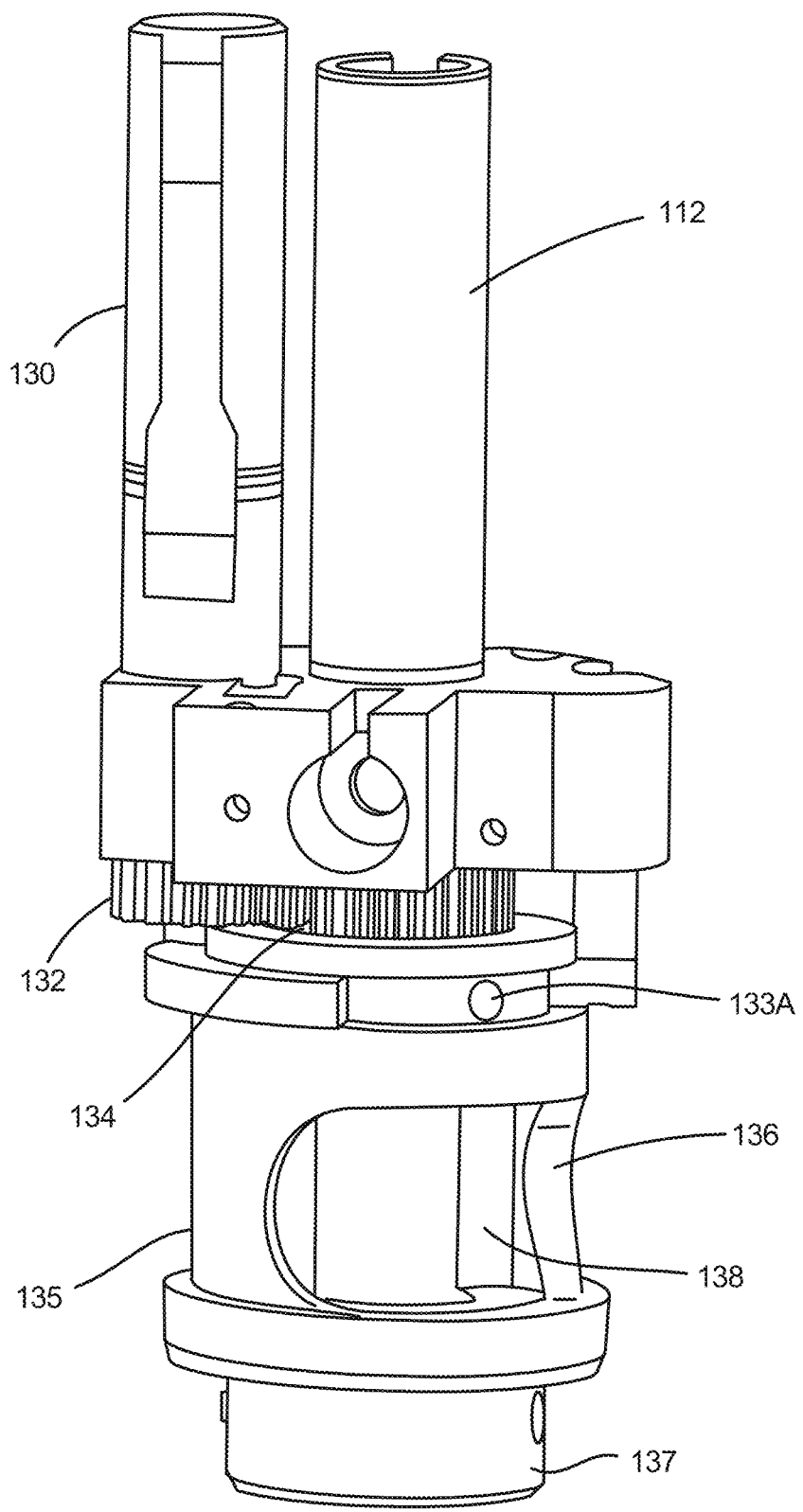
FIG. 6A is a side view of the internal components of a camera component according to one embodiment.
Figure 6D:
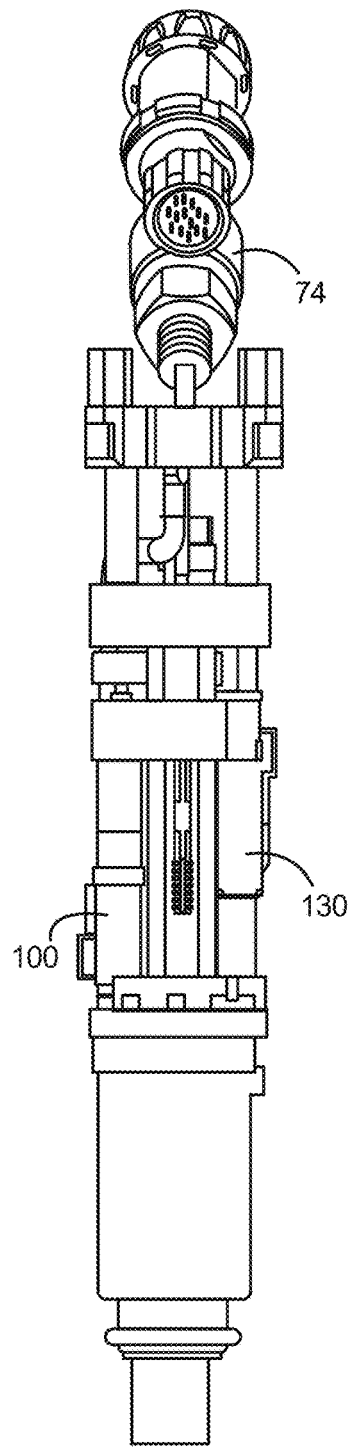
FIG. 6D is a internal front view of the internal components of a camera component according to the embodiment of FIG. 6B.

The pan functionality is accomplished via rotation of the tube 42 around the longitudinal axis of the tube 42 as shown by arrow D in FIG. 5G-F. The rigid section 42A, the flexible section 42B, and the optical section 42C of the tube (not shown) are coupled together such that the sections 42A, 42B, 42C cannot rotate in relation to each other. In other words, the sections 42A, 42B, 42C rotate together as a single unit. The tube 42, however, is rotatably coupled to the handle 40 such that the tube 42 can rotate as shown by arrow D in relation to the handle 40. As a result, the panning functionality is provided by positioning the optical section 42C in a tilted configuration (such as the configuration of FIG. 5F) and rotating the tube 42 in relation to the handle 40. This results in the optical component in the optical section 42C being rotated around the tube 42 axis such that it can potentially capture images up to and including 360° around the camera component 18. In certain implementations, pan is limited to smaller ranges, such as 100°, such as by way of a hard stop 133, as shown in FIGS. 6A-B. In these implementations, the hard stop 33 rotates with the tube 42 and tube head 137 (or lead screw 106), while the tube housing 135 (or lead screw nut 90) maintains a fixed position, thereby limiting the range of tube 42 motion, as the hard stop 133 is unable to rotate through the tube housing 135. A hard stop opening 133A can also be provided in the tube head 137, as is shown in FIG. 6A. It is understood that in certain implementations, the limiting of pan range is done because of wire service loops.

As such, in the implementation of FIGS. 5F-6E, pan functionality is performed by way of a pan actuator 130 disposed within the handle 40, which is best shown in FIG. 6A. The pan actuator 130 in these implementations can be a 6 mm Maxon BLDC motor, or other such actuator. In these implementations, the pan actuator 130 is capable of causing rotational movement in the tube 42. In these implementations, the pan actuator 130 drives a planetary gearhead and spur gear 132, which is coupled to a drive gear 134. In these implementations, the drive gear 134 is in rotational communication with the pan shaft 112, which in turn is in rotational communication with the tube 42. It is understood that in these implementations the pan shaft 112 is rotationally coupled to the tube 42, such that rotation of the pan shaft 112 causes rotation of the entire tube 42, including the optical portion 42C, thus resulting in pan functionality. FIGS. 6B-D depict further implementations of the internal components of the camera handle 40, showing the pan actuator 130 and tilt actuator 100 disposed within the handle housing (not shown).

In these implementations, the pan assembly (generally at 128) has a ground slot 136 (which does not rotate) and a pan shaft slot 138 (which rotates), both being configured such that wires (not shown) may pass through the slots 136, 138 safely and not be damaged during pan actuation.

Figure 6E:
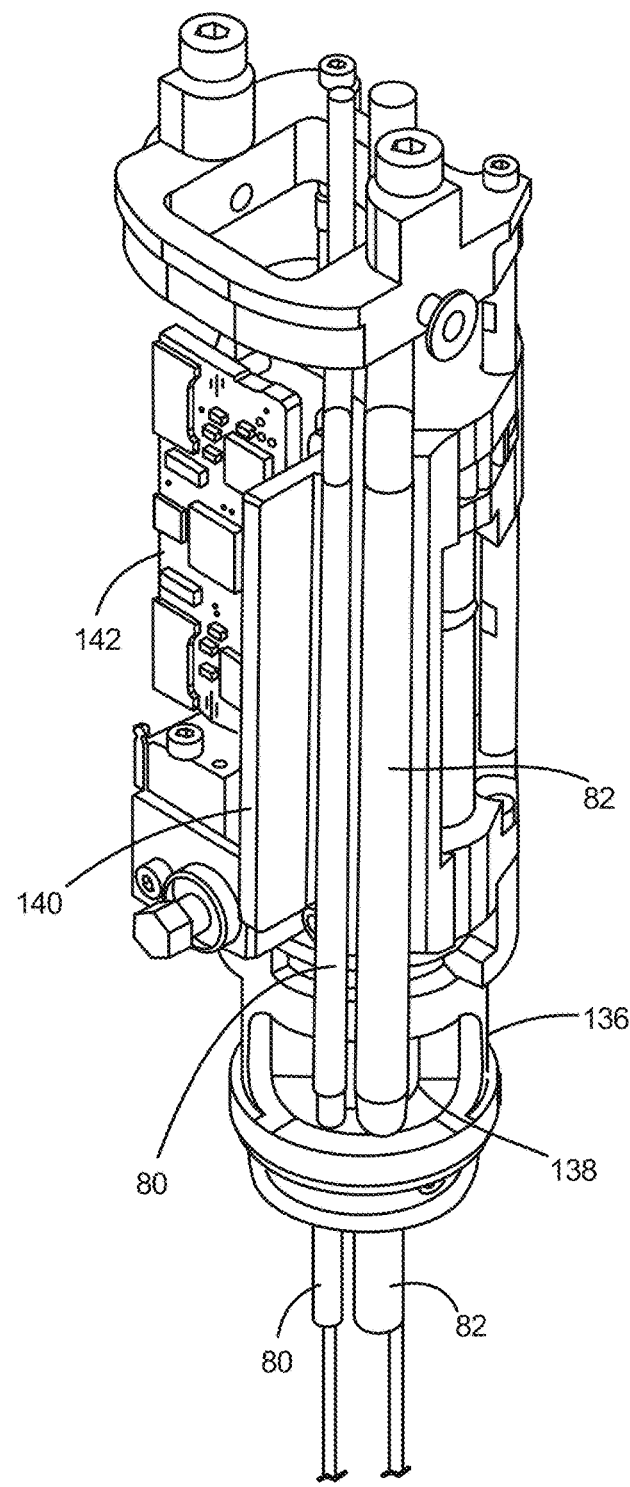
FIG. 6E is a perspective internal view of a camera component inserted into a robotic surgical device according to one embodiment.

For example, as is shown in FIG. 6E, the image sensor power/communication lines 82 and the fiber optic illumination cable 80 are routed over a support 140 and pass through the slots 136, 138 in the to enter the camera tube 42 and extend to the lens 48. At least one handle rigid-flex PCB component, or "PCB" 142 is also provided to control various the camera handle functions, such as tilt and pan. It is understood that in certain implementations, a third degree of freedom is attainable with digital (software) based zoom.

Figure 7A:
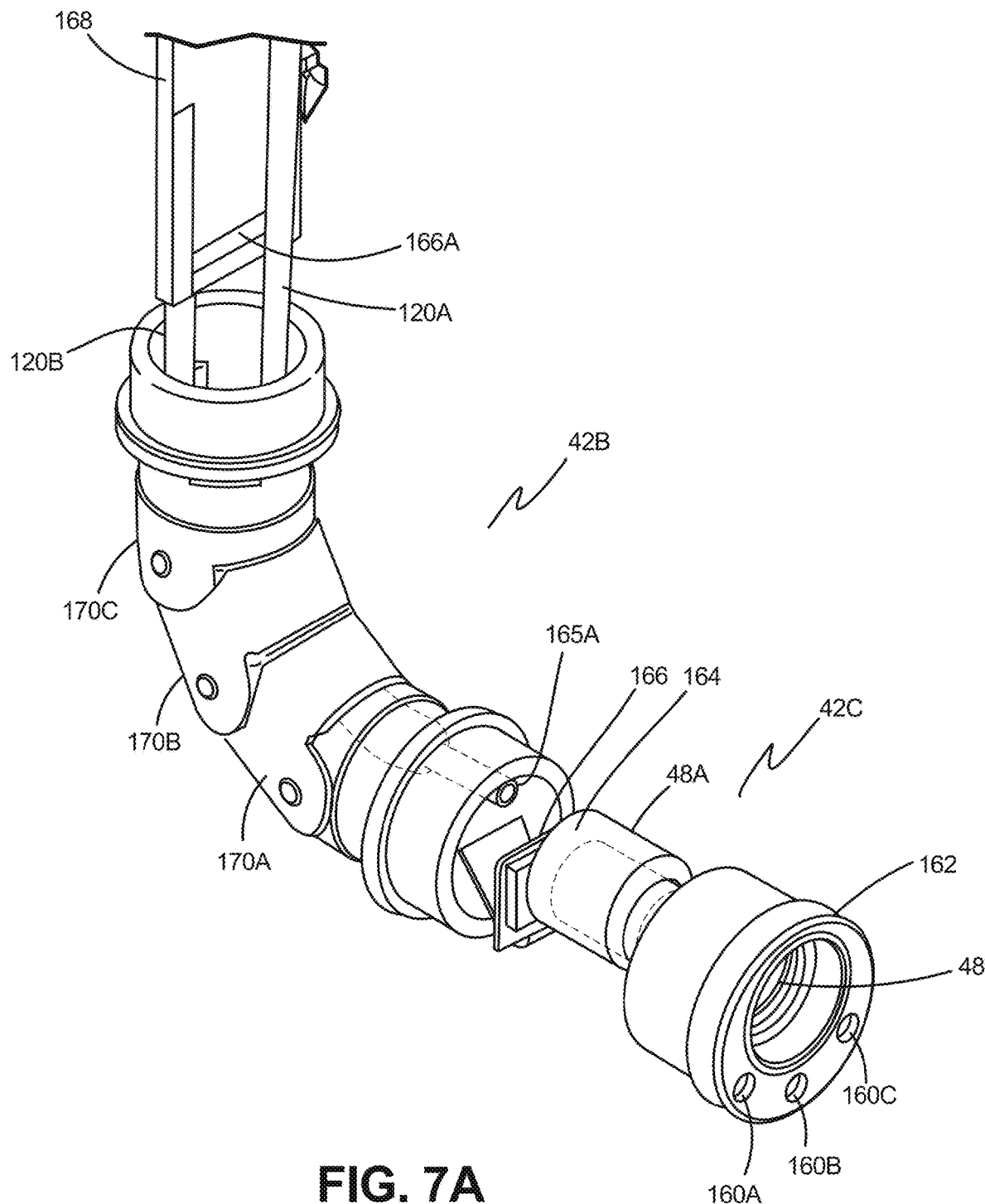
FIG. 7A is a perspective internal view of the distal end of the camera component according to one embodiment.
Figure 7B:
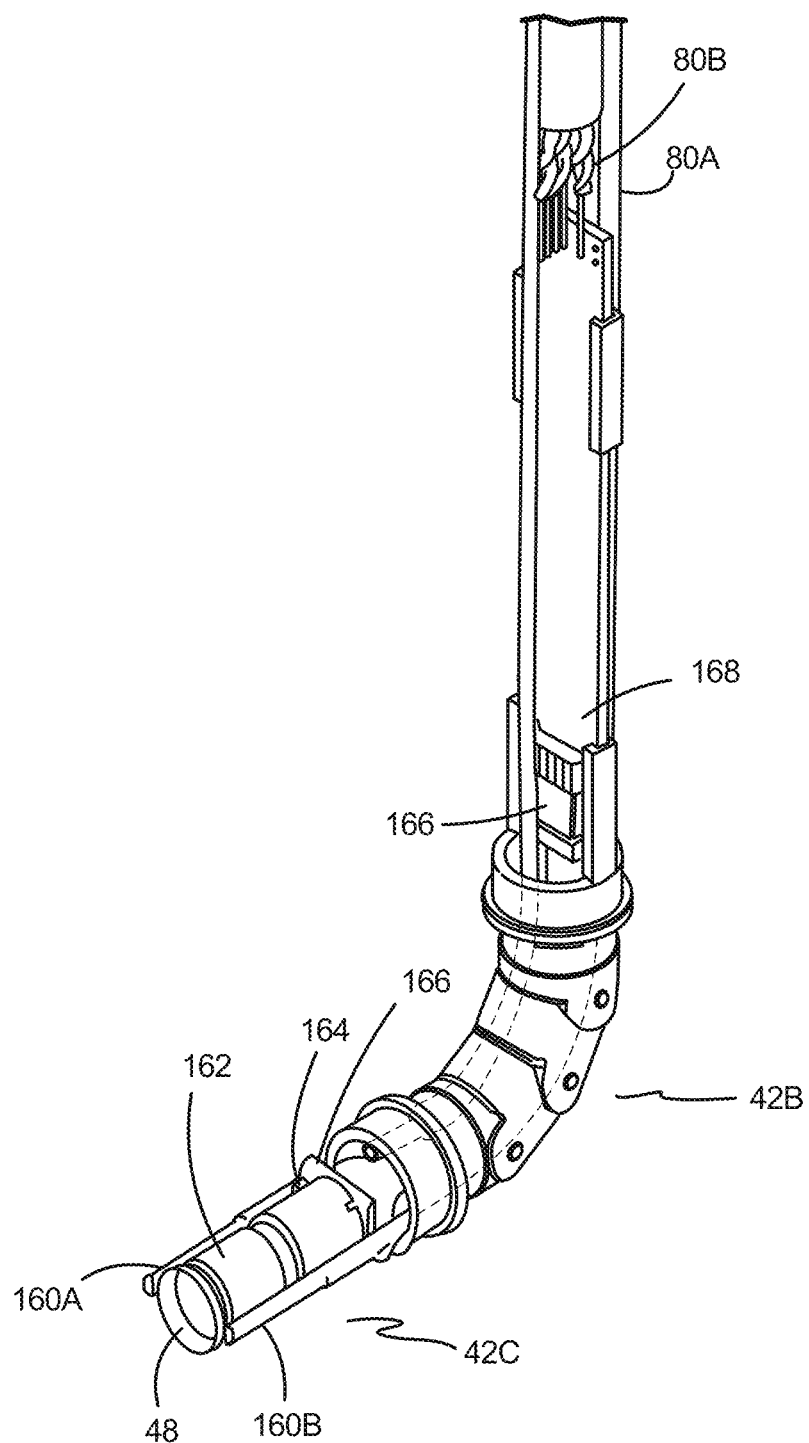
FIG. 7B is a perspective internal view of the distal end of the camera component according to another embodiment.

FIGS. 7A and 7B depict various internal views of the flexible section 42B and distal camera components.

The implementation of FIG. 7A has a camera lens 48 which contains a stack 48A of lenses configured to optimize, among other parameters, field of view (such as approximately 90 degrees) and depth of field (approximately 1" to 6" focal range). A plurality of fiber optic lights 160 are also disposed in a lens housing 162. As is shown in FIGS. 7A-B, in various implementations, these fiber optics 160A, 160B, 160C can be disposed on opposite sides of the lens 48 (FIG. 7B) or radially around and/or "under" the lens 48 (FIG. 7A). These fiber optics 160A, 160B, 160C are in luminary communication with the fiber optic cable or cables 80A, 80B extending down from the handle, as discussed above, for example in relation to FIG. 6F.

In the implementation of FIGS. 7A-B, an image sensor 164 (such as an OmniVision 22720 IC, capable of 1080p @30 fps) is disposed behind the lens stack 48A on flex tape 166. In these implementations, the image sensor 164 or sensors outputs data in a MIPI format through the flex tape 166, which is in turn threaded through the flexible portion 42B. The flex tape 166 terminates at a termination point 166A into a rigid PCB 168 at the distal end of the camera tube (not shown). It is understood that the flexible tube portion 42B in the implementation of FIG. 7A comprises a plurality of articulating members 170A, 170B, 170C, as has been previously described, though other implementations are possible.

Figure 7C:
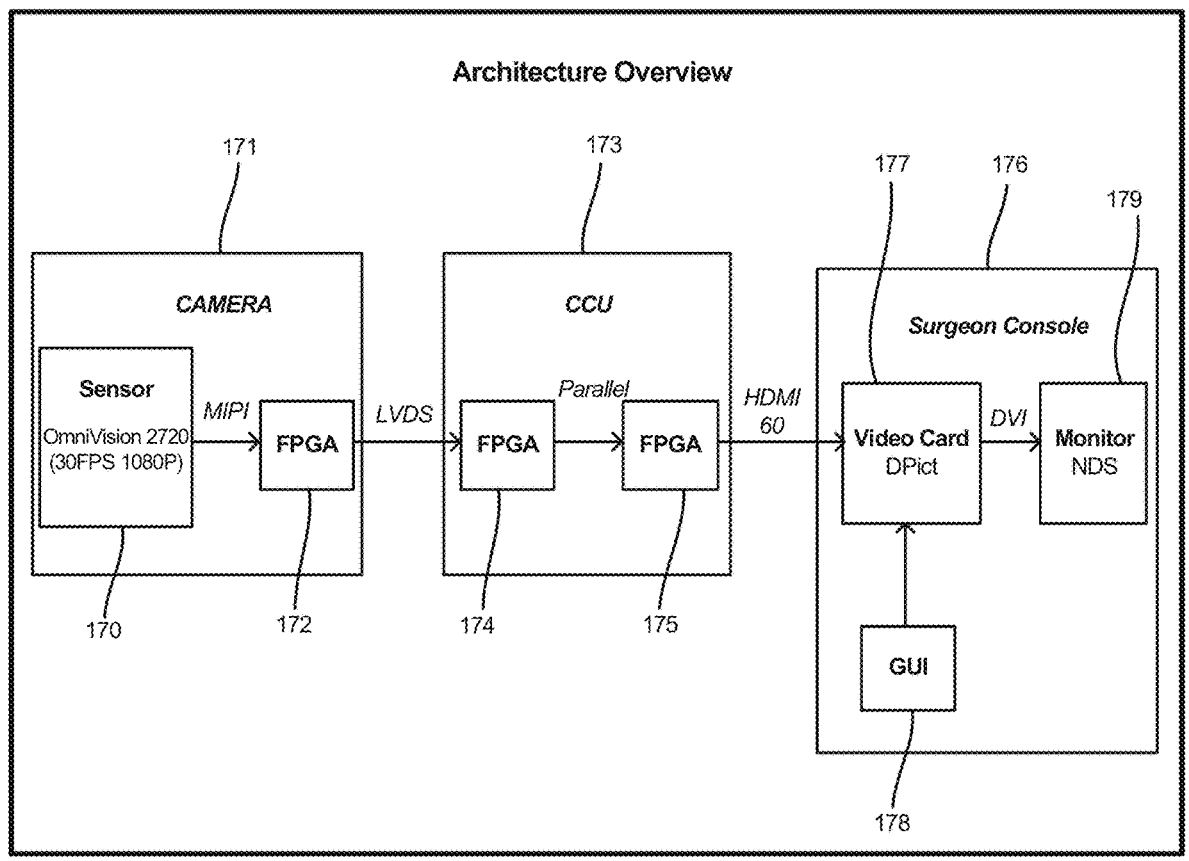
FIG. 7C is a schematic flow of camera information from a lens to a surgical console, according to one embodiment.

In various embodiments, and as shown generally in FIG. 7C, the sensor image signal (box 170) from the flex tape 166 is converted in the camera (box 171) from MIPI to LVDS by an FPGA (box 172) on the PCB 168. In an exemplary implementation, this LVDS signal is then transmitted through the internal camera harness, through the connector on the camera handle, through the 5' camera pigtail, through a connector pair, through a 20' harness, through a panel mount connector on the surgeon console, through the surgeon console internal harness to a panel mount connector on the CCU (camera control unit—box 173), through the internal CCU harness, into the daughter card.

In the implementation of FIG. 7C, the CCU (box 173) translates the LVDS signal to parallel data (boxes 174 and 175), then to an HDMI output. The HDMI output is routed to the surgeon console computer (box 176) to an onboard video processing card (box 177). In various implementations, the video processing card (box 177) mixes the camera feed with GUI overlays (box 178), such that the mixed signal can be passed to the main monitor (box 179) on the surgeon console (box 176) where it is viewed. This signal is also mirrored on an HDMI output on the surgeon console connector panel, where it may be routed to an auxiliary monitor. It is understood that there are many different signaling protocols that may be used. In one example, the rigid PCB 168 at the distal end of the rigid tube 42 may convert the MIPI data to serial data instead and transmit the serialized signal along a coaxial cable back to the CCU. In another example, the video processing card (box 177) and GUI overlays (box 178) may be omitted, and the video signal may be routed directly from the CCU to the main display. In a further example, the video signal may be mirrored from the main display (box 179) instead of (or in addition to) the surgeon console connector panel.

Figure 8E:
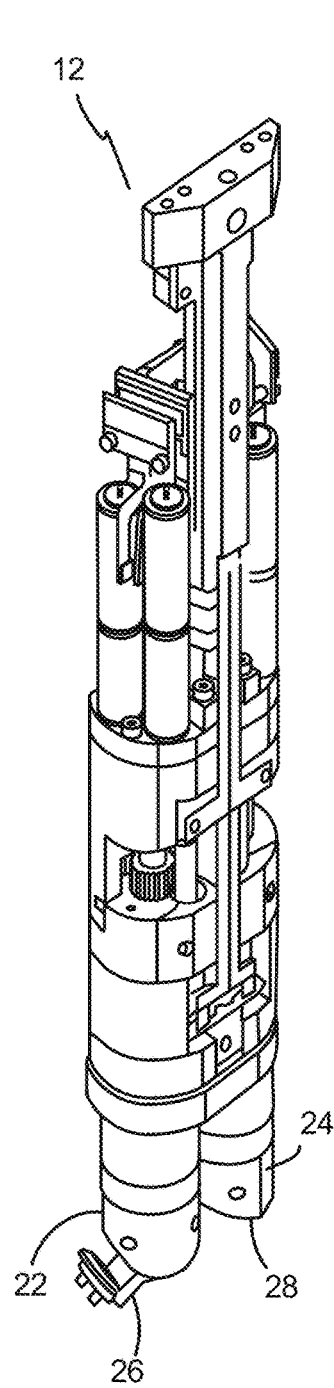
FIG. 8E is a rear three-quarters perspective view of the device body without a housing, according to one embodiment.
Figure 8F:
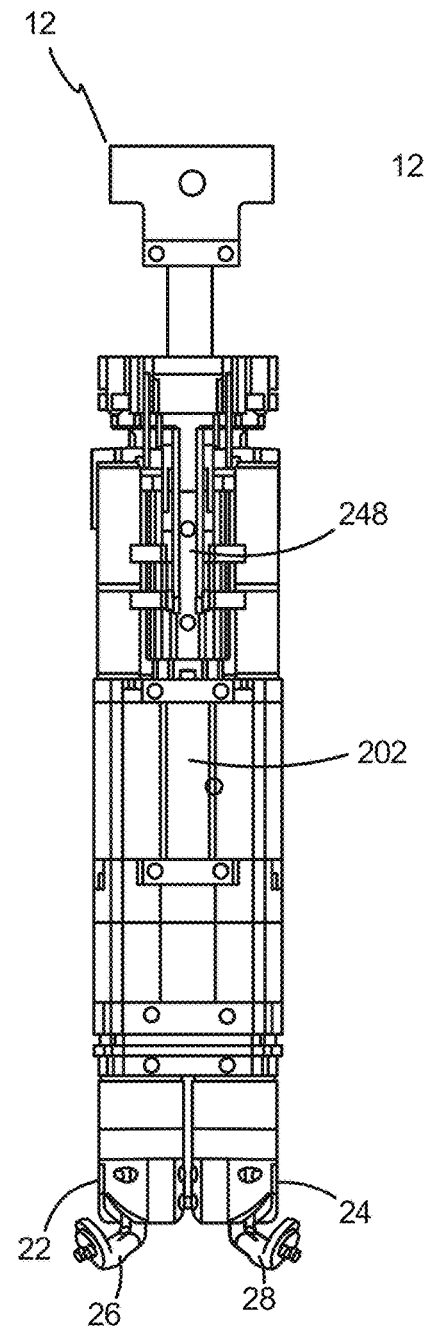
FIG. 8F is a side view of the embodiment of FIG. 8E.
Figure 8G:
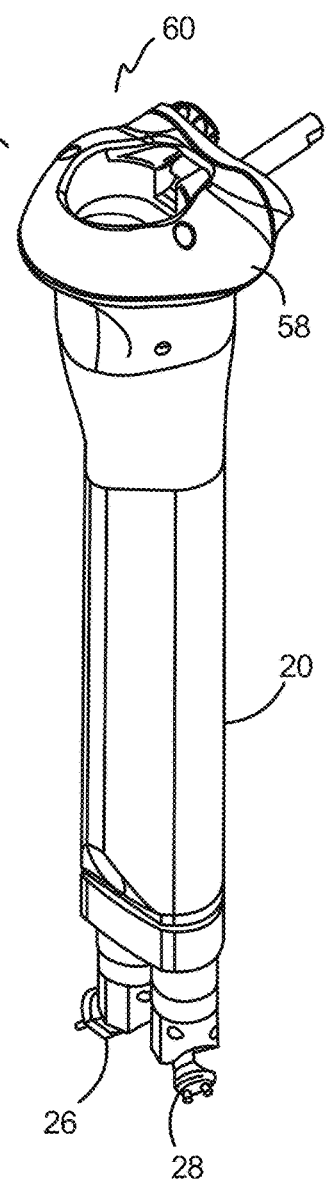
FIG. 8G is a front three-quarters perspective view of the embodiment of FIG. 8E with the housing.
Figure 9A:
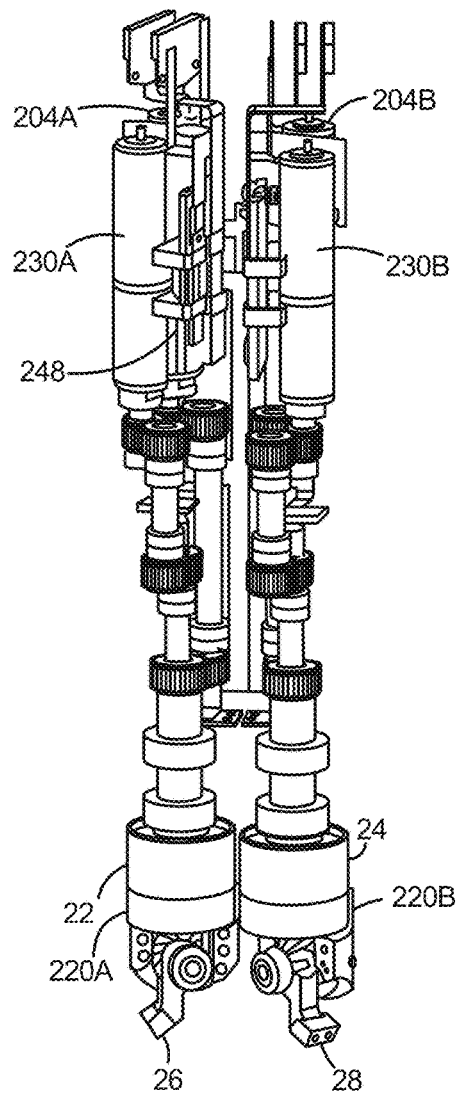
FIG. 9A is an internal front view of the device body showing the internal components without a housing or support structures, according to one embodiment.
Figure 9B:
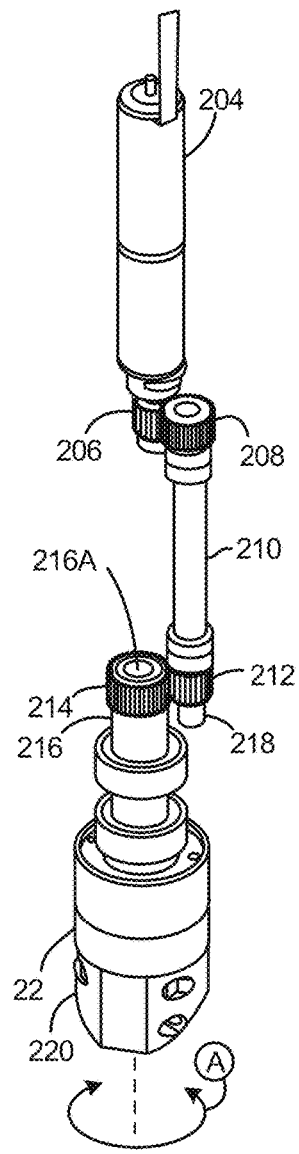
FIG. 9B is a perspective view of certain yaw components of the embodiment of FIG. 9A.
Figure 9C:
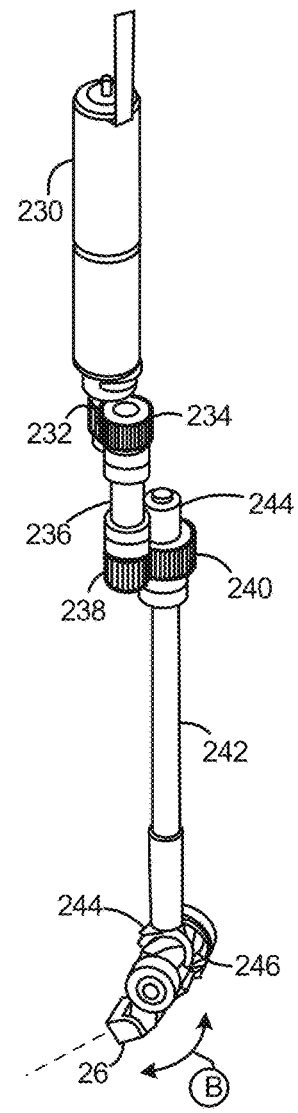
FIG. 9C is a perspective view of certain pitch components of the embodiment of FIG. 9A.
Figure 11E:
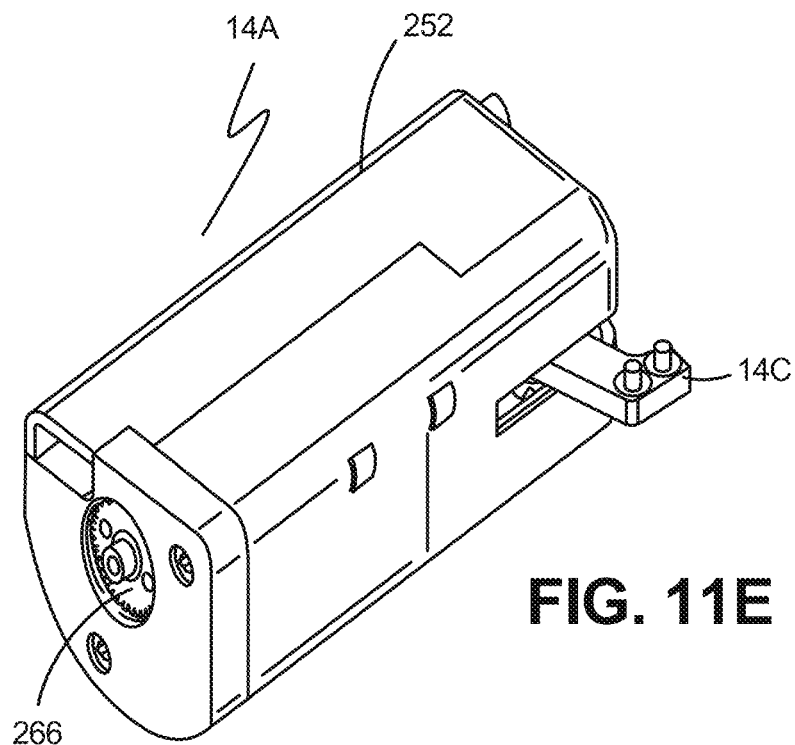
FIG. 11E is a perspective view of an upper robotic arm according to one embodiment.
Figure 11F:
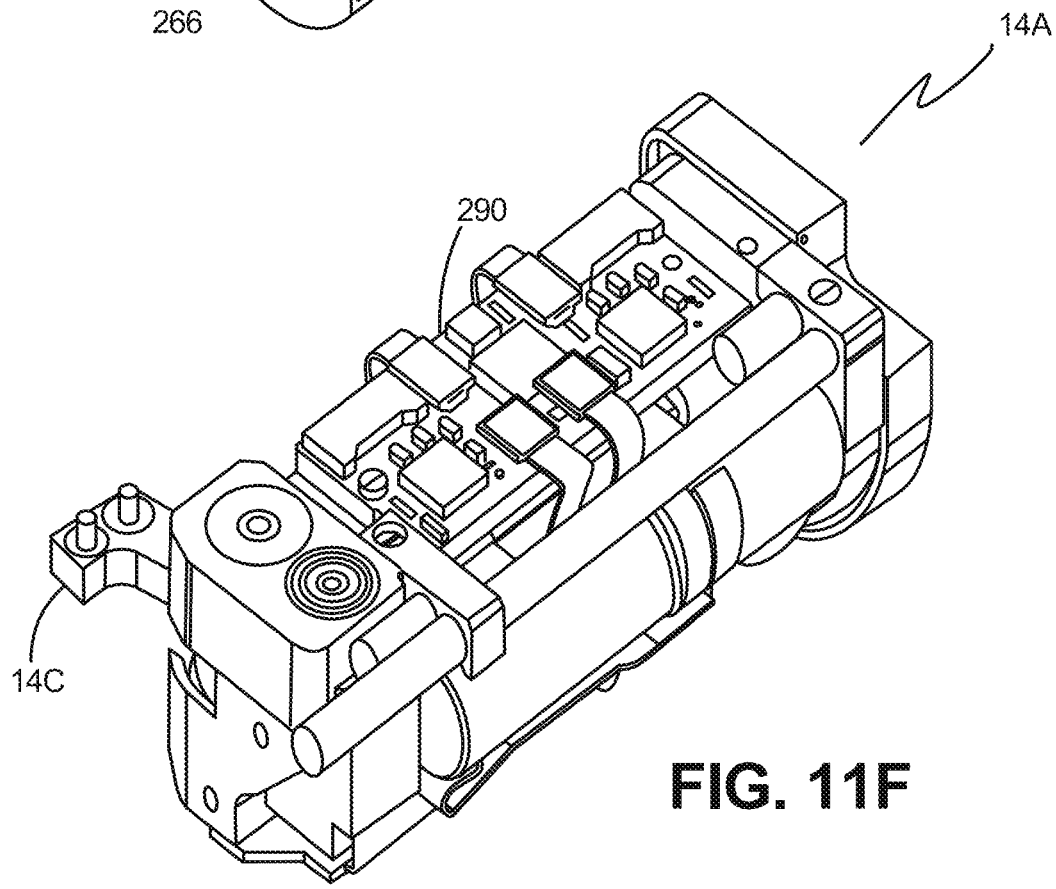
FIG. 11F is a rotated perspective view of the embodiment of FIG. 11E, without the housing.

FIGS. 8A-G and 9A-D according to one embodiment, depict the internal components of the body 12, which is shown in these figures without its casing 20. FIGS. 9B-C depict the right half of the body 12 and the internal components that control/actuate the right arm 14A. It is understood that the internal components in the left half (not shown) that operate/control/actuate the left arm 14B are substantially the same as those depicted and described herein and that the descriptions provided below apply equally to those components as well.

FIGS. 8A-G include the internal structural or support components of the body 12. In one implementation, the body 12 has an internal top cap 200 and an internal support shell 202 as shown. These components maintain the structure of the body 12 and provide structural support for the components disposed therein. FIG. 8D is an enlarged view of the distal end of the body 12.

In contrast to FIGS. 8A-D, FIGS. 9B-C depict the internal actuation and control components of the body 12 with the internal structural or support components hidden in order to better display the internal actuation and control components. These internal actuation and control components are configured to provide two degrees of freedom at the shoulder joint 26, 28.

In one embodiment, certain of the internal components depicted in FIGS. 9A-C are configured to actuate rotation at the shoulder joint 26, 28 around axis A (as best shown in FIG. 9A), which is parallel to the longitudinal axis of the body 12. This rotation around axis A is also referred to as "yaw" or "shoulder yaw." The rotation, in one aspect, is created as follows. A yaw actuator 204 is provided that is, in this implementation, a yaw motor assembly. The yaw motor assembly 204 is operably coupled to the yaw motor gear 206, which is coupled to the driven gear 208 such that rotation of the yaw motor gear 206 causes rotation of the driven gear 208. The driven gear 208 is fixedly coupled to a transmission shaft 210, which has a transmission gear 212 at the opposite end of the shaft 210.

The transmission gear 212 is coupled to a driven gear 214, which is fixedly coupled to the shaft 216. A magnet holder 218 containing a magnet is also operably coupled to the transmission gear 212. The holder 218 and magnet are operably coupled to a magnetic encoder (not shown). It is understood that the magnet holder 218, magnet, and magnetic encoder (and those similar components as discussed elsewhere herein in relation to other joints) are components of an absolute position sensor that is the same as or substantially similar to one or more of the absolute position sensors disclosed in U.S. Provisional Application 61,680, 809, filed on Aug. 8, 2012, which is hereby incorporated herein by reference in its entirety. The shaft 216 is fixedly coupled at its distal end to a rotatable pitch housing 220 (as best shown in FIGS. 9A-B) such that rotation of the driven gear 214 causes rotation of the shaft 216 and thus rotation of the housing 220 around axis A as shown in FIG. 8B and FIG. 9B (this is also shown in FIG. 10 at axis $Z_1$).

According to one implementation, certain other internal components depicted in FIG. 9C are configured to actuate rotation of the shoulder joint 26, 28 around axis B (as best shown in FIGS. 8C and 9C), which is perpendicular to the longitudinal axis of the body 12. This rotation around axis B is also referred to as "pitch" or "shoulder pitch." The rotation, in one embodiment, is created as follows. A pitch actuator 230 is provided that is, in this implementation, a pitch motor assembly 230. The pitch motor assembly 230 is operably coupled to a motor gear 232, which is coupled to the driven gear 234 such that rotation of the motor gear 232 causes rotation of the driven gear 234. The driven gear 234 is fixedly coupled to a transmission shaft 236, which has a transmission gear 238 at the opposite end of the shaft 236. The transmission gear 238 is coupled to a driven gear 240, which is fixedly coupled to the shaft 242. A magnet holder 244 containing a magnet is also operably coupled to the driven gear 240. The holder 244 and magnet are operably coupled to a magnetic encoder (not shown). As best shown in FIG. 9B-C, a portion of the shaft 242 is disposed within the lumen 216A of the shaft 216 described above and extends out of the distal end of the shaft 216 into the housing 220. As best shown in FIG. 9C, the distal end of the shaft 242 is coupled to a rotation gear 244 that is a bevel gear 244. The rotation gear 244 is operably coupled to link gear 246, which is also a bevel gear 246 according to one implementation. The link gear 246 is operably coupled to the shoulder link 16A (discussed above) such that rotation of the shaft 242 causes rotation of the rotation gear 244 and thereby the rotation of the link gear 246 and thus rotation of the link 16A around axis B as best shown in FIG. 9D, also shown in FIG. 10 at axis $Z_2$.

In this embodiment, these two axes of rotation are coupled. That is, if solely rotation around axis A (pure yaw) is desired, then the "pitch drive train" (the pitch motor 230 and all coupled gears and components required to achieve rotation around axis B) must match the speed of the "yaw drive train" (the yaw motor 204 and all coupled gears and components required to achieve rotation around axis A) such that there is no relative angular displacement between the pitch housing 220 and the rotation gear 244. In contrast, if solely rotation around axis B (pure pitch) is desired, then the yaw drive train must hold position while the pitch drive train is actuated.

In one implementation as shown in FIG. 9A, the body 12 has a rigid-flex PCB 250 positioned in the body. The PCB 250 is operably coupled to and controls the motors 204, 230 and magnetic encoders (not shown). In one implementation, and as shown in FIGS. 8F, 9A and elsewhere the various actuators or motors described herein have at least one temperature sensor 248 disposed on the surface of the motor, for example by temperature-sensitive epoxy, such that the temperature sensors 248 can collect temperature information from each actuator for transmission to the control unit, as discussed below. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass. There are many ways to actuate these motions, such as with DC motors, AC motors, permanent magnet DC motors, brushless motors, pneumatics, cables to remote motors, hydraulics, and the like.

As also described herein, each link (body, upper arm, and forearm) can also contain Printed Circuit Boards (PCBs) that have embedded sensor, amplification, and control electronics. For example, in certain implementations, identical PCBs 168, 250, 290, 320, 328 are used throughout where each one controls two motors. One PCB is in each forearm and upper arm and two PCBs are in the body. Each PCB also has a full 6 axis accelerometer-based Inertial Measurement Unit and temperature sensors that can be used to monitor the temperature of the motors. Each joint can also have either an absolute position sensor or an incremental position sensor or both. In certain implementations, the some joints contain both absolute position sensors (magnetic encoders) and incremental sensors (hall effect). Joints 5 & 6 only have incremental sensors. These sensors are used for motor control. The joints could also contain many other types of sensors. A more detailed description of one possible method is included here.

FIG. 10 shows the robot motions. As shown in relation to FIG. 10, the shoulder joint 26 connects the upper arm 14A to the body 12. Shoulder yaw ($\theta_1$ about $Z_1$), shoulder pitch ($\theta_2$ about $Z_2$) and shoulder roll ($\theta_3$ about $Z_3$) may or may not have the three axes largely intersect so as to form a spherical-like joint. The elbow joint 14C ($\theta_4$ about $Z_4$) connects the upper arm 14A to the forearm 14B. Then the tool can roll ($\theta_5$ about $Z_5$). Finally, the tool itself (or end effector) has a motion that can be used to open and close the tool. The right arm 14 of this design is a mirror image of the left 16. FIGS. 11A-14C, according to one embodiment, depict the internal components of the right arm 14. It is understood that the internal components in the left arm 16 are substantially the same as those depicted and described herein and that the descriptions provided below apply equally to those components as well.

FIGS. 11A-F and 12A-D, according to one embodiment, depict the internal components of the right upper arm 14A, which is shown in FIGS. 11A-E and 12A-D without its housing 252. More specifically, these figures depict the right arm 14A and the internal components therein. FIGS. 12A-D depict the internal components of the right upper arm 14A, including actuators, drive components, and electronics, with the internal structural or support components hidden in order to better display the internal components. In contrast to FIGS. 12A-D, FIGS. 11A-F include both the internal actuator, drive, and electronics components, but also the internal structural or support components of the right upper arm 14A.

In one embodiment, certain of the internal components depicted in FIGS. 11A-F and 12A-D are configured to actuate rotation at the shoulder link 26 around $Z_3$ as $\theta_3$ (as best shown in FIG. 10), which is parallel to the longitudinal axis of the right upper arm 14A. This rotation $\theta_3$ is also referred to as "shoulder roll." The rotation, in one aspect, is created as follows. An actuator 260 is provided that is, in this implementation, a motor assembly 260. The motor assembly 260 is operably coupled to the motor gear 262. The motor gear 262 is supported by a bearing pair 264. The motor gear 262 is coupled to the driven gear 266 such that rotation of the motor gear 262 causes rotation of the driven gear 266. The driven gear 266 is fixedly coupled to the shoulder link (not shown) such that rotation of the driven gear 266 causes rotation of the upper arm 14A around axis $Z_3$ as shown in FIG. 10. The driven gear 266 is supported by a bearing pair 268. A magnet holder 270 containing a magnet is also operably coupled to the driven gear 266. The holder 270 and magnet are operably coupled to a magnetic encoder, as has been previously described.

The rotation of the shoulder link 26 around axis $Z_3$ causes the right upper arm 14A (and thus the forearm 14B) to rotate in relation to the body 12. According to one embodiment, this rotation adds an additional degree of freedom not provided in prior two-armed surgical devices.

According to one implementation, certain of the internal components depicted in FIGS. 11A-12D are configured to actuate rotation at the elbow link 14C around axis $Z_4$ (as best shown in FIG. 3C), which is perpendicular to the longitudinal axis of the right upper arm 14A. This rotation around axis $Z_4$ is also referred to as "elbow yaw." The rotation, in one aspect, is created as follows. An actuator 272 is provided that is, in this implementation, a motor assembly 272. The motor assembly 272 is operably coupled to the motor gear 274, which is a beveled gear in this embodiment. The motor gear 274 is supported by a bearing 276. The motor gear 274 is coupled to the driven gear 278 such that rotation of the motor gear 274 causes rotation of the driven gear 278. The driven gear 278 is fixedly coupled to the elbow link 14C such that rotation of the driven gear 278 causes rotation of the elbow link 14C around axis $Z_4$ as shown in FIG. 10. The driven gear 278 is supported by a bearing pair 280. A magnet holder containing a magnet is also operably coupled to the elbow link 14C. The holder and magnet are operably coupled to a magnetic encoder 282. According to one embodiment, the additional coupling of a link gear 284 and the elbow link 14C can provide certain advantages, including an additional external reduction (because the gear 284 has fewer gear teeth than the elbow link 14C) and shortening of the upper arm 14A (thereby improving the joint range of motion). The gear 284 is coupled to another gear which has the magnetic holder 282 on it. Additionally, this other gear (not shown) has a torsion spring attached to it, which functions as an anti-backlash device.

Figure 12A:
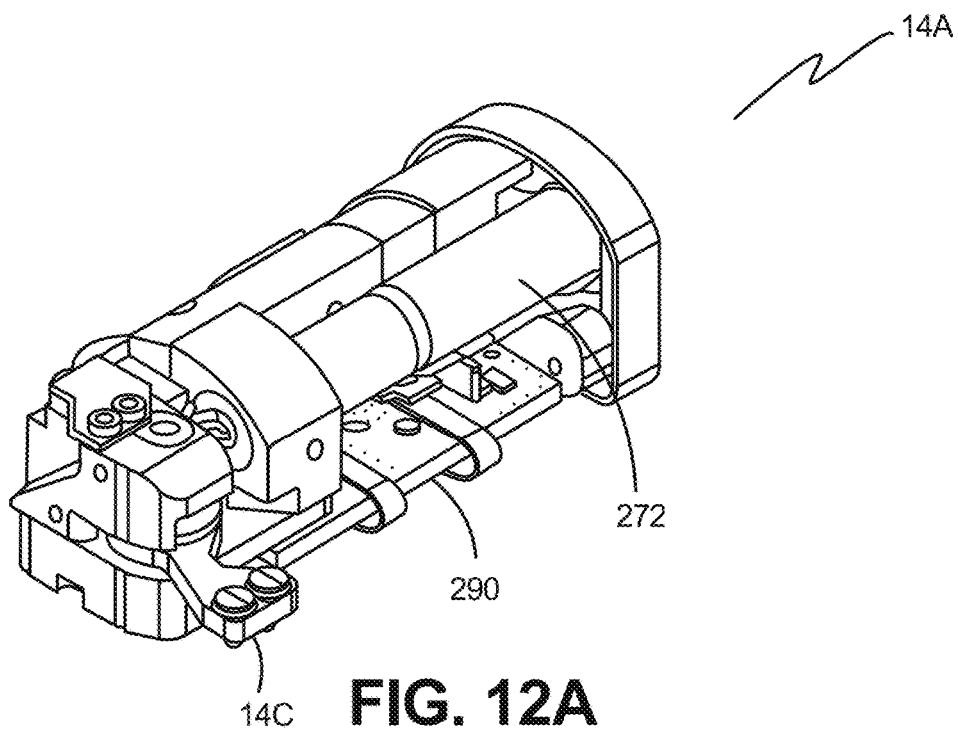
FIG. 12A is a further rotated view of the embodiment of FIG. 11E.
Figure 12B:
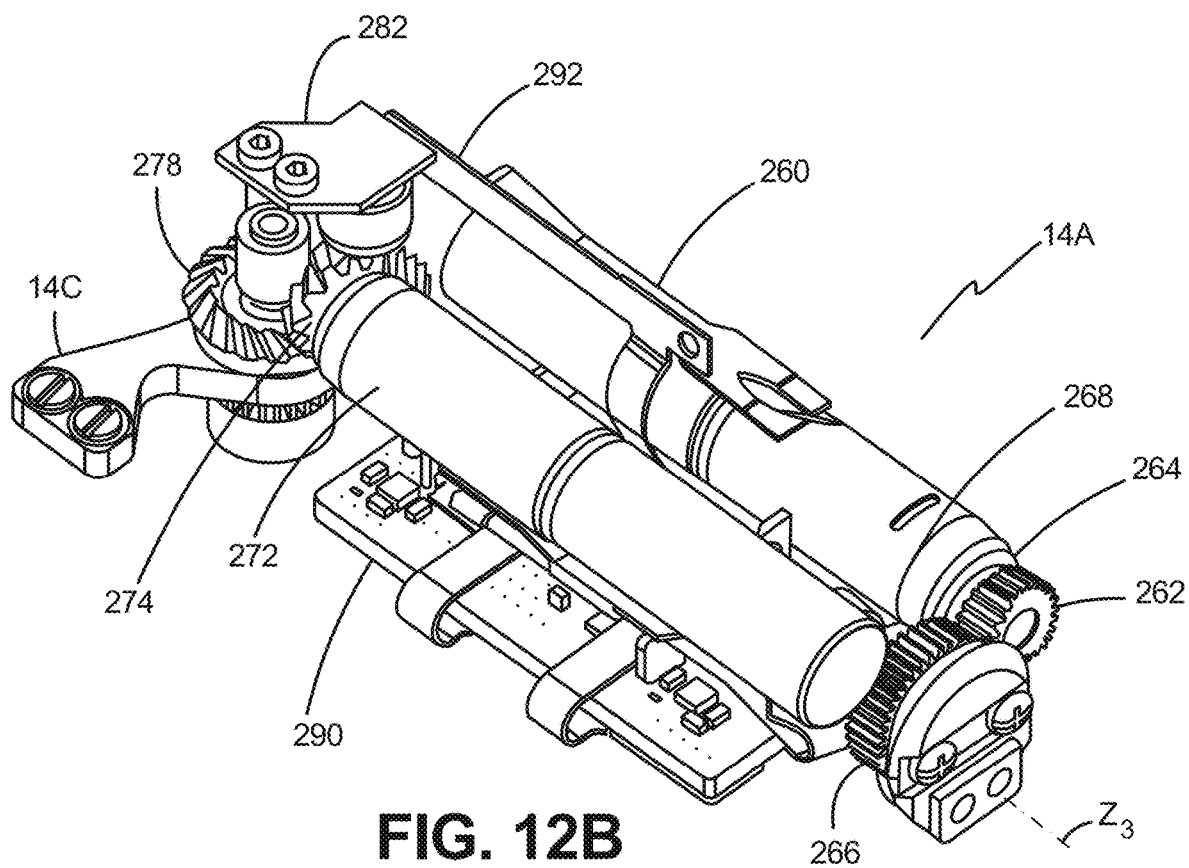
FIG. 12B is another internal view of the components of an upper robotic arm according to one embodiment.
Figure 12C:
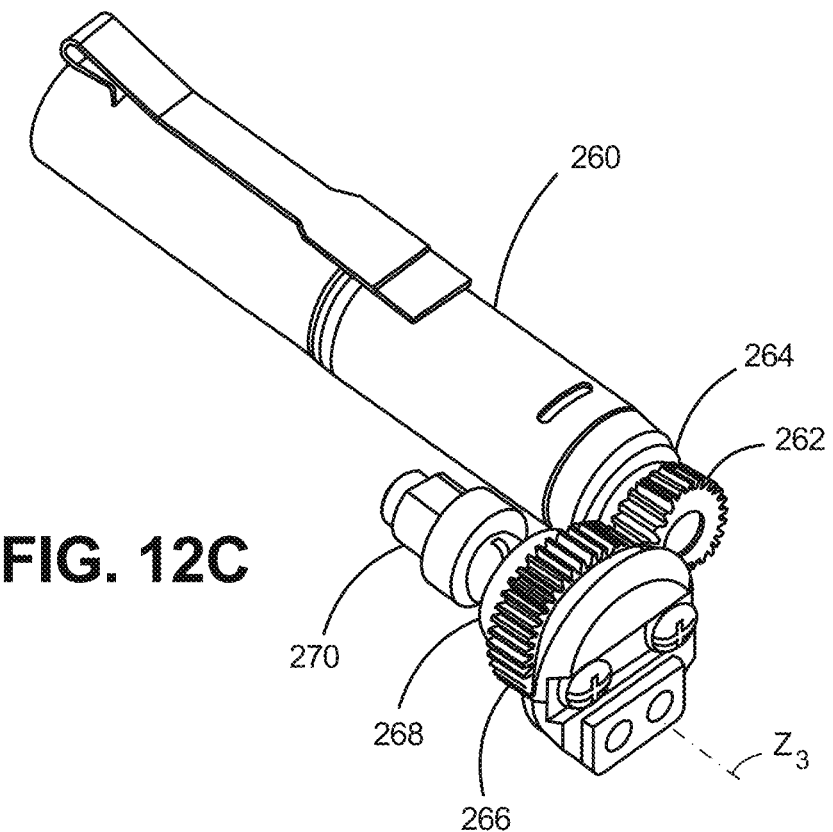
FIG. 12C is a perspective view of certain yaw components of the embodiment of FIG. 12B.
Figure 12D:
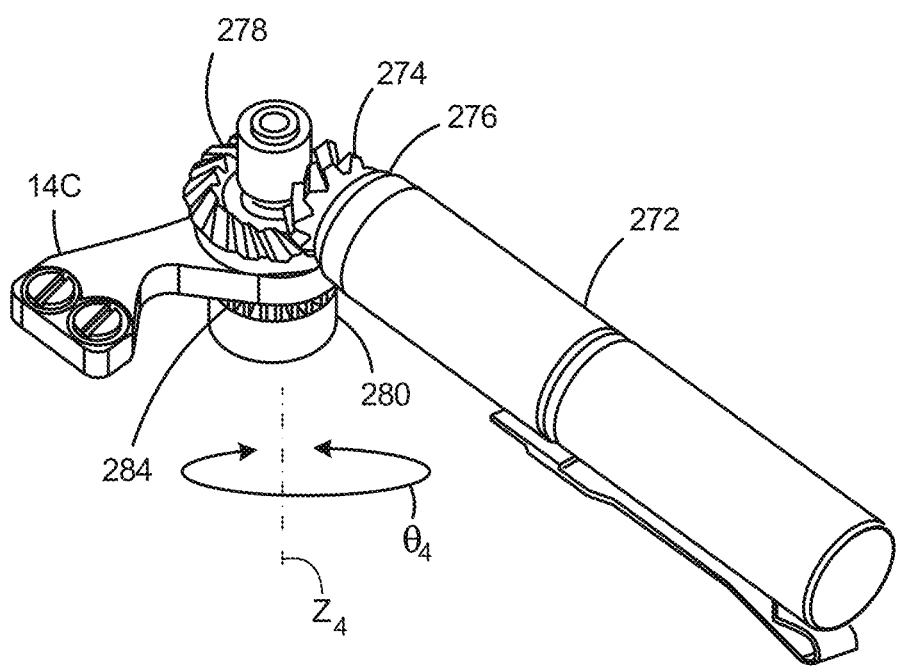
FIG. 12D is a perspective view of certain pitch components of the embodiment of FIG. 12B.

As shown in FIG. 12A-12B, the upper arm 14A can have at least one rigid-flex PCB 290 positioned therein. In one embodiment, the PCB 290 is operably coupled to and controls the motors 260, 272 and magnetic encoders (coupled to the holders 270). In these implementations, flex tapes 292 can be used to communicate with the PCB 290, motors 260, 272 and magnetic encoders, as would be appreciated by a skilled artisan. According to another embodiment, at least one connection component is associated with the upper arm 14A. More specifically, in this implementation, a power/communication line and the cautery power line enter through a port (not shown) at the proximal end of the upper arm 14A and exit through a port (not shown) at the distal end, as has been previously described.

As set forth below, each forearm 14B, 16B also has two electrically isolated cautery circuits, enabling both bipolar and monopolar cautery end effectors. Certain embodiments are configured to allow for easy removal and replacement of an end effector (a "quick change" configuration). Further embodiments contain sealing elements that help to prevent fluid ingress into the mechanism.

Figure 13A:
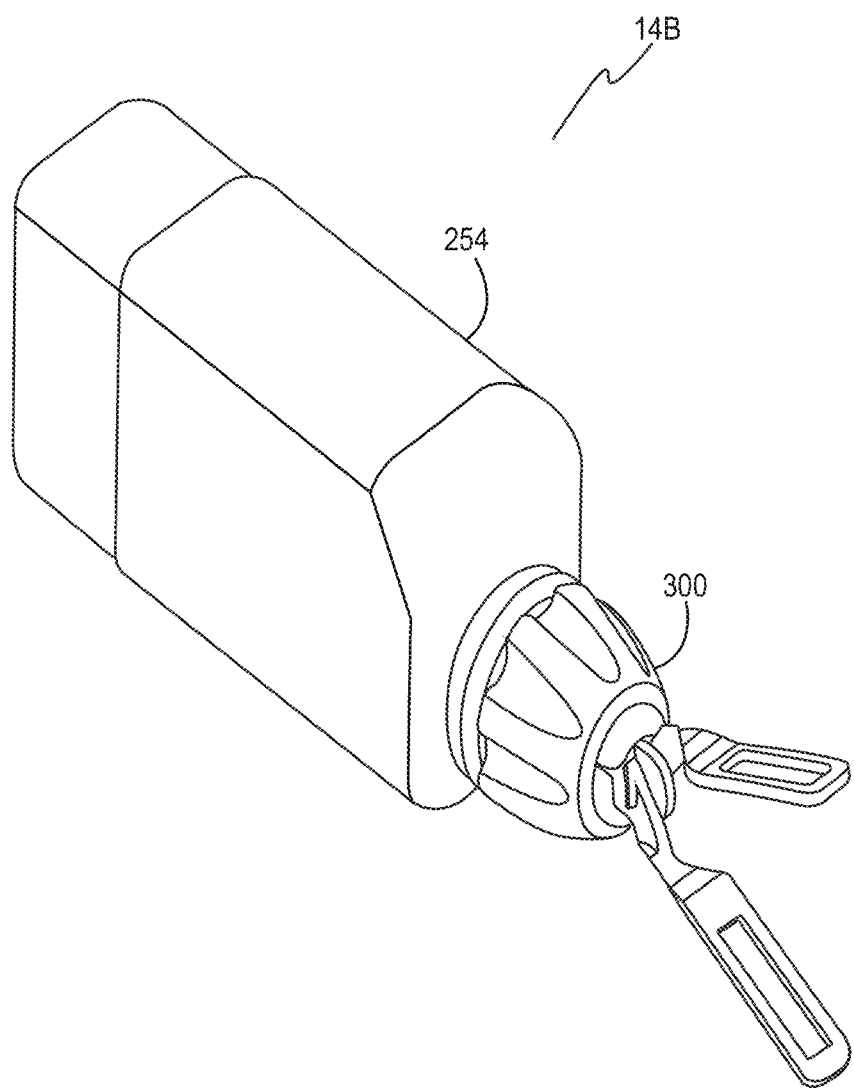
FIG. 13A is a perspective view of a lower robotic arm according to one embodiment.
Figure 13B:
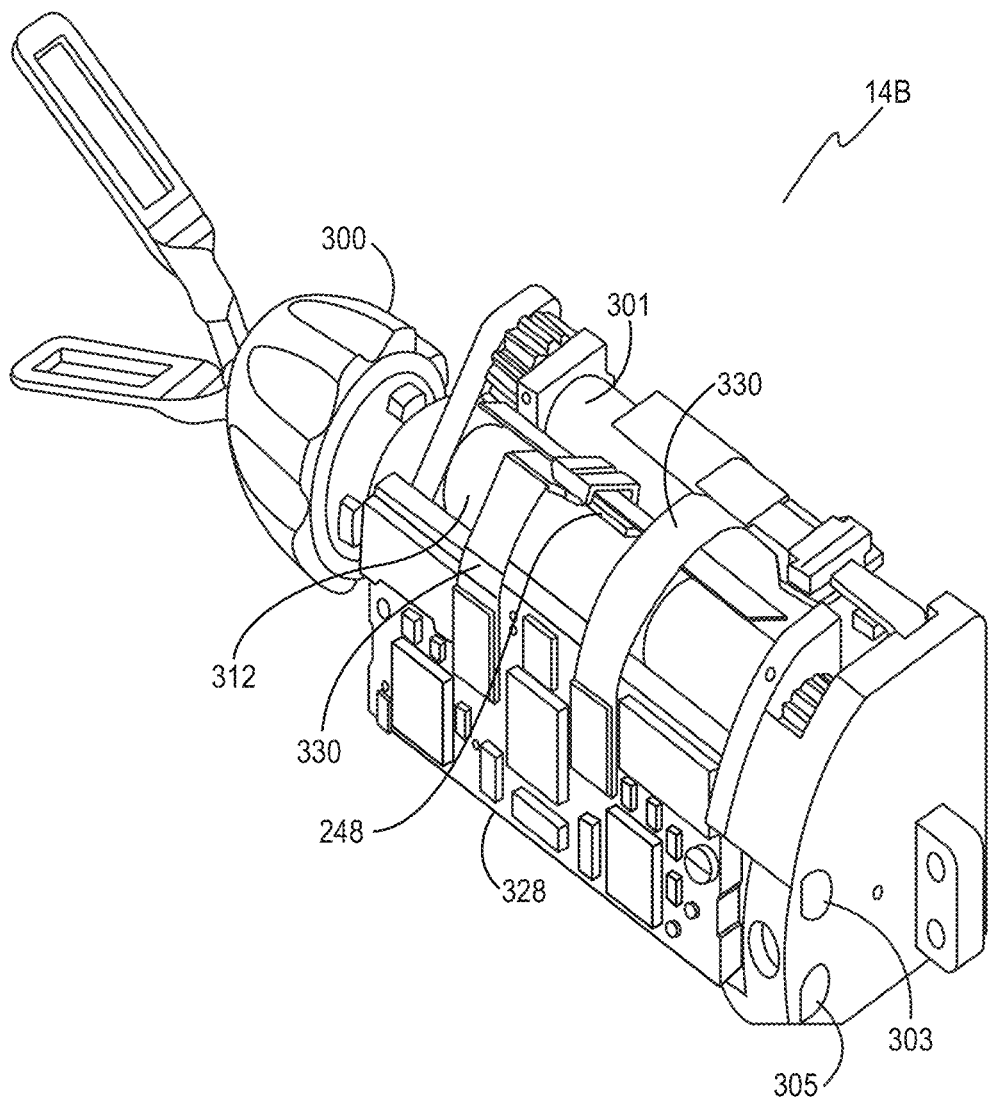
FIG. 13B is a reverse perspective view of the embodiment of FIG. 13A, without the housing.

FIGS. 13A-G depict various embodiments of a right forearm 14B. FIGS. 13B-G show the forearm 14B without its housing 254. The various implementations disclosed and depicted herein include the actuators, drive components, and electronics that can be used to accomplish both tool roll and tool drive (open/close action), as will be described in further detail below. As set forth below, the forearm 14B also has two electrically isolated cautery circuits, enabling both bipolar and monopolar cautery end effectors. Certain embodiments are configured to allow for easy removal and replacement of an end effector 300 (a "quick change" configuration). Further embodiments contain sealing elements that help to prevent fluid ingress into the mechanism. As shown in FIG. 13B, a power and communications lumen 303 and cautery lumen 305 can be used to allow wires (not shown) to be routed from the body 12 to the forearm.

According to one implementation, certain of the internal components depicted in FIGS. 13A-G and 14A-F are configured to actuate rotation at the end effector 300 around axis $Z_5$ (as best shown in FIG. 10), which is parallel to the longitudinal axis of the right forearm 14B. This rotation around axis $Z_5$ is also referred to as "tool roll."

The rotation, in one aspect, is created as follows. As best shown in FIG. 14B, an actuator 301 is provided that is, in this implementation, a motor assembly 301. The motor assembly 301 is operably coupled to the motor gear 302, which is a spur gear in this embodiment. The motor gear 302 is coupled to the driven gear 304 such that rotation of the motor gear 302 causes rotation of the driven gear 304. The driven gear 304 is fixedly coupled to the roll hub 306, which is supported by a bearing 308. The roll hub 306 is fixedly coupled to the tool base interface 310, which has an tool lumen 311 and external threads 310A which are threadably coupled to the end effector 300. Thus, rotation of the driven gear 304 causes rotation of the roll hub 306, which causes rotation of the tool base interface 310, which causes rotation of the end effector 300 around axis $Z_5$ as shown in FIG. 10.

In one embodiment, certain of the internal components depicted in FIGS. 14A and 14C are configured to actuate the end effector to open and close. This rotation of the end effector arms such that the end effector opens and closes is also called "tool drive." The actuation, in one aspect, is created as follows. An actuator 312 is provided that is, in this implementation, a motor assembly 312. The motor assembly 312 is operably coupled to the motor gear 314, which is a spur gear in this embodiment. The motor gear 314 is coupled to the driven gear 316 such that rotation of the motor gear 314 causes rotation of the driven gear 316. The driven gear 316 is fixedly coupled to a female tool spline 318, which is supported by bearing pair 320. The female tool spline 318 is configured to interface with a male tool spline feature on the end effector to open/close the tool as directed.

According to one implementation, the end effector 300 can be quickly and easily coupled to and uncoupled from the forearm 14B in the following fashion. With both the roll and drive axes fixed or held in position, the end effector 300 can be rotated, thereby coupling or uncoupling the threads 310A. That is, if the end effector 300 is rotated in one direction, the end effector 300 is coupled to the forearm 14B, and if it is rotated in the other direction, the end effector 300 is uncoupled from the forearm 14B.

Various implementations of the system 10 are also designed to deliver energy to the end effectors 300 so as to cut and coagulate tissue during surgery. This is sometimes called cautery and can come in many electrical forms as well as thermal energy, ultrasonic energy, and RF energy all of which are intended for this robot. Here electrosurgical cautery is described as an example.

Figure 14D:
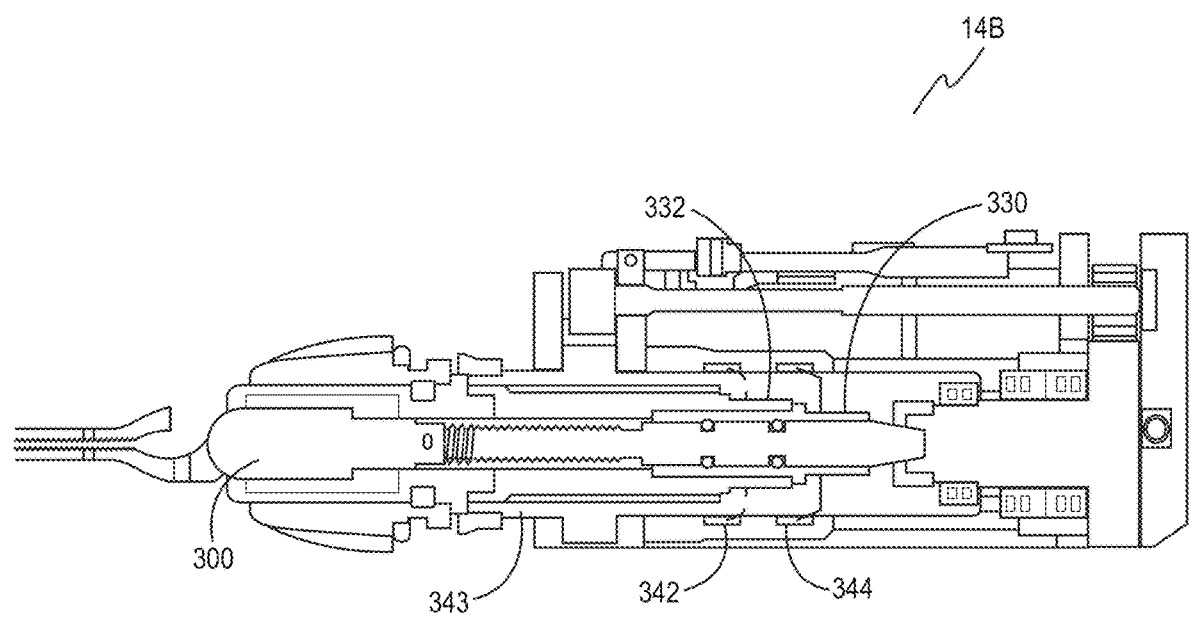
FIG. 14D is a cross-sectional side view of a forearm, according to one embodiment.
Figure 14E:
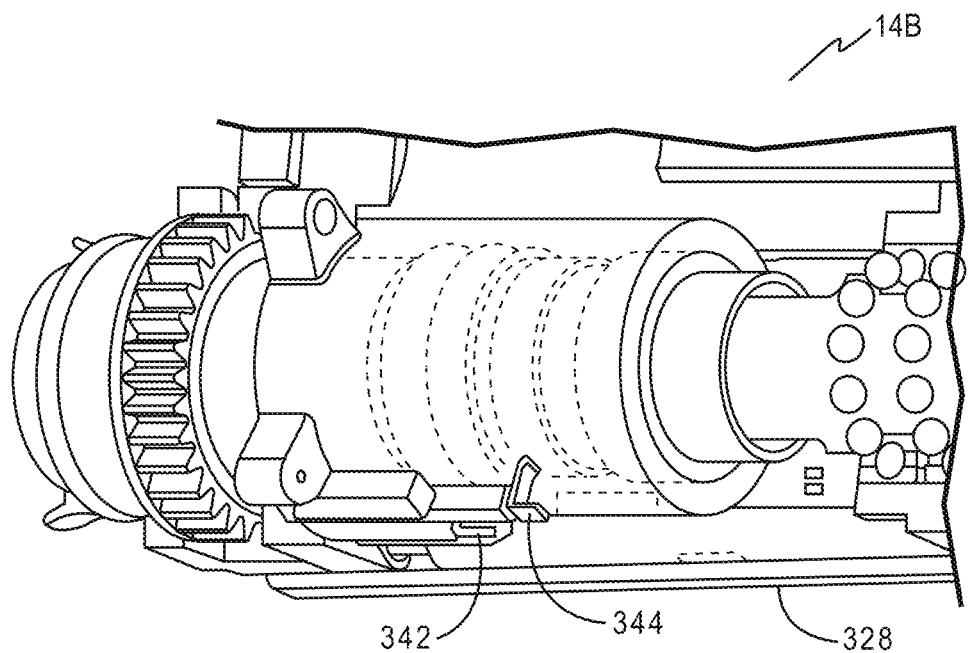
FIG. 14E is a cutaway perspective side view of a forearm, according to one embodiment.
Figure 14F:
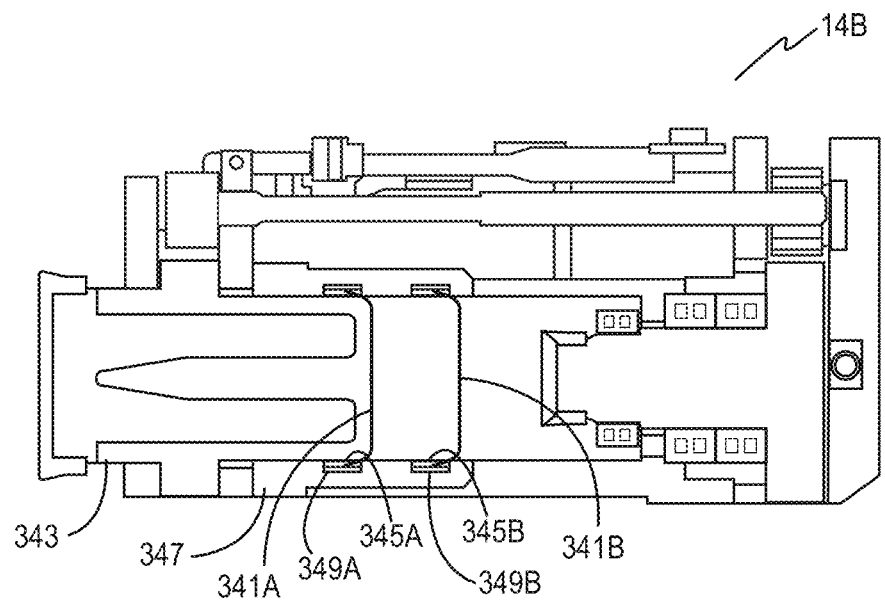
FIG. 14F is cross-sectional side view of a forearm, according to one embodiment.

In accordance with one embodiment, and as shown in FIGS. 14D-F, the forearm 14B has two independent cautery channels (referred to herein as "channel A" and "channel B"), which enable the use of either bipolar or monopolar cautery end effectors with this forearm 14B.

In these implementations, the channel A components are set forth in the forearm 14B as shown. A PCB 328 is electrically isolated from lead A 342 and/or lead B 344 a cautery power line (such as discussed below) that is coupled to an external power source. The PCB 328 is further electrically coupled to at least one flex tape 330A, 330B which is in electronic communication with the motors 301, 312. As such, energizing lead A in the cautery line 342 energizes channel A in the bipolar cautery end effector 300.

As is shown in FIGS. 14E-F, in certain implementations the end effector 300 is disposed within the forearm 14B in a rotor assembly 343A, 343B such that the rotor contacts 341A, 341B and stator contacts or hoops 345A, 345B are in electrical communication with the tool contacts 330, 332. In these implementations, the cautery wire enters through a lumen 305 in the back plate of the forearm (as shown in FIG. 13A). For a bipolar forearm (which uses a pair of conductors), conductor A is soldered to tab A 342 on the stator hoop A. Conductor B is soldered to tab B 344 on the stator hoop 345B. For the monopolar forearm, there is only 1 conductor, so conductor A 342 is soldered to tab A 342 on the stator hoop 345A and the other stator hoop 345B has no connection.

In various implementations, the stator assembly 347 contains the two stator hoops 345A, 345B. The assembly 347 is fixed to the forearm 14B and does not move. The rotor assembly 343 contains two rotor rings 341A, 341B. The rotor 343 is held concentric to the stator 347 through a bearing assembly (not shown) and is free to rotate within the stator 347. Each rotor ring 341A, 341B has a pair of leaf spring contacts (best shown in FIG. 14F at 349A, 349B) which maintain electrical contact to the stator rings 345A, 345B as would be the case for a slip ring.

In these implementations, the rotor rings 341A, 341B extend into the rotor assembly, and the end effectors have a corresponding pair of tool contacts 330, 332 disposed toward the proximal end. These tool contacts 330, 332 contacts can also have leaf spring protrusions.

In use, when the end effector 300 is properly seated within the rotor 343, the leaf spring protrusions of the end effector tool contacts 330, 332 press against the internal circumference of the rotor rings 341A, 341B, so as to form an electrical connection. Additionally, the rotor can have as "arrow shaped" protrusions along its internal surface, to create a lead in, so it is self aligning when you install the tool, while the end effector can have matching cut outs. In these implementations, when the end effector is inserted the protrusions and cut outs mate, such that they form a torque transfer feature between the end effector and the rotor assembly. In this way, when the rotor spins via the roll motor, the end effector spins with it. Thus there is no relative motion between the rotor assembly and the end effector 300.

Figure 15A:
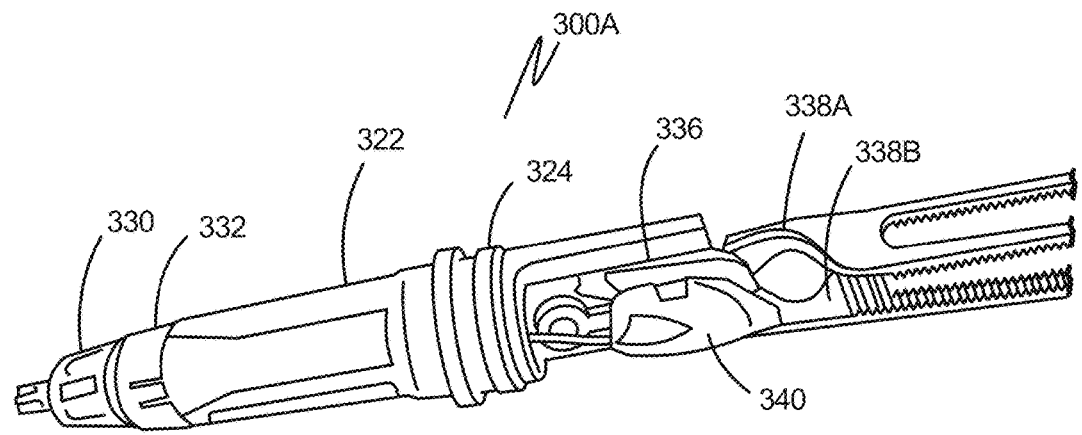
FIG. 15A is a perspective view of an end effector, according to one embodiment.
Figure 15B:
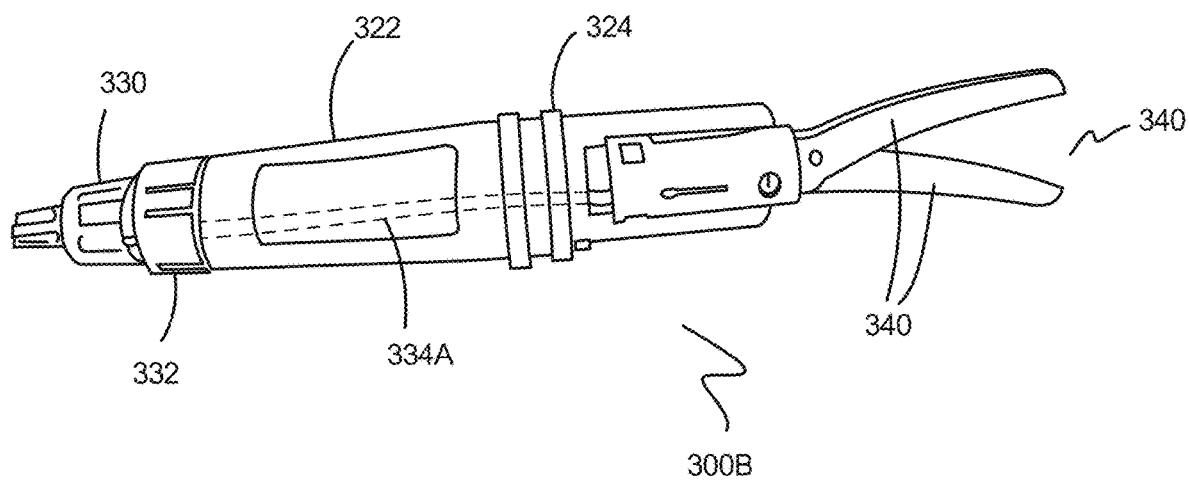
FIG. 15B is a perspective view of an end effector, according to one embodiment.

In one implementation, as shown in FIGS. 15A-B the forearm 14B can be fitted with an insertable bi-polar cautery tool (300A in FIG. 15B), or an insertable mono-polar cautery tool (300B in FIG. 15A) designed for single or multiple use.

In these implementations, the end effector 300A, 300B has at least one fluidic seal interface that helps to prevent fluid ingress into the forearm 14B. One such mechanism is a single-piece housing 322 according to one embodiment. As best shown in FIG. 15A-B the housing 322 can have an O-ring 324 positioned in a groove defined in the housing 322.

In the specific embodiment of the bi-polar tool 300A of FIG. 15A, there are two bronze contacts 330, 332 at the proximal end of the tool 330A. When inserted, these contacts 330, 332 interface with wipers that make an electrical connection between the robot and the tool 300A. As has been previously described, for example in U.S. patent application Ser. No. 14/212,686, which has been incorporated by reference in its entirety, a wiper is a tensioned component that supported on one end by a mechanical strut. An insulating insert is positioned between the wiper and the mechanical strut. At its free end, the wiper is supported by a preloader. Based on this configuration, the wiper is loaded or urged (like a leaf spring) against tool base interface and thus is electrically coupled to the tool base interface. The tool base interface is mechanically coupled to the end effector 28A and electrically coupled to channel B of that end effector. In these implementations, the wipers and contacts 330, 332 are designed so that relative tool motion (tool roll or end effector roll) can occur while maintaining electrical contact between the wiper and contact. These two independent contacts 330, 332 are then connect to each of the jaws respectively, such as by solid copper wires 334. The tools are kept electrically isolated from one another using several techniques including a non-conductive divider 336. The electrical energy is then delivered to the tissue held between the two jaws 338A, 338B. In this implementation, a jaw guide 340 is also provided.

In the specific embodiment of the bi-polar tool 300B of FIG. 15B, there are two bronze contacts 330, 332 at the proximal end of the tool 330B. When inserted, these contacts 330, 332 interface with wipers that make an electrical connection between the robot and the tool 300B. Monopolar energy from the generator (described in relation to FIGS. 16A-B) flows via one electrical connection to the tool 300B so that potential energy exists at the tool tip 340. The energy then returns to the generator through the surgical target via the return pad. The cables can contain connectors so as to simplify use and handling of the robot. This figure shows one additional feature in that the outgoing energy is transmitted through a shielded cable and the shield may or may not be connected to the return path. Having the shield connected to the return pad can be a safety feature in that it prevents energy leakage to the patient. Here leaked energy would be very likely to be collected by the shield and safely returned to the generator.

Figure 16A:
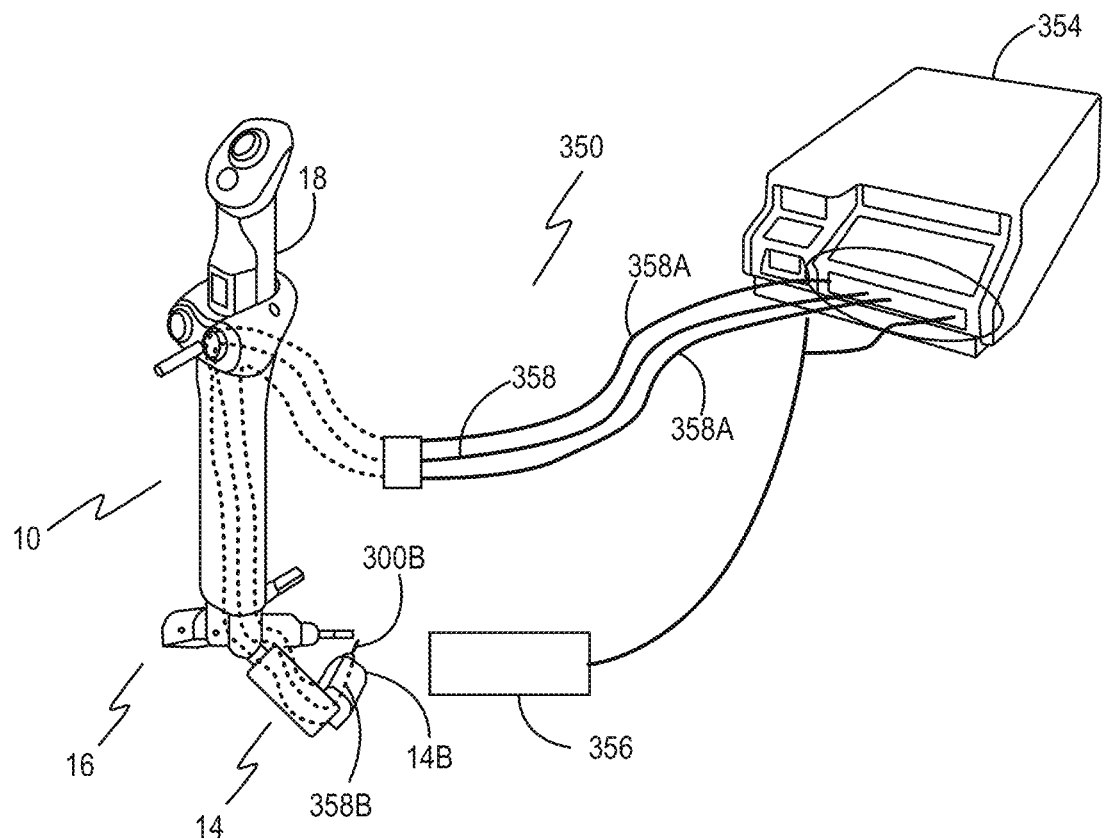
FIG. 16A is a schematic view of a monopolar cautery connection, according to one embodiment.
Figure 16B:
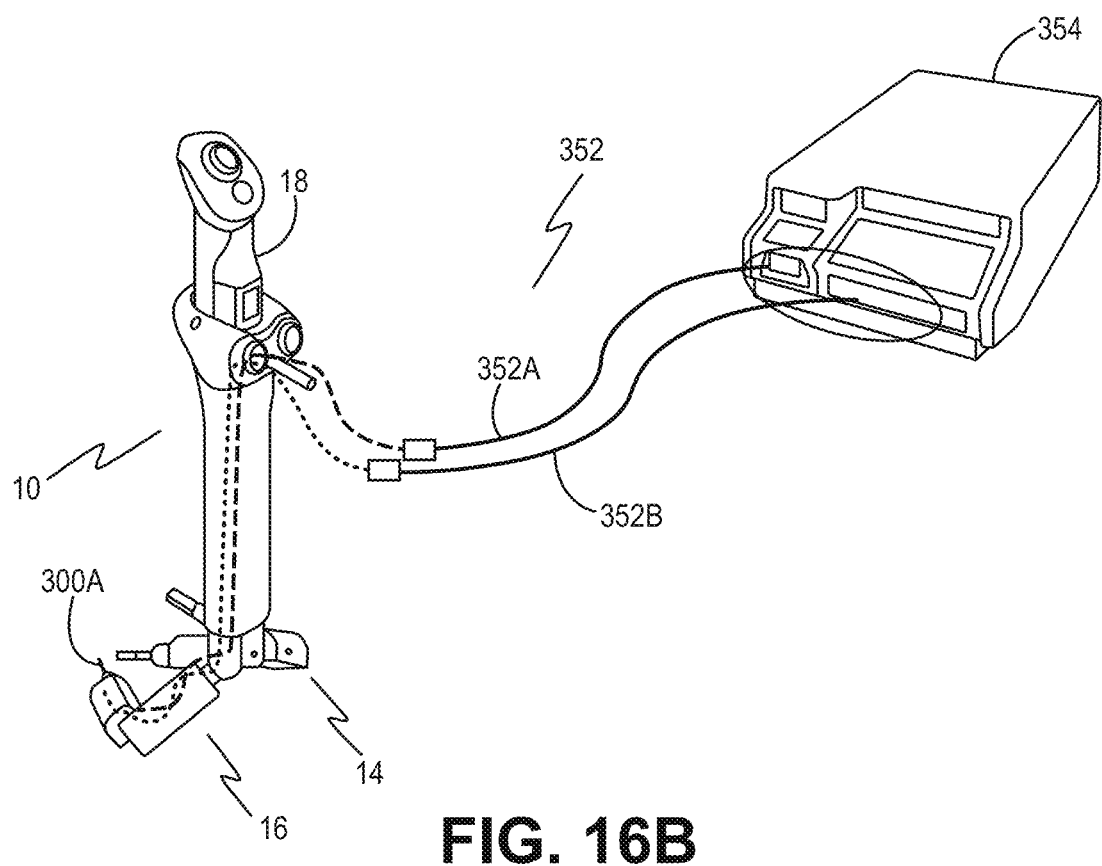
FIG. 16B is a schematic view of a bipolar cauter connection, according to one embodiment.

Various implementations of the system have a monopolar cautery power line 350 (as shown in FIG. 16A) and/or bipolar cauter power line 352 (as shown in FIG. 16B) in electrical communication with an at least one external cautery generator 354 and the respective monopolar 300B and bipolar 300B end effectors. In the implementation of FIG. 16A, the monopolar cautery line 352 is a single coaxial cable 352 which also in electrical communication with a return pad 356 for placement elsewhere on the patient's body. In these implementations, a shield 358A can be provided around the central conductor 358. In various implementations, the shield 358A can extend the length of the central conductor 358 from the generator 354 into the body 12 so as to terminate distally (shown at 358B) in the forearm 14B. In certain implementations, a shield tie 360 is provided, which electrically ties the shield 358 to the return pad 356 and/or electrical generator 354 to prevent radiation from escaping, as would be understood by the skilled artisan.

In the implementation of FIG. 16B, a bipolar power line 352 provides electrical communication between the bipolar cautery lines 352A, 352B and the external cautery generator 354. In various implementations, the monopolar 350 and/or bipolar lines 352A, 352B can connect directly to the body 12 or be connected by way of a "pigtail" 360A, 360B, 360C, as has been previously described.

Figure 17A:
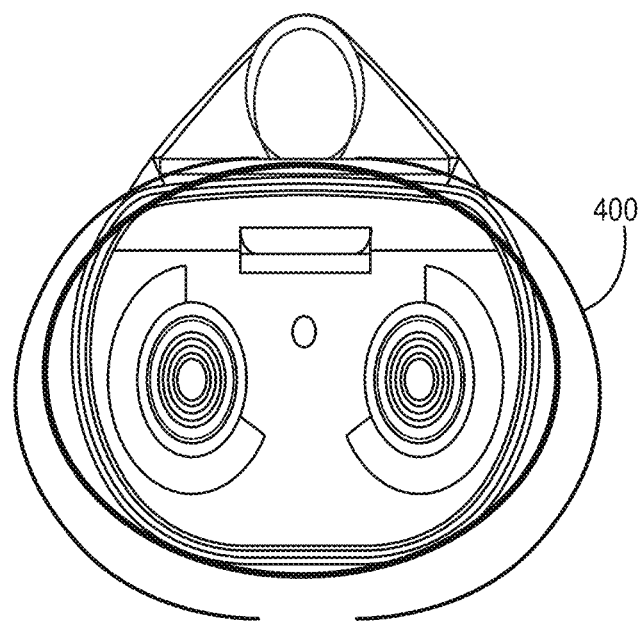
FIG. 17A is top view of one implementation of the device within a sleeve, according to one embodiment.
Figure 17B:
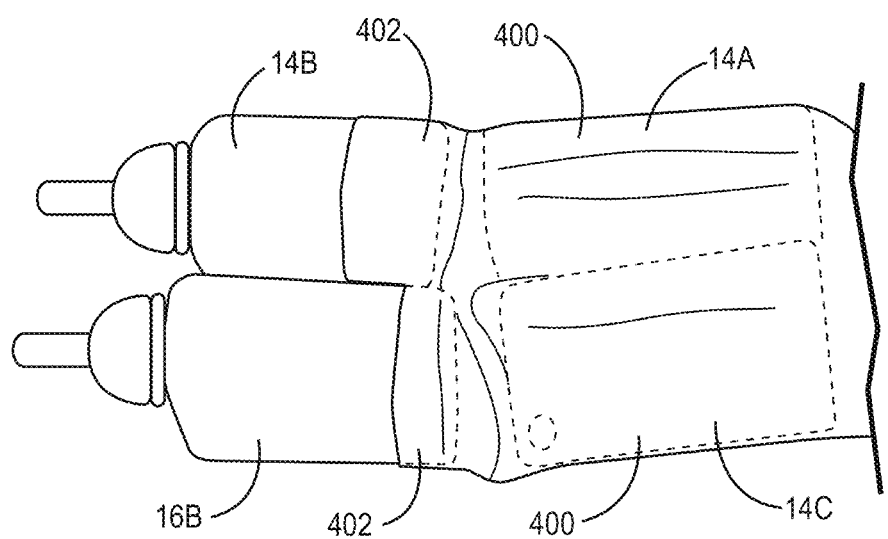
FIG. 17B is a side perspective view of the arms of the device disposed within sleeves, according to one embodiment.

As shown in FIG. 17A, another fluidic seal can be provided according to another embodiment in the form of a flexible membrane 400 (or "sleeve") disposed on the exterior of the arms 14, 16. As shown in FIG. 17B, in certain implementations the membrane 400 is attached at the distal end end 402 to the forearm housing 14B, 16B. This membrane 400 serves to provide a fluidic seal for the internal components of the arms 14, 16 against any external fluids. In one implementation, the seal is maintained whether the end effector 300 is coupled to the forearm 14B, 16B or not.

It is understood that large or "bulky" membranes can interfere with the operation of the camera component 18, particularly for membranes 400 having a belt, as has been previously described. In various implementations, the presently disclosed membrane 400 addresses camera interference. As discussed herein in relation to FIGS. 18A-C through 22C, in certain implementations, the membrane 400 can be permanent, while in alternate implementations, and as shown in FIG. 23A-C, the membrane 400 can be disposable. Alternatively, the membrane 400 can be replaced with a metallic bellows, as has been previously described.

In various implementations, the sleeves 400 can be fabricated by cutting a pattern out of a thin film extrusion, such that a 2D pattern is cut out of a flat piece of plastic and the sleeve is then formed by bonding the 2D pieces together, such as by ultrasonic welding. Alternatively, thermal bonding or adhesives may be used to create the sleeve. In yet a further alternative, a molding process may be utilized to create these sleeve, as has been previously described. This can include dip molding, injection molding, or other known molding options. It is understood that the permanent sleeves can be made of thicker plastic or other material than disposable sleeves to enhance durability.

As is shown in FIGS. 18A-C, in certain implementations, a permanent membrane 400 is disposed over each of the arms 14, 16. In these implementations, the membrane has a rigid termination component 404 at the distal end 402. In certain implementations, and as shown in FIG. 18C, the termination component 404 can use an internal static seal 404A that clips to snap into place and seal with the forearm housing 14B, 16B. In alternate implementations, the membrane 400 can be bonded directly to the forearm housing 14B, 16B at the distal end 402 using UV cured bio-compatible epoxy. In yet further implementations, the distal end 402 can be attached to the forearm housing using mechanical capture between the forearm housing and forearm chassis sub-structure (as is described at the proximal end in relation to FIGS. 19A-C)

Turning to the implementations of FIGS. 19A-C, at the proximal end 406, an O-ring assembly 408 can be used to "pinch" the membrane 400 into a corresponding groove 410 in the body 12. As is shown in FIG. 19C, in these implementations, an outer body housing 412 can be provided over the attached membrane 400. In alternate implementations, the membrane 400 can be bonded directly at the proximal end 406 using UV cured bio-compatible epoxy.

Figures 20A, 20B:
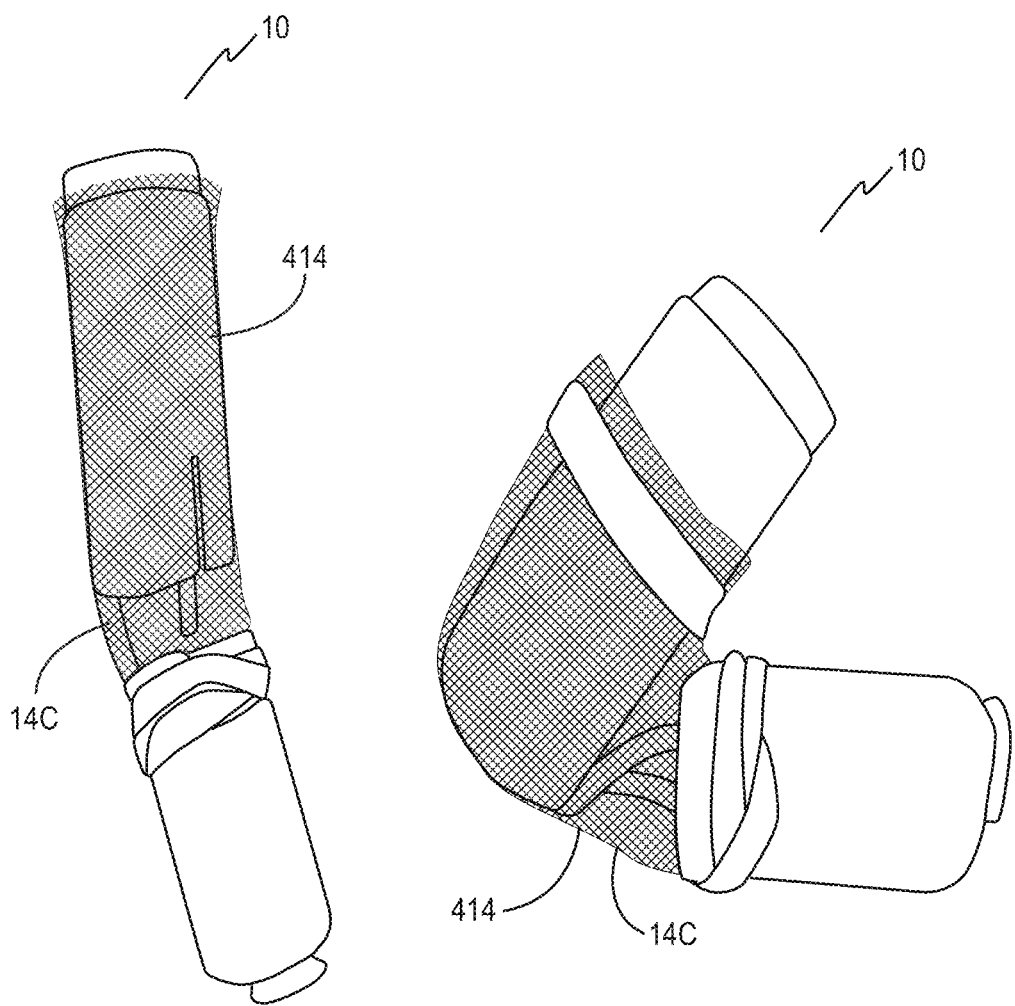
FIG. 20A is a perspective view of a device arm inside a sleeve and in an extended position, according to one embodiment.
FIG. 20B is a perspective view of the embodiment of FIG. 20A in a bent position.

In further implementations, and as shown in FIGS. 20A-20B, a flex-mesh component 414 can be used in conjunction with the membrane (not shown) to prevent "sleeve shear" in highly articulated elbow joints 14C. In these implementations, the mesh 414 ensures that the sleeve does not collapse into the pinch zones created by the arm joints, such as the elbow 14C and shoulder (generally 26, 28).

Figure 21A:
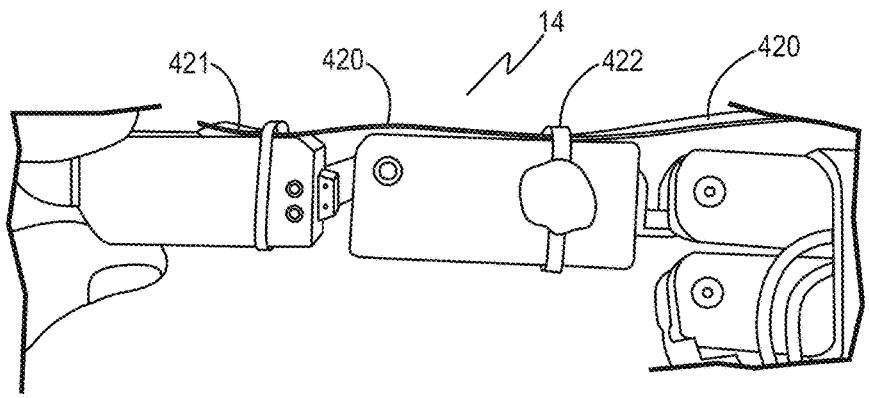
FIG. 21A is a front view of a device arm having a semi-rigid slide guide, according to one embodiment.
Figure 21B:
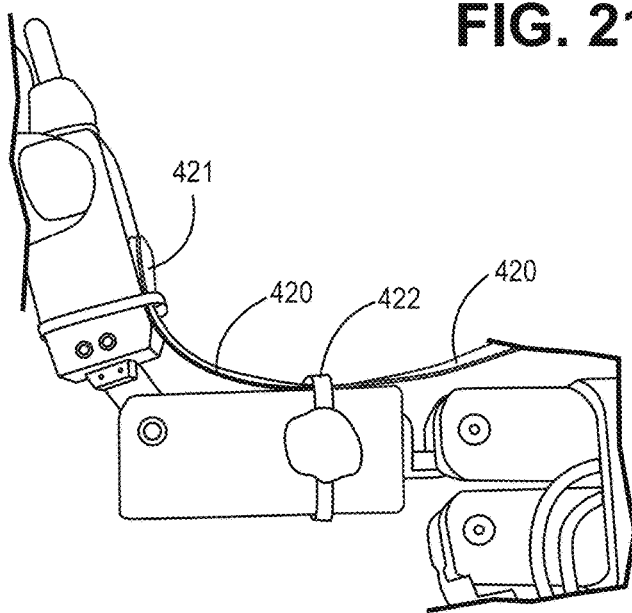
FIG. 21B is a side view of the implementation of FIG. 21A in a bent position.
Figure 21C:
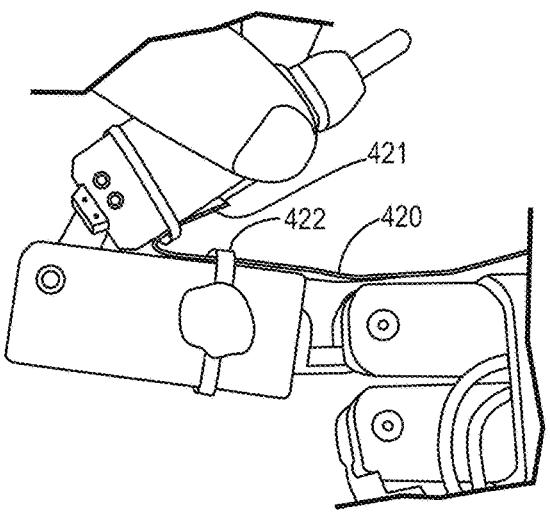
FIG. 21C is a side view of the implementation of FIG. 21A in a further bent position.

In the implementations of FIGS. 21A-C, a semi-rigid slide guide 420 can be used to prevent sleeve shear in the permanent membrane 400. In these implementations, the slide guide 420 extends the length of the membrane (not shown) so as to prevent the membrane from entering the space between the joints of the arm (described above). In various implementations, the semi-rigid guide 420 can be made of thin teflon, delrin, or other flexible, low friction polymers.

In certain implementations, and as shown in FIGS. 21A-21C, the semi-rigid guide 420 is fixed 421 at one location, either at the forearm 14B as shown, or on the upper arm (not shown), so as to allow the guard to move linearly relative to the arm if necessary. In the implementations of FIGS. 21A-21C, the semi-rigid guide 420 is disposed within a guide bushing 422 at the opposite end (here, the proximal end). It is understood that this allows the sliding of the guide as the robot articulates, and creates a moving barrier to prevent the sleeve from entering the pinch zones.

Figure 22A:
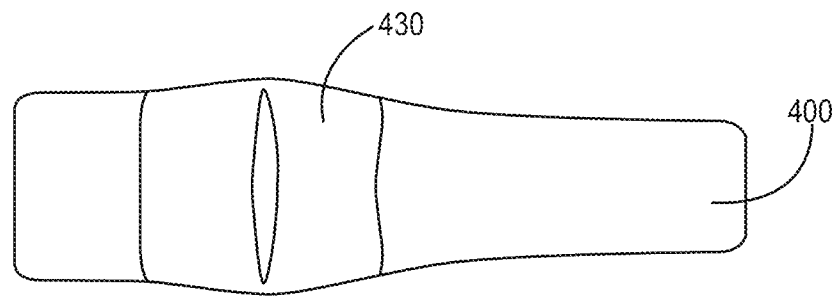
FIG. 22A is a front view of a sleeve having an "outer box" pleat, according to one implementation.
Figure 22B:
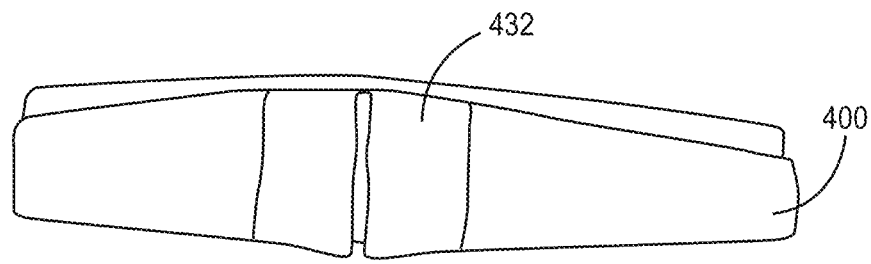
FIG. 22B is a front view of a sleeve having an "inner box" pleat, according to one implementation.
Figure 22C:
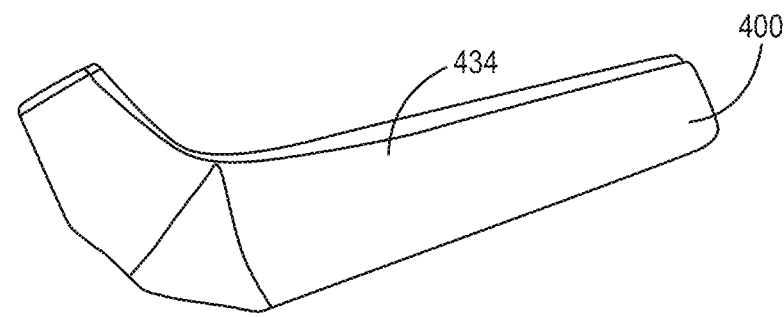
FIG. 22C is a front view of a "bent" sleeve, according to one implementation.
Figure 23A:
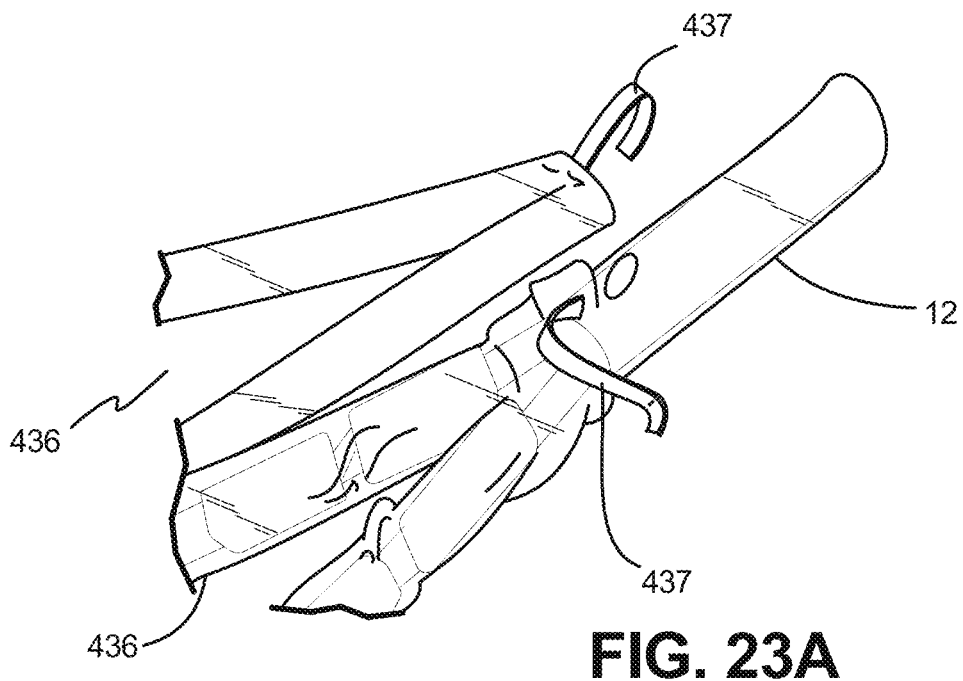
FIG. 23A is a perspective view of a disposable sleeve having an adhesive strip, according to one implementation.
Figure 23B:
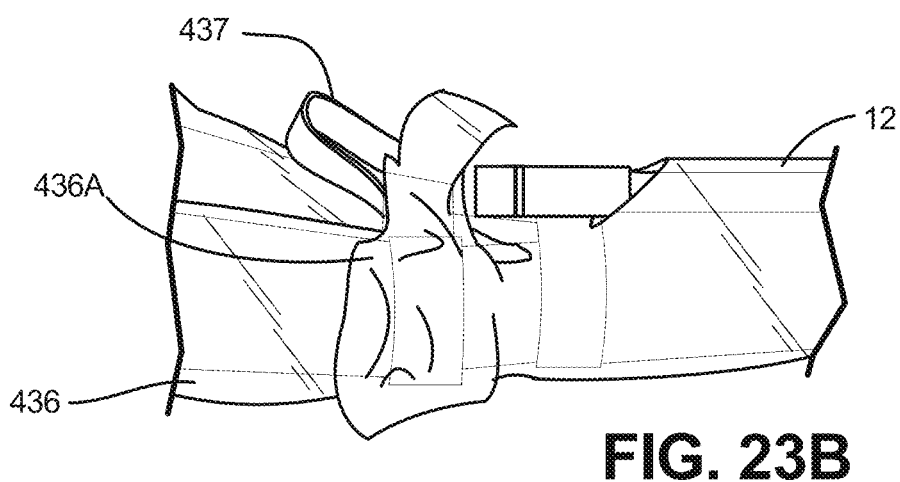
FIG. 23B is a side view of a disposable sleeve having an adhesive strip, according to another implementation.
Figure 23C:
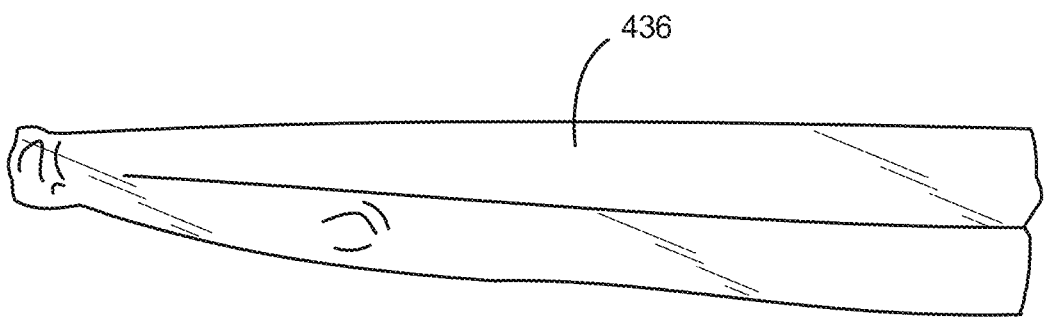
FIG. 23C is a further side view of a disposable sleeve, according to one implementation.

In the implementations of FIGS. 22A-C, sleeve geometry can be optimized in a number of ways. Optimization can be achieved by accounting for the required change in length of the sleeve as the arm goes from a straight to a bent configuration. Several different implementations can be used. As is shown in the implementations of FIGS. 22A-B, the sleeve 400 can be fabricated such that excess material—which is required when the arm is bent—is stored/managed when the arm is straight FIG. 22A depicts a sleeve 400 having an "outer box" pleat 430. FIG. 22B depicts an "inner box" pleat 432. FIG. 22C depicts a "bent" sleeve 434 configuration. Alternatively, as is shown in FIG. 22C, by fabricating the sleeve with a bent configuration 434 such that the bend corresponds to the robots elbow bent to the middle of its range of motion the sleeve was improved to reduce the overall parasitic torque, that is the torque applied to the robot by the sleeve during actuation. Additionally, these implementations can provide an improved "fit," meaning having reduced bunching and/or stretching (as is shown, for example, in FIG. 23B), and can be easier to clean. Each of these optimizations can also be applied to disposable sleeves.

FIGS. 23A-C depict various implementations of disposable sleeves 436. In various implementations, the disposable sleeves 436 must be easy to install and form a barrier to bio-burden and fluids. In certain circumstances, the sleeves 436 may be attached using integrated O-rings that snap into O-Ring grooves, as has been previously described. The sleeves 436 may also be attached using integrated adhesive strips 437 which attach it to the device 10. As shown in FIG. 23B, excessive bunching 436A can occur if the sleeves are not properly sized or optimized. In various implementations, adhesive strips 437 may be optimally located rotationally around the proximal termination section (such as at the waist of robot) to minimize material buildup in critical zones, such as where the camera exits the lumen.

In use, FIGS. 24A-D depict the insertion and operation of the device 10, according to exemplary implementations. As has been previously described and discussed further in relation to FIGS. 27A-C, these steps can be accomplished while the device 10 is visualized, for example on a console, using a laparoscope 448 inserted into the abdominal cavity from another port.

Figure 24A:
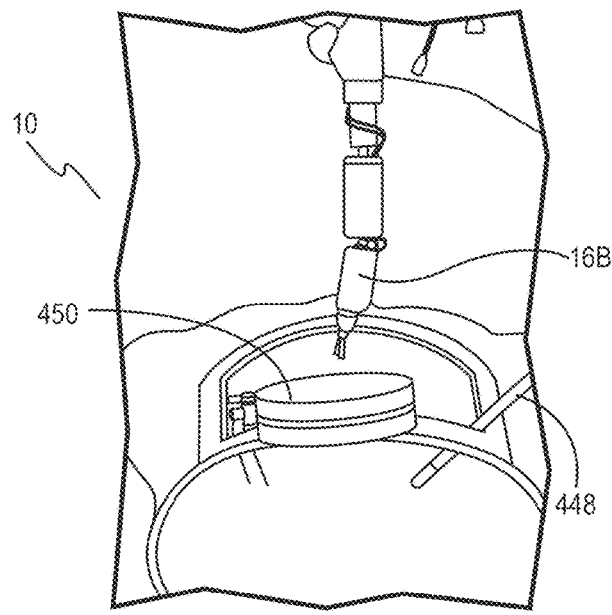
FIG. 24A is a perspective cutaway view of a side of the device and the device port prior to insertion of the device, according to one implementation.
Figure 24B:
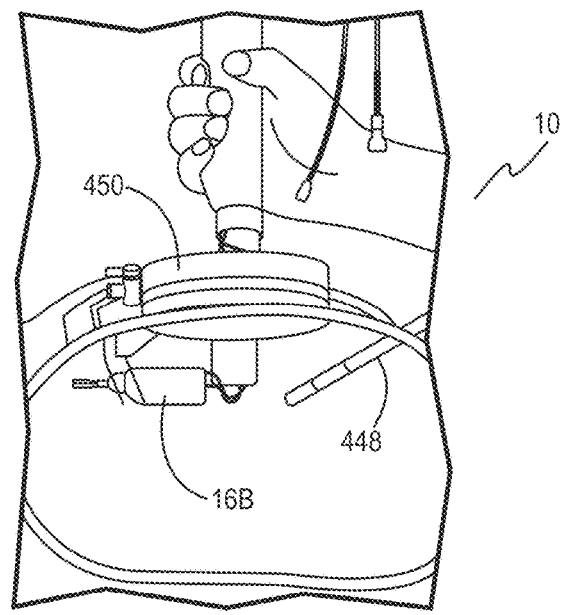
FIG. 24B is a perspective cutaway view of the device of FIG. 24A immediately following insertion.
Figure 24C:
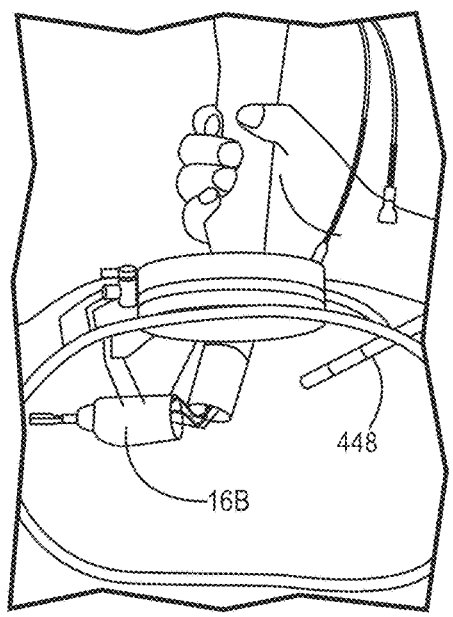
FIG. 24C is a further perspective cutaway view of the device of FIG. 24A following insertion, where the device has been tilted.
Figure 24D:
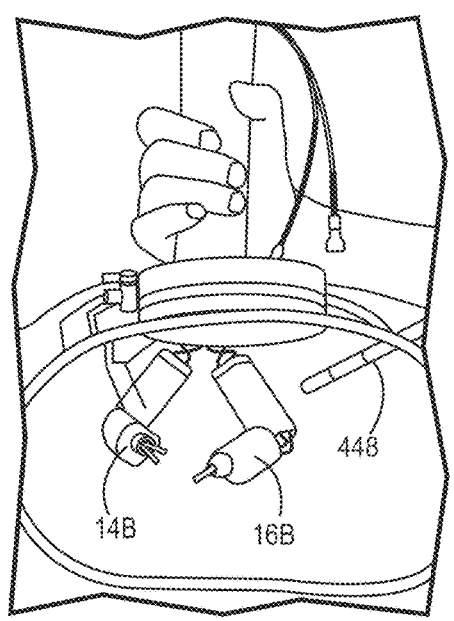
FIG. 24D is a further perspective cutaway view of the device of FIG. 24A following insertion, where the device has been rotated.

As shown in FIG. 24A, during insertion, the device 10 is first held above a gel port 450 that allows for the abdominal cavity to remain insulated while the gel port 450 seals around the irregular shape of the device 10. As shown in FIG. 24B, the device 10 is then is inserted through the gel port 450. The elbows 14C, 16C can then be bent to accommodate further insertion. The device 10 can then be inserted further until the arms 14, 16 are substantially within the abdominal cavity, as best shown in FIG. 24C. This then allows the device 10 to be rotated and moved to the desired position for surgery, as shown in FIG. 24D.

Figure 25A:
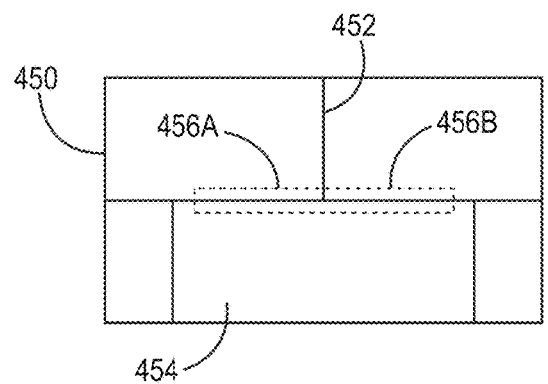
FIG. 25A is a side cross-sectional view of a device port, according to one implementation.
Figure 25B:
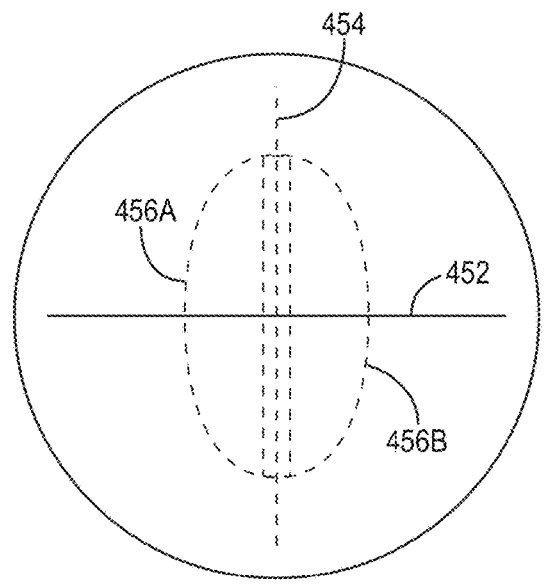
FIG. 25B is a top view of the port of FIG. 25A.

FIGS. 25A-B depicts a gel port 450, according to one implementation. In the embodiment of FIG. 25A, the gel port 450 has first 452 and second 454 openings, or "slits." In certain implementations, the passage of the device 10 into the gel port 450 causes splaying of the arms 14, 16, which can result in patient injury. In these implementations, the slits 452, 454 facilitate the retention of the device 10 in an upright orientation. In certain of these implementations, the gel port 450 has a pair of semi-rigid corals 456A, 456B configured to urge the arms 14, 16 centrally and prevent splaying during insertion.

Figure 25C:
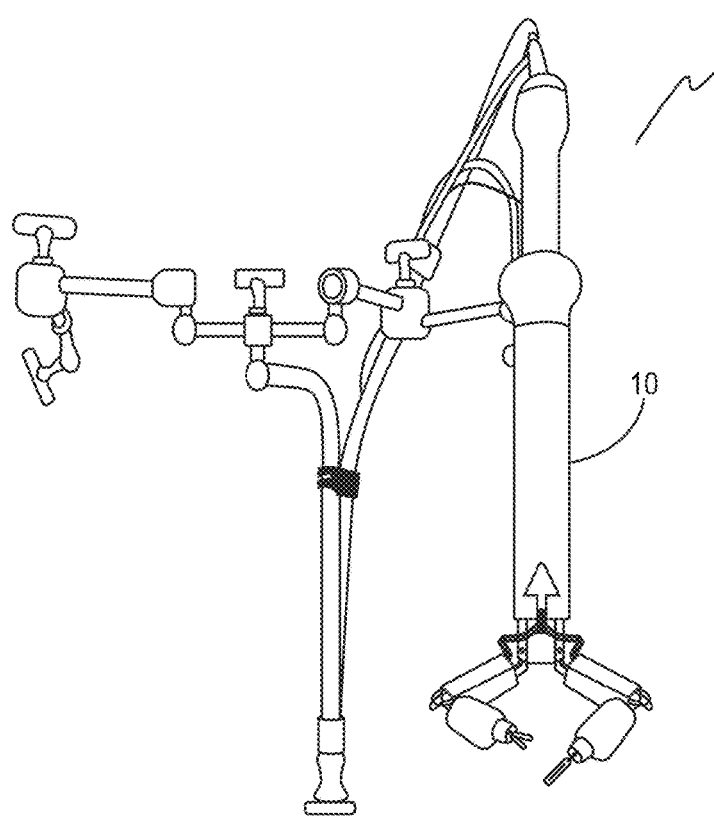
FIG. 25C is a front view of one device implementation attached to a robot support arm, according to one implementation.

As shown in FIG. 25C, In certain implementations the robotic device 10 is clamped to (or otherwise coupled to) the distal end of the robot support arm 470. The proximal end of the support arm 470 is clamped or otherwise coupled to a standard support strut on the operating table. In this embodiment, the support arm 470 has 6 degrees of freedom, which are manually released by a single knob. In use, the user can release the support arm 470 by loosening the knob, move the robotic device 10 to a suitable position, then tighten the knob, thereby rigidizing the arm 470 and fixing the robotic device 10 in place. One example of a commercially-available support arm 470 is the Iron Intern™, made by Automated Medical Products Corp.

Figure 26A:
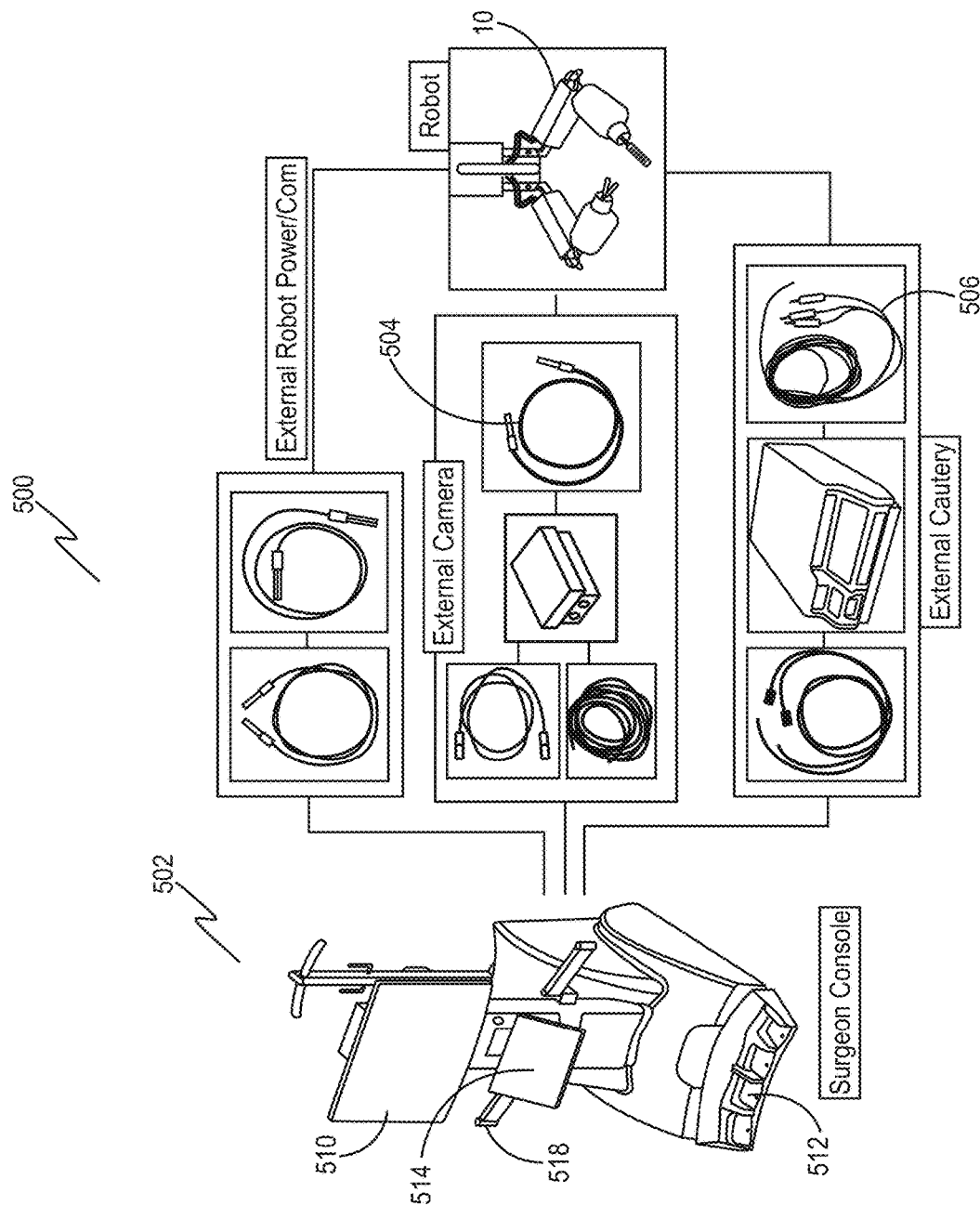
FIG. 26A is a schematic view of one implementation of a robotic surgical device and operations system.
Figure 26B:
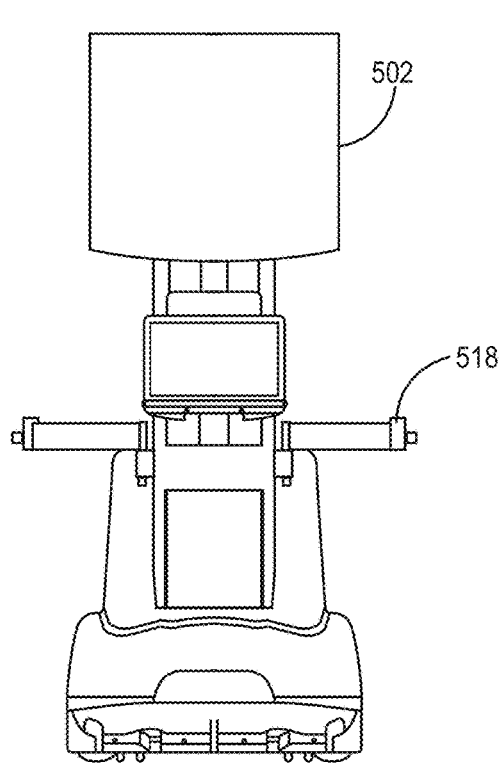
FIG. 26B is a front view of a surgical console, according to one implementation.
Figure 26C:
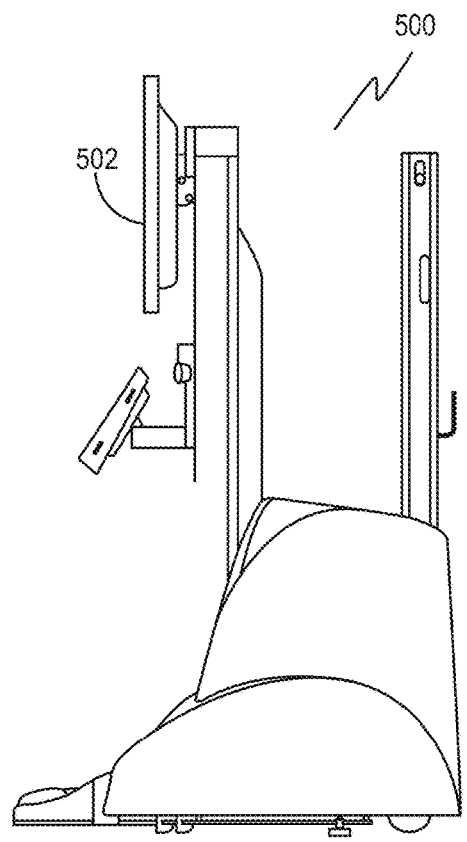
FIG. 26C is a side view of the surgical console of FIG. 26B.
Figure 26D:
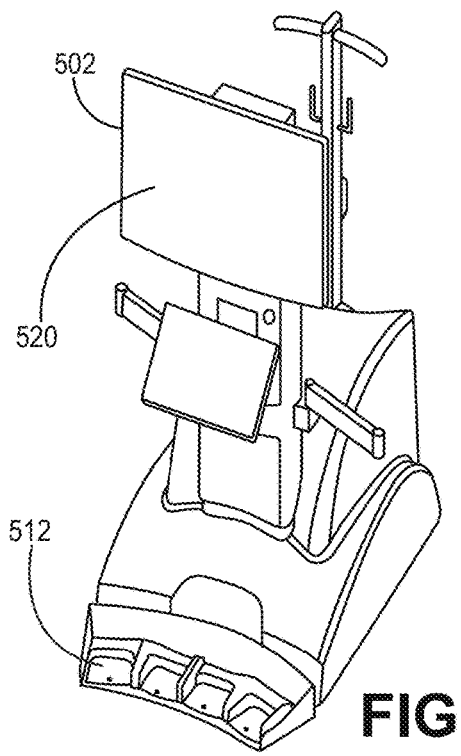
FIG. 26D is a perspective view of the surgical console of FIG. 26B.
Figure 26E:
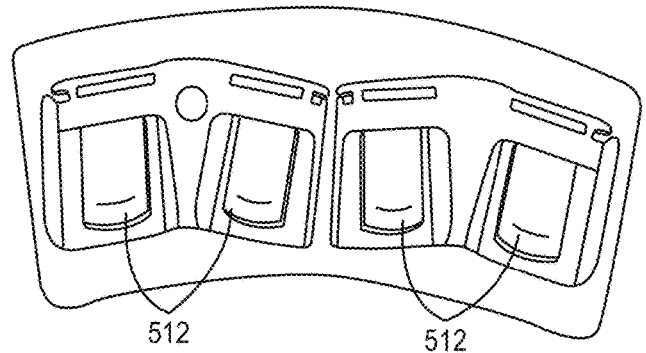
FIG. 26E is a top view of the foot controllers of the surgical console of FIG. 26B.

In use, according to one embodiment as shown in FIG. 26A, the system 500 can operate in the following fashion. A user—typically a surgeon—positions herself at the surgeon console 502. As discussed in further detail below, the console 502 can have a visual display 510, a touch screen 514 and input components such as foot input devices (also called "foot controllers") 512, and hand input devices (also called "hand controllers") 518. The user can operate the system 500 by operating the hand controllers 518 with her hands, the foot controllers 512 with her feet, and the touch screen (also referred to herein as the "graphical user interface" or "GUI") 514 with her hands, while using the visual display 510 to view feedback from the camera 18 relating to the robot 10 positioned in the target cavity of the patient. The console 502 is coupled to the robot 10 and its components in three different ways in this embodiment. That is, the console 502 is coupled directly to the robot 10 itself via the cable 502 that carries both power and communications between the console 502 and the robot 10. Further, the console 502 is also coupled to the camera 18 on the robot 10 via the cable 504 that carries both power and communications between the console 502 and the camera 18. In addition, the console 502 is also coupled to the cautery end effectors 300A, 300B on the robot 10 via the cable 506 that carries power and communications between the console 502 and the cautery end effectors 300A, 300B (as discussed above in relation to FIGS. 16A-B). In other implementations, the console 502 can be coupled to the robot 10 via other connection components and/or via other robot components.

According to one embodiment as best shown in FIGS. 26B-26E, the console 502 allows the user to control the robotic device 10 using the hand controllers 518 and/or foot controllers 512. The hand controllers 518 and the foot controllers 512 can be used to control the arms and other components and functions of the robotic device 10. In various implementations, the device 10 is controlled by using the hand controllers 518 and/or foot controllers 512 to cause the device 10 to move in the same way as the hand controllers 518 and/or foot controllers 512 are moved. More specifically, for example, the right hand controller 518 can be used to actuate the right arm of the robotic device 10 such that the movement of the hand controller 518 causes the right arm of the device 10 to replicate or simulate the same motion. For example, if the right hand controller 518 is extended outward away from the user, the right arm of the device 10 is actuated to extend outward away from device 10 in the same direction. The left hand controller 518 and left arm of the robotic device 10 can operate in a similar fashion. This virtual connection and interaction between the console 502 and the robotic device 10 can be called a tele-operation (or "tele-op") mode.

Figure 27A:
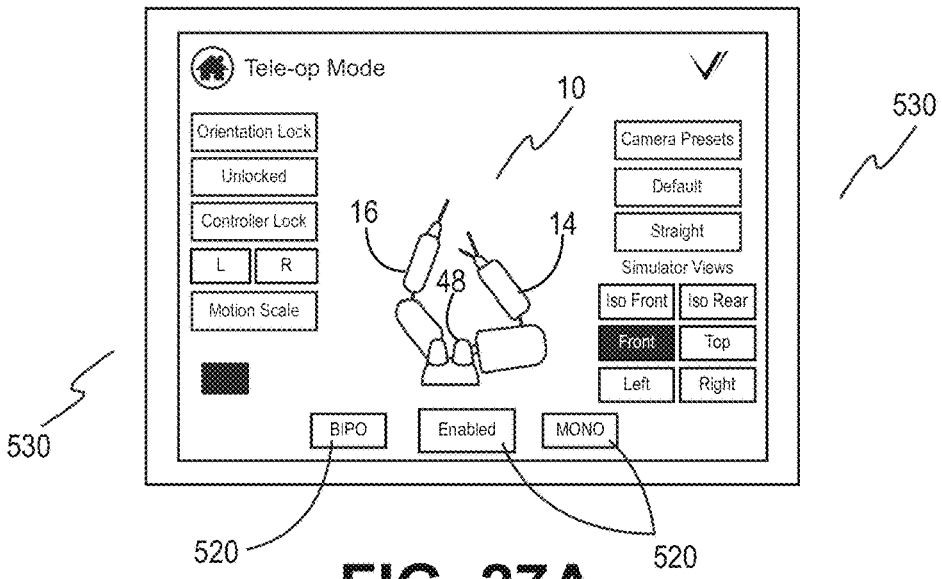
FIG. 27A is a screen view of a graphical user interface on the console, according to one implementation.
Figure 27B:
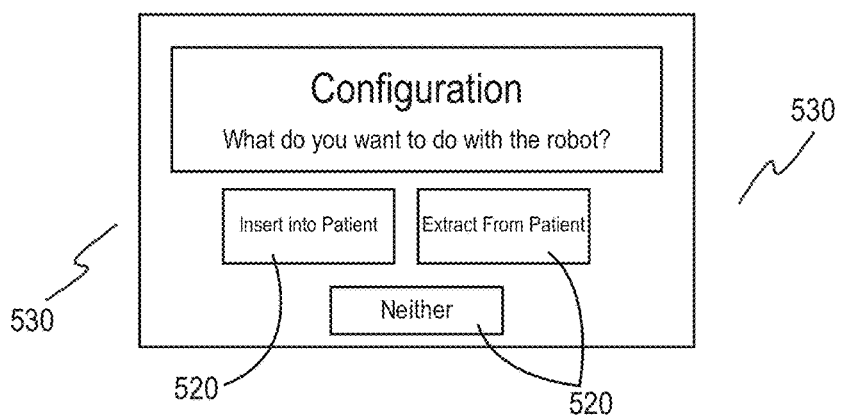
FIG. 27B is a screen view of another graphical user interface on the console, according to one implementation.
Figure 27C:
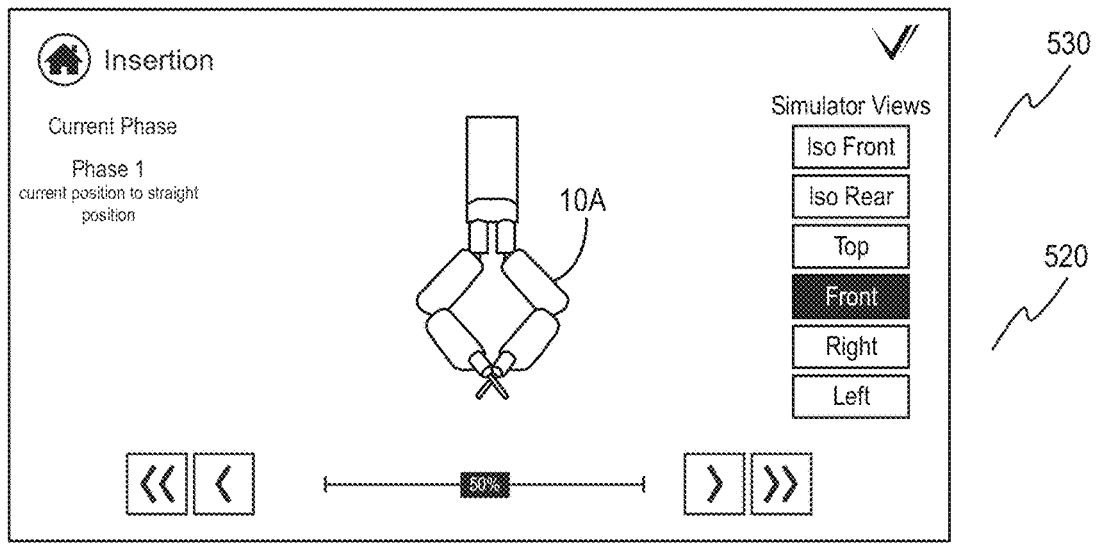
FIG. 27C is a screen view of yet another graphical user interface on the console, according to one implementation.

One embodiment of an exemplary GUI 530 is depicted in FIGS. 27A-C. In this implementation, various buttons 520 are provided which can be used to control the insertion, retraction, and operation of the device 10. More specifically, as shown in FIG. 27B of this embodiment, the user can select the specific operational page to be displayed on the GUI 530. If the user selects the "Insert" button as shown in FIG. 27B, then the insertion page is displayed as shown in FIG. 27A. Thus, the GUI 530 can provide the user with the ability to control settings and functions of the robotic surgical system. In various implementations, the touch screen can include settings for motion scaling, camera position, and indicators that show robot modes (cautery state, GUI state, etc) and the like. Further, in the tele-op mode as shown in FIG. 27A, the display 530 can depict a real-time robot animation (generally at 10) that displays the current configuration of the device 10, including the specific positions of the arms of the device 10.

In certain embodiments, the virtual connection between the console 502 and device 10 as described above can be interrupted using a "clutch." In one specific implementation, the clutch can be activated using a button 520 on the GUI 530. Alternatively, the user can activate the clutch by depressing one of the foot pedals 512. The clutch is activated to break the virtual connection described above, thereby disconnecting the device 10 from the console 502 such that the device 10 and its components enter a "frozen" or "paused" state in which the components of the device 10 remain in the last position the components were in when the clutch was activated and until the clutch is deactivated. This clutch feature can be utilized for several different reasons. For example, the clutch feature can be used in an emergency pausing situation in which the device 10 components are moving toward a position which one or more of the components might damage the internal tissues of the patient and the clutch activation prevents that. In another example, the clutch feature can be used to reset the virtual connection in the same way that a computer mouse is lifted off the mousepad to reset the connection between the mouse and the cursor on the computer screen. In other words, the clutch feature can be used to reposition the hand controllers to a more desirable position while pausing the device 10.

Certain system embodiments disclosed or contemplated herein can also have hand controllers (such as controllers 518 discussed above) that feature haptic feedback. That is, the hand controllers (such as controllers 518) have haptic input devices, which are made up of motors operably coupled to the hand controllers such that the motors can be actuated to apply force to the controllers (such as controllers 518), thereby applying force to the user's hands that are grasping the controllers. This force applied to the user's hands that is created by the haptic input devices is called haptic feedback and is intended to provide information to the user. For example, one use of haptic feedback is to indicate to the user a collision between the robotic arms. In another example, the haptic feedback is used to indicate to the user that the robotic device or one of its components (such as one of the arms) is approaching or has reached its reachable or dexterous workspace.

Figure 28A:
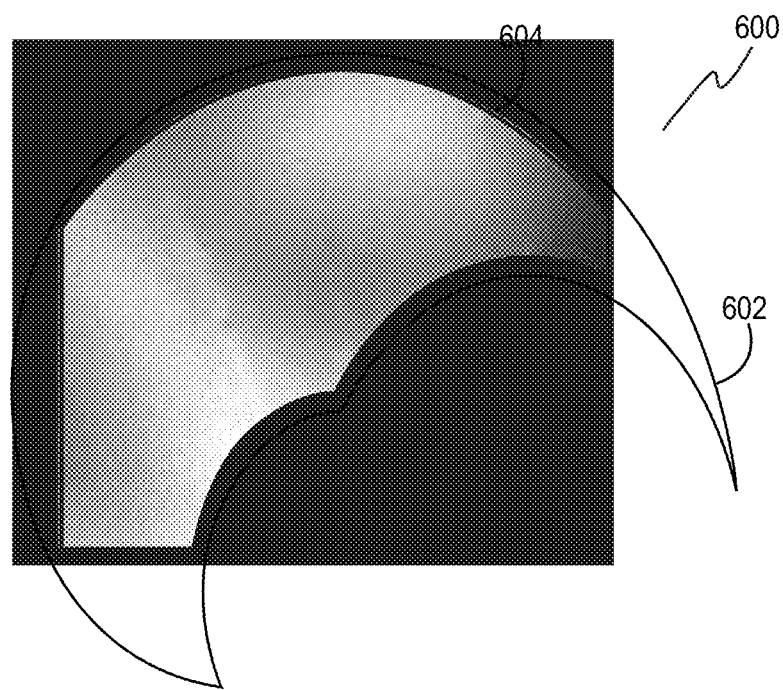
FIG. 28A is a schematic view of the workspace of one arm of a robotic device, according to one implementation.
Figure 28B:
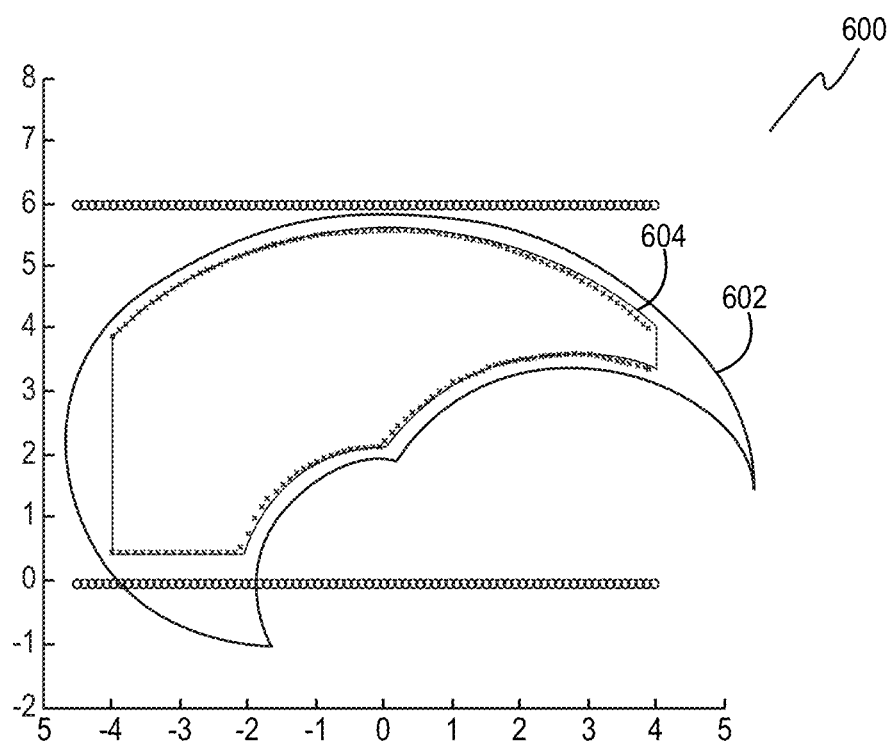
FIG. 28B is a further schematic view of the workspace of one arm of a robotic device, according to one implementation.
Figure 28C:
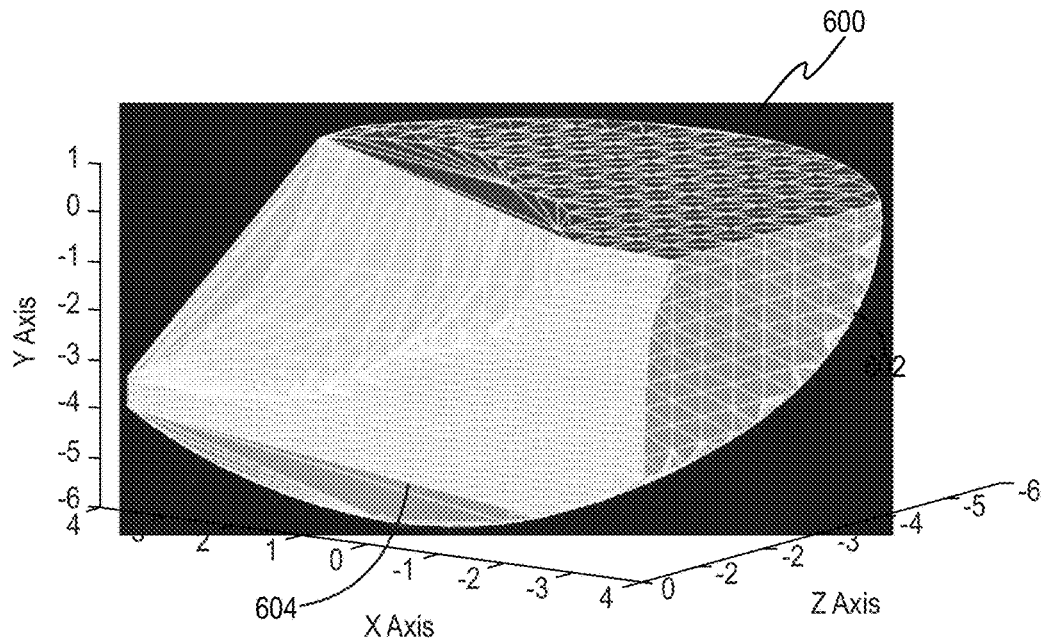
FIG. 28C is yet a further schematic view of the workspace of one arm of a robotic device, according to one implementation.

FIGS. 28A and 28B provide a schematic representation of haptic feedback relating to the dexterous workspace of a robotic arm according to a specific embodiment. More specifically, FIG. 28A represents a two-dimensional "slice" of the workspace 600 of one arm of a robotic device of any system embodiment herein. That is, the image is a representation of the range of motion 600 of the distal end of the robotic arm in two dimensions (the x and y directions) such that it depicts all of the area 600 that the end effector of the robotic arm can reach when the arm can move in those two dimensions and the device body is kept motionless. As is shown in FIG. 28C, this workspace 602 can be extended into three dimensions, as the device 10 is capable of operating in the z-direction as well).

In these implementations, and as best shown in FIG. 28A, the full reachable workspace 600 is made up of both the exterior portion 602 and the interior portion 604 of the workspace 600. The interior portion 604 is the operational workspace 604 of the robotic arm. That is, it is the workspace 604 in which the arm is functional and operates optimally. The outer portion 602 is the undesirable or non-optimal workspace 602 of the robotic arm.

In this specific embodiment as best shown in FIG. 28B, the system has been configured to provide haptic feedback as the end effector of the arm reaches the outer points of the workspace 600. More specifically, the system, or a software component thereof, defines the haptic boundary 604 as the operational workspace 604. When the user moves the robotic arm such that the end effector is inside the haptic boundary 604, the haptic input devices apply no force to the hand controllers, thereby indicating to the user that the robotic arm is in the operational workspace 604. If the end effector of the arm moves outside of the haptic boundary 604 and into the non-optimal workspace 602, the haptic input devices provide force that urges the hand controller, and thus the robotic arm, back toward the closest point on the haptic boundary. In one embodiment, the force applied at the hand controller is proportional to the distance from the haptic boundary such that it feels to the user like a virtual spring is pushing the user's hand (and thus the robotic arm) back inside the boundary 604. Alternatively, it is understood that other models for forces can be created other than proportional distance.

Figure 28D:
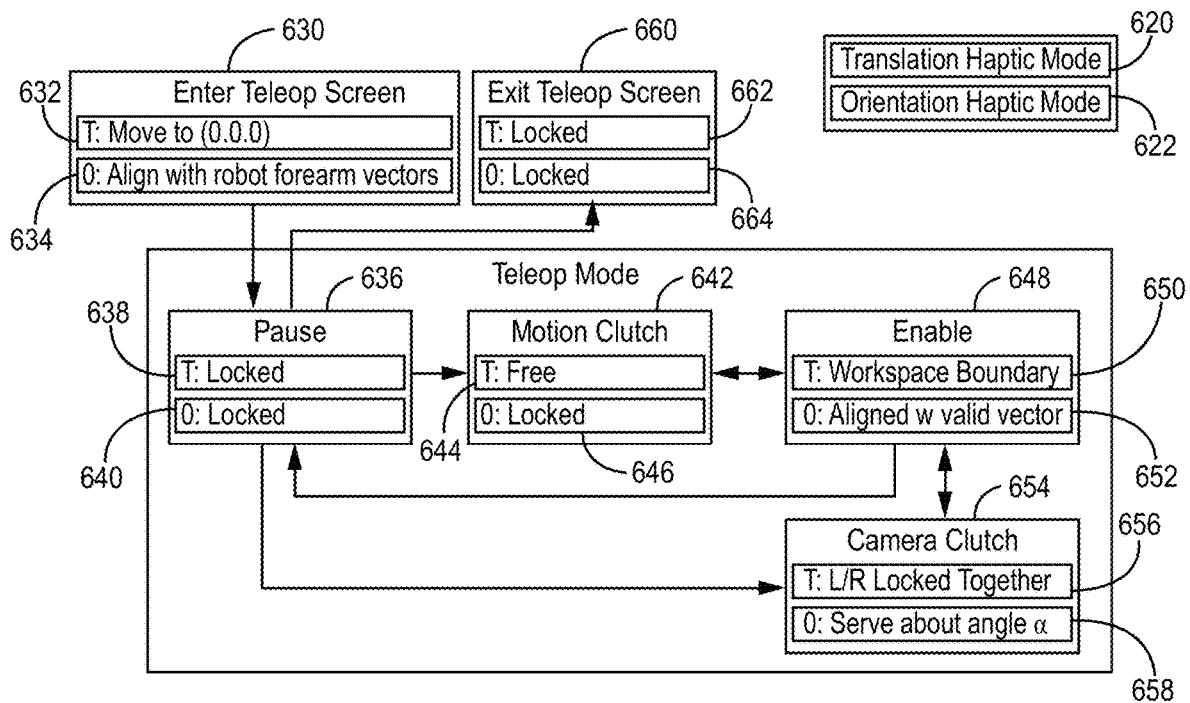
FIG. 28D is schematic depiction of system and device operation, according to one implementation.

Once possible use of the system is shown in FIG. 28D. In this implementation, the user can operate the hand controllers 518 (as shown in FIGS. 226A-E) in translation (box 620) and/or orientation (box 622) modes through a variety of steps. In certain implementations, controllers have seven degrees of haptic feedback relating to the position of the device in the surgical theater. Here, translation mode refers to x-, y-, and z-haptics, while the orientation mode refers to roll, pitch and yaw feedback, and the trigger operation can account for a seventh degree. In certain implementations, it is desirable to lock certain of these feedback movements—such as orientation—while leaving others—such as translation—free to be moved relative to the console. This selective locking allows for gross repositioning of the user's hands and controllers without causing a corresponding movement of the device 10 within the surgical theater.

For example, the user can enter tele-op mode (box 630) such that the haptic input devices (described in detail in relation to FIGS. 26A-27C) are aligned to their center (0, 0, 0) regardless of the position of the device (box 632), while the orientation vectors (box 634) are aligned with the orientation of the device arms 14, 16 with respect to yaw, pitch and roll.

In tele-op mode, these positions are set (boxes 632 and 634), such any movements of the controllers will directly correspond with the movement of the device 10, and any force applied to the device 10 will cause a corresponding force to be applied back to the user through the controllers. However, in certain situations, the user may desire to re-orient the hand controllers relative to the console without causing a corresponding change in the movement of the device.

When the system is paused (box 636) the system is "locked" (boxes 638 and 640), such that the hand controllers 518 are locked in place. No movement or commands to the device 10 are being sent, such that the device 10 holds position regardless of what the user does to the hand controllers, meaning that even if the user overpowers the haptic locks and moves the hand controllers, the robot will not move.

In further implementations, to move the controllers independently, the user can engage the clutch (box 642) so as to disengage the translation of the controllers only (box 644) while the device arms 14, 16 and controllers maintain a fixed orientation (box 646). When the clutch 512 is disengaged (box 648) the robot and hand controllers are then virtually re-connected, so as to again fix translation and orientation between the controllers and device.

In these implementations, the workspace can be defined (box 650) when the device 10 is positioned. As discussed above, the translational movement of the arms and controllers is limited by the workspace boundary (box 650), and the orientation movements are aligned with a valid vector (box 652) to ensure safety and precision.

In certain implementations, the haptic lock can be also interrupted by other functions such as "camera clutch" (box 654), where the two hand controllers can move together. In these implementations, it may be necessary to re-orient the hand controllers and/or device arms relative to the position and/or orientation of the camera. That is, as would be understood, because the camera is capable of pan and tilt functions, the camera has a specific frame of reference with regard to the workspace and device 10. In certain implementations, the console depicts this frame of reference, and the translation and/or orientation of the arms and controllers are fixed relative to the camera orientation. When the camera is moved, it may be necessary to re-orient the controllers and/or arms relative to the second camera frame of reference, which can be designated by $\alpha$. Accordingly, it is possible to urge the hand controls in various directions (such as horizontally relative to the ground), but cause a corresponding vertical motion of the robot arms, in circumstances where the device and camera are pointed straight down. Other versions of this workflow are possible.

FIGS. 29A-D show another possible use of haptic feedback in the force dimension workspace 600. In these implementations, the motion—translation and/or orientation—of the hand controllers have certain limits. In certain embodiments, and as shown in FIGS. 29A-C, the haptic feedback system described above can be used to indicate to the user that the hand controllers have been moved to a limit 602 of their motion. Here another virtual spring could be implemented, or a visual alert, or audible alert, or vibratory alert could be provided.

Figure 30A:
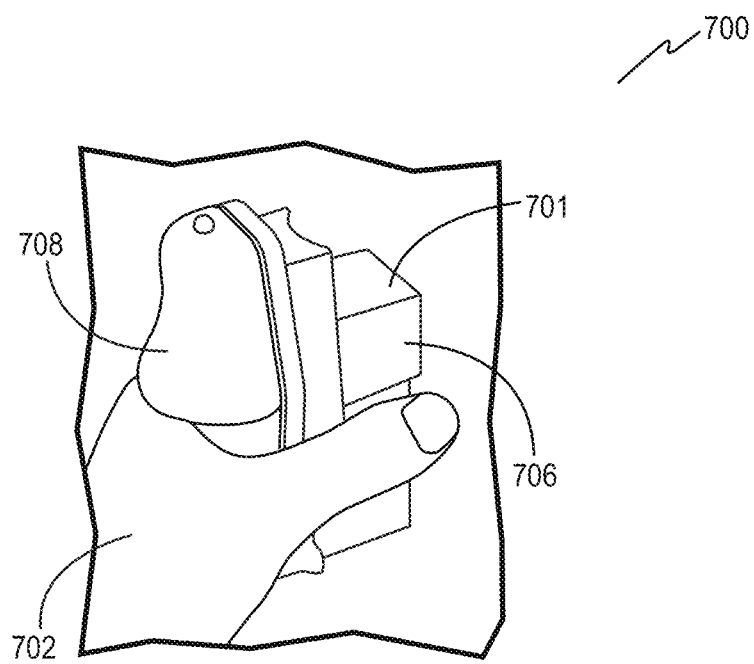
FIG. 30A is a perspective view of a hand controller, according to one implementation.
Figure 30B:
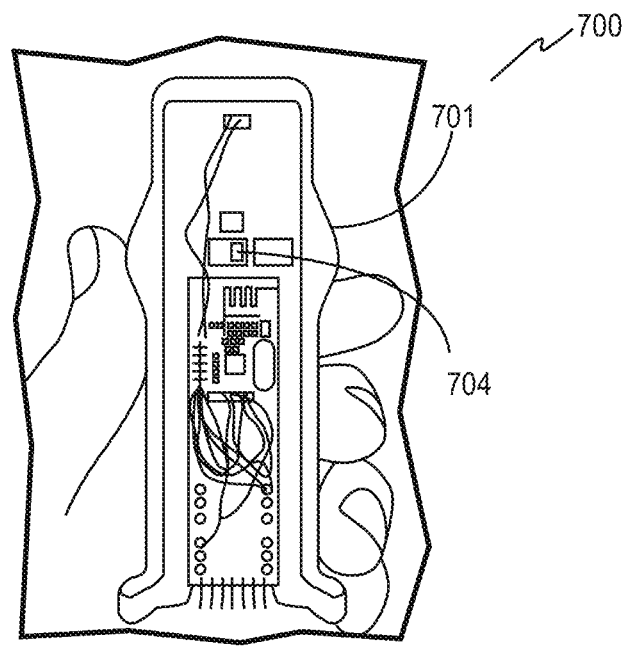

FIGS. 30A-B show an operator detection system 700, which can be operationally integrated with any of the preceding embodiments as part of the user input device or controller 701. In these implementations, the operator detection system 700 is configured to detect the presence of the user 702 so as to prevent unintended motion of the device 10. One implementation is to use a mechanical switch 704 that is engaged as the user 702 inserts his/her hands 702 into contact with the user input device 701 and/or applies pressure to the controller sides 706, 708. Various implementations can also take the form of a capacitive sensor, a pressure sensor, and optical sensor, an optical beam break sensor, or many other forms. In various alternate implementations, the operator detection system 700 can utilize voice activation and/or a vision system.

The various embodiments are disclosed in additional detail in the attached figures, which include some written description therein.

Further, according to certain embodiments, a device as shown and described in the attached figures is inserted into the patient using the following procedure.

First, an incision is made through the abdominal wall using standard techniques. In this embodiment an incision of length 2.5" is required to create a suitable orifice for the system to pass through.

Next, a retractor is placed in the incision. In this embodiment, an Applied Medical Alexis Wound Retractor (http://www.appliedmedical.com/Products/Alexis.aspx) is utilized. It consists of a thin walled (<0.005") flexible tubular membrane with rigid ring shaped end caps. Once the distal ring is inserted into the patient, the proximal ring is rolled to take up the excess slack in tube and pull the wound open.

Then, a port is placed on the retractor. In this embodiment, a modified Applied Medical Gel port (http://www.appliedmedical.com/Products/Gelport.aspx) is utilized. The port is capable of maintain a pressure differential such that insufflation of the abdominal cavity may be achieved. The port is capable of having items (ie robot) plunged through it while maintaining this pressure differential/gas seal. This port consists of a rigid ring which mechanically clamps to the external rigid ring of the retractor. This clamp is capable of sealing to the ring, preserving insufflation pressure. The port further consists of a pair of circular gel membranes. Each membrane is ~0.75" thick. Each membrane has a slit through it. The slit has length of ~50% of the membrane diameter. When assembled, the slit of membrane 1 is rotated 90 degrees with respect to the slit of membrane 2. Due to the gel/conforming nature of the membranes, a seal is maintained against oddly shaped objects as they pass through the slits of the membranes and into the abdominal cavity.

According to one alternative embodiment relating to the port, a lattice of non-elastic cords is embedded in the membranes, mitigating doming/blowout as a result of the internal pressure. In a further alternative, a thin film of a rigid/puncture resistant polymer was deposited at the interface of membrane 1 and 2. The purpose of this polymer is to prevent the end effectors of the robot from puncturing membrane 2 after it passes through the slit in membrane 1.

Once the retractor and gel port are in place, the robot may be inserted into the patient.

Next, a camera (a robot camera as disclosed in the attached figures or an auxiliary camera) is inserted through an auxiliary port to view the insertion.

Next, the insertion/extraction mode of the robot is activated from the GUI.

After that, the robot and/or system determines a path from its current state to its insertion pose (arms straight down), and the operator steps through this path to achieve the required pose.

Subsequently, the operator inserts the robot into the patient (through the gel port and through the retractor port) until the elbow joints of the robot clear the interior surface of the abdominal wall.

After that, the operator steps through the insertion path until the elbows reach their end point (90 degrees). The operator then further inserts the robot into the patient until the shoulder joints clear the interior surface of the abdominal wall. The operator continues to step through the insertion path until the robot achieves its "ready" pose (arms in a nominal operating position), at which point, the surgical procedure can proceed.

When the procedure is complete, device extraction follows the above sequence in reverse.

Although the present invention has been described with reference to preferred embodiments, persons skilled in the art will recognize that changes may be made in form and detail without departing from the spirit and scope of the invention.

What is claimed is:

1. A robotic surgical system, comprising:
   (a) a robotic surgical device comprising:
      (i) an elongate device body having proximal and distal ends;
      (ii) first and second shoulder joints operably coupled to the distal end of the device body;
      (iii) a first segmented robotic arm operably coupled to the first shoulder joint;
      (iv) a second segmented robotic arm operably coupled to the second shoulder joint;
      (v) a camera lumen defined within the device body, the camera lumen comprising:
         (A) a socket defined in the proximal end of the device body, the socket comprising a latch component formed in an inner wall of the socket;
         (B) a seal structure disposed distally of the socket, the seal structure comprising a ring seal and a one-way seal;
         (C) an elongate lumen section defined along a length of the elongate device body, the elongate lumen section defined at a proximal end by the seal structure; and
         (D) a distal lumen opening defined at the distal end of the device body, wherein the distal lumen opening is in fluidic communication with the elongate lumen section; and
   (b) a removable camera component configured to be removably disposed within the robotic surgical device, the removable camera component comprising:
      a controller body comprising a camera clasp component configured to releasably couple with the latch component, thereby releasably locking the controller body into the socket; and
      (ii) an elongate tube operably coupled to the controller body, wherein the elongate tube is configured and sized to be positionable through the elongate lumen section, wherein the elongate tube comprises an optical section, and wherein at least a portion of the optical section extends distally from the distal lumen opening when the elongate tube is positioned through the elongate lumen section.

2. The robotic surgical system of claim 1, wherein the controller body comprises at least one actuator disposed within the controller body, wherein the actuator is constructed and arranged to actuate the camera to pan and tilt.

3. The robotic surgical system of claim 1, wherein the seal structure comprises a ring-seal retention component, wherein the ring seal is retained within the ring-seal retention component.

4. The robotic surgical system of claim 3, wherein the ring-seal retention component comprises at least one protrusion extending from an outer wall of the ring-seal retention component.

5. The robotic surgical system of claim 4, wherein the socket further comprises a channel defined in the inner wall of the socket, wherein the channel is configured to receive the at least one protrusion.

6. The robotic surgical system of claim 1, wherein the seal structure is removable.

7. The robotic surgical system of claim 1, wherein the handle controller body comprises a button operably coupled to the camera clasp component to facilitate unlocking the controller body from the socket.

8. The robotic surgical system of claim 1, wherein the distal lumen opening is positioned between the first and second shoulder joints.

9. The robotic surgical system of claim 1, the elongate tube further comprising:
   (a) a rigid section defining a lumen; and
   (b) a flexible section operably coupling the optical section to the rigid section,
   wherein the optical section is configured to be tiltable at the flexible section in relation to the rigid section, wherein the optical section has a straight configuration and a tilted configuration.

10. The robotic surgical system of claim 7, wherein the button and the camera clasp are portions of a clasping member pivotably coupled to the controller body to enable disengagement of the camera clasp from the latch when the button is pressed.

11. The robotic surgical system of claim 1, wherein the elongate tube is configured to be rotatable in relation to the controller body.

12. The robotic surgical system of claim 1, wherein the inner wall of the socket further comprises a channel configured to receive an insertion device.

13. A robotic surgical system, comprising:
(a) a robotic surgical device comprising:
   (i) a device body comprising a camera lumen defined within the device body, the camera lumen comprising:
      (A) a socket defined in the camera lumen, the socket comprising a latch component formed in an inner wall of the socket;
      (B) a seal structure defined distally of the socket, wherein the seal structure comprises a ring seal and a one-way seal;
      (C) a distal lumen opening defined at a distal end of the device body; and
      (D) an elongate lumen section extending within the device body from the seal structure to the distal lumen opening;
   (ii) first and second shoulder joints operably coupled to a distal end of the device body;
   (iii) a first robotic arm operably coupled to the first shoulder joint; and
   (iv) a second robotic arm operably coupled to the second shoulder joint,
   wherein the distal lumen opening is disposed between the first and second shoulder joints;
(b) a removable camera component configured to be removably disposed within the robotic surgical device, the removable camera component comprising:
   a controller body comprising a camera clasp component configured to releasably couple with the latch component to thereby removably lock at least a distal end of the controller body within the socket; and
   (ii) an elongate tube operably coupled to the controller body, wherein the elongate tube is configured and sized to be positionable through the camera lumen, wherein a portion of the elongate tube is configured to extend distally from the distal lumen opening when the camera component is positioned through the camera lumen.

14. The robotic surgical system of claim 13, wherein the elongate tube comprises:
(a) a rigid section;
(b) an optical section; and
(c) a flexible section operably coupling the optical section to the rigid section.

15. The robotic surgical system of claim 14, wherein the optical section is configured to be tiltable at the flexible section in relation to the rigid section, wherein the optical section has a straight configuration and a tilted configuration.

16. The robotic surgical system of claim 13, wherein the controller body comprises at least one actuator, wherein the at least one actuator is constructed and arranged to actuate the camera component to pan and tilt.

17. The robotic surgical system of claim 13, wherein the seal structure is removable.

18. The robotic surgical system of claim 13, wherein the controller body comprises a controller configured to operate the camera component.

19. The robotic surgical system of claim 13, wherein the elongate tube is configured to be rotatable in relation to the controller body.

20. The robotic surgical system of claim 13, wherein the inner wall of the socket further comprises a channel configured to receive an insertion device.

* * * * *